(12) United States Patent
Griesgraber

(10) Patent No.: US 11,306,083 B2
(45) Date of Patent: Apr. 19, 2022

(54) AMIDE SUBSTITUTED IMIDAZO[4,5-C]QUINOLINE COMPOUNDS WITH A BRANCHED CHAIN LINKING GROUP FOR USE AS AN IMMUNE RESPONSE MODIFIER

(71) Applicant: 3M INNOVATIVE PROPERTIES COMPANY, St. Paul, MN (US)

(72) Inventor: George W. Griesgraber, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 144 days.

(21) Appl. No.: 15/733,207

(22) PCT Filed: Dec. 14, 2018

(86) PCT No.: PCT/IB2018/060122
§ 371 (c)(1),
(2) Date: Jun. 10, 2020

(87) PCT Pub. No.: WO2019/123178
PCT Pub. Date: Jun. 27, 2019

(65) Prior Publication Data
US 2021/0101898 A1   Apr. 8, 2021

Related U.S. Application Data

(60) Provisional application No. 62/608,334, filed on Dec. 20, 2017.

(51) Int. Cl.
*C07D 471/04* (2006.01)
*A61K 39/39* (2006.01)

(52) U.S. Cl.
CPC ............ *C07D 471/04* (2013.01); *A61K 39/39* (2013.01)

(58) Field of Classification Search
CPC .................................................. C07D 471/04
See application file for complete search history.

(56) References Cited

U.S. PATENT DOCUMENTS

| | | |
|---|---|---|
| 3,314,941 A | 4/1967 | Littell |
| 3,700,674 A | 10/1972 | Diehl |
| 4,689,338 A | 8/1987 | Gerster |
| 4,698,348 A | 10/1987 | Gerster |
| 4,929,624 A | 5/1990 | Gerster |
| 4,988,815 A | 1/1991 | Andre |
| 5,037,986 A | 8/1991 | Gerster |
| 5,175,296 A | 12/1992 | Gerster |
| 5,238,944 A | 8/1993 | Wick |
| 5,266,575 A | 11/1993 | Gerster |
| 5,268,376 A | 12/1993 | Gerster |
| 5,346,905 A | 9/1994 | Gerster |
| 5,352,784 A | 10/1994 | Nikolaides |
| 5,367,076 A | 11/1994 | Gerster |
| 5,389,640 A | 2/1995 | Gerster |
| 5,395,937 A | 3/1995 | Nikolaides |
| 5,444,065 A | 8/1995 | Nikolaides |
| 5,446,153 A | 8/1995 | Lindstrom |
| 5,482,936 A | 1/1996 | Lindstrom |
| 5,494,916 A | 2/1996 | Lindstrom |
| 5,525,612 A | 6/1996 | Gerster |
| 5,627,281 A | 5/1997 | Nikolaides |
| 5,644,063 A | 7/1997 | Lindstrom |
| 5,648,516 A | 7/1997 | Nikolaides |
| 5,693,811 A | 12/1997 | Lindstrom |
| 5,714,608 A | 2/1998 | Gerster |

(Continued)

FOREIGN PATENT DOCUMENTS

| | | |
|---|---|---|
| EP | 0394026 | 10/1990 |
| EP | 1104764 | 6/2001 |

(Continued)

OTHER PUBLICATIONS

Bachman, "Synthesis of Substituted Quinolylamines. Derivatives of 4-Amino-7-Chloroquinoline.", J. Org. Chem, 1950, vol. 15, pp. 1278-1284.
Baranov, "Pyrazoles, Imidazoles, and Other 5-Membered Rings.", Chem. Abs. 1976, vol. 85, pp. 94362.
Berenyi, "Ring Transformation of Condensed Dihydro-astriazines.", J. Heterocyclic Chem., 1981, vol. 18, pp. 1537-1540.
Berge, "Pharmaceutical Salts", Journal of Pharmaceutical Sciences, 1977, vol. 66, No. 1, pp. 1-19.

(Continued)

*Primary Examiner* — Paul V Ward
(74) *Attorney, Agent, or Firm* — Jean A. Lown

(57) ABSTRACT

Imidazo[4,5-c]quinoline compounds having an alkylamide substituent that is attached at the N-1 position by a branched chain linking group, single enantiomers of the compounds, pharmaceutical compositions containing the compounds, and methods of making the compounds are disclosed. Methods of use of the compounds as immune response modifiers, for inducing cytokine biosynthesis in humans and animals, and in the treatment of diseases including infectious and neoplastic diseases are also disclosed. Formula (I):

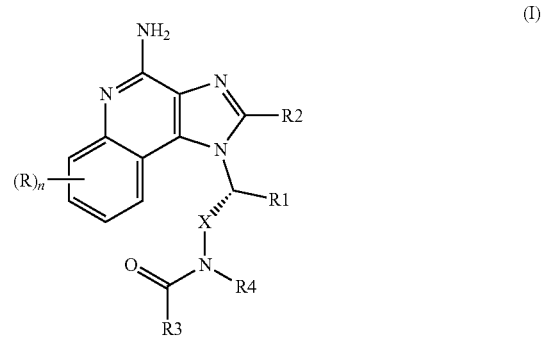

15 Claims, No Drawings

(56) References Cited

U.S. PATENT DOCUMENTS

| | | |
|---|---|---|
| 5,741,908 A | 4/1998 | Gerster |
| 5,756,747 A | 5/1998 | Gerster |
| 5,886,006 A | 3/1999 | Nikolaides |
| 5,939,090 A | 8/1999 | Beaurline |
| 6,039,969 A | 3/2000 | Tomai |
| 6,069,149 A | 5/2000 | Nanba |
| 6,083,505 A | 7/2000 | Miller |
| 6,110,929 A | 8/2000 | Gerster |
| 6,194,425 B1 | 2/2001 | Gerster |
| 6,200,592 B1 | 3/2001 | Tomai |
| 6,245,776 B1 | 6/2001 | Skwierczynski |
| 6,331,539 B1 | 12/2001 | Crooks |
| 6,365,166 B2 | 4/2002 | Beaurline |
| 6,376,669 B1 | 4/2002 | Rice |
| 6,440,992 B1 | 8/2002 | Gerster |
| 6,451,810 B1 | 9/2002 | Coleman |
| 6,486,168 B1 | 11/2002 | Skwierczynski |
| 6,514,985 B1 | 2/2003 | Gerster |
| 6,518,265 B1 | 2/2003 | Kato |
| 6,525,064 B1 | 2/2003 | Dellaria |
| 6,541,485 B1 | 4/2003 | Crooks |
| 6,545,016 B1 | 4/2003 | Dellaria |
| 6,545,017 B1 | 4/2003 | Dellaria |
| 6,558,951 B1 | 5/2003 | Tomai |
| 6,573,273 B1 | 6/2003 | Crooks |
| 6,610,319 B2 | 8/2003 | Tomai |
| 6,627,638 B2 | 9/2003 | Gerster |
| 6,627,640 B2 | 9/2003 | Gerster |
| 6,630,588 B2 | 10/2003 | Rice |
| 6,638,944 B2 | 10/2003 | Mickelson |
| 6,656,938 B2 | 12/2003 | Crooks |
| 6,660,735 B2 | 12/2003 | Crooks |
| 6,660,747 B2 | 12/2003 | Crooks |
| 6,664,260 B2 | 12/2003 | Charles |
| 6,664,264 B2 | 12/2003 | Dellaria |
| 6,664,265 B2 | 12/2003 | Crooks |
| 6,667,312 B2 | 12/2003 | Bonk |
| 6,670,372 B2 | 12/2003 | Charles |
| 6,677,347 B2 | 1/2004 | Crooks |
| 6,677,348 B2 | 1/2004 | Heppner |
| 6,677,349 B1 | 1/2004 | Griesgraber |
| 6,683,088 B2 | 1/2004 | Crooks |
| 6,696,076 B2 | 2/2004 | Tomai |
| 6,696,465 B2 | 2/2004 | Dellaria |
| 6,703,402 B2 | 3/2004 | Gerster |
| 6,706,728 B2 | 3/2004 | Hedenstrom |
| 6,716,988 B2 | 4/2004 | Dellaria |
| 6,720,333 B2 | 4/2004 | Dellaria |
| 6,720,334 B2 | 4/2004 | Dellaria |
| 6,720,422 B2 | 4/2004 | Dellaria |
| 6,743,920 B2 | 6/2004 | Lindstrom |
| 6,756,382 B2 | 6/2004 | Coleman |
| 6,797,718 B2 | 9/2004 | Dellaria |
| 6,800,624 B2 | 10/2004 | Crooks |
| 6,809,203 B2 | 10/2004 | Gerster |
| 6,818,650 B2 | 11/2004 | Griesgraber |
| 6,825,350 B2 | 11/2004 | Crooks |
| 6,841,678 B2 | 1/2005 | Merli |
| 6,852,861 B2 | 2/2005 | Merli |
| 6,878,719 B2 | 4/2005 | Lindstrom |
| 6,888,000 B2 | 5/2005 | Crooks |
| 6,894,060 B2 | 5/2005 | Slade |
| 6,897,221 B2 | 5/2005 | Crooks |
| 6,903,113 B2 | 6/2005 | Heppner |
| 6,916,925 B1 | 7/2005 | Rice |
| 6,921,826 B2 | 7/2005 | Dellaria |
| 6,924,293 B2 | 8/2005 | Lindstrom |
| 6,943,225 B2 | 9/2005 | Lee |
| 6,949,649 B2 | 9/2005 | Bonk |
| 6,953,804 B2 | 10/2005 | Dellaria |
| 6,969,722 B2 | 11/2005 | Heppner |
| 6,989,389 B2 | 1/2006 | Heppner |
| 7,030,129 B2 | 4/2006 | Miller |
| 7,030,131 B2 | 4/2006 | Crooks |
| 7,038,053 B2 | 5/2006 | Lindstrom |
| 7,049,439 B2 | 5/2006 | Crooks |
| 7,078,523 B2 | 7/2006 | Crooks |
| 7,091,214 B2 | 8/2006 | Hays |
| 7,098,221 B2 | 8/2006 | Heppner |
| 7,112,677 B2 | 9/2006 | Griesgraber |
| 7,115,622 B2 | 10/2006 | Crooks |
| 7,125,890 B2 | 10/2006 | Dellaria |
| 7,132,429 B2 | 11/2006 | Griesgraber |
| 7,132,438 B2 | 11/2006 | Frenkel |
| 7,148,232 B2 | 12/2006 | Gerster |
| 7,157,453 B2 | 1/2007 | Crooks |
| 7,163,947 B2 | 1/2007 | Griesgraber |
| 7,179,253 B2 | 2/2007 | Graham |
| 7,199,131 B2 | 4/2007 | Lindstrom |
| 7,214,675 B2 | 5/2007 | Griesgraber |
| 7,220,758 B2 | 5/2007 | Dellaria |
| 7,226,928 B2 | 6/2007 | Mitra |
| 7,276,515 B2 | 10/2007 | Dellaria |
| 7,288,550 B2 | 10/2007 | Dellaria |
| 7,301,027 B2 | 11/2007 | Colombo |
| 7,375,180 B2 | 5/2008 | Gorden |
| 7,387,271 B2 | 6/2008 | Noelle |
| 7,393,859 B2 | 7/2008 | Coleman |
| 7,427,629 B2 | 9/2008 | Kedl |
| 7,485,432 B2 | 2/2009 | Fink |
| 7,544,697 B2 | 6/2009 | Hays |
| 7,576,068 B2 | 8/2009 | Averett |
| 7,578,170 B2 | 8/2009 | Mayer |
| 7,579,359 B2 | 8/2009 | Krepski |
| 7,598,382 B2 | 10/2009 | Hays |
| 7,612,083 B2 | 11/2009 | Griesgraber |
| 7,648,997 B2 | 1/2010 | Kshirsagar |
| 7,655,672 B2 | 2/2010 | Statham |
| 7,687,628 B2 | 3/2010 | Gutman |
| 7,696,159 B2 | 4/2010 | Owens |
| 7,699,057 B2 | 4/2010 | Miller |
| 7,731,967 B2 | 6/2010 | O'Hagan |
| 7,799,800 B2 | 9/2010 | Wightman |
| 7,879,849 B2 | 2/2011 | Hays |
| 7,884,207 B2 | 2/2011 | Stoermer |
| 7,888,349 B2 | 2/2011 | Kshirsagar |
| 7,897,597 B2 | 3/2011 | Lindstrom |
| 7,897,609 B2 | 3/2011 | Niwas |
| 7,897,767 B2 | 3/2011 | Kshirsagar |
| 7,902,209 B2 | 3/2011 | Statham |
| 7,902,210 B2 | 3/2011 | Statham |
| 7,902,211 B2 | 3/2011 | Statham |
| 7,902,212 B2 | 3/2011 | Statham |
| 7,902,213 B2 | 3/2011 | Statham |
| 7,902,214 B2 | 3/2011 | Statham |
| 7,902,215 B2 | 3/2011 | Statham |
| 7,902,216 B2 | 3/2011 | Statham |
| 7,902,242 B2 | 3/2011 | Statham |
| 7,902,243 B2 | 3/2011 | Statham |
| 7,902,244 B2 | 3/2011 | Statham |
| 7,902,245 B2 | 3/2011 | Statham |
| 7,902,246 B2 | 3/2011 | Statham |
| 7,906,506 B2 | 3/2011 | Griesgraber |
| 7,915,281 B2 | 3/2011 | Moser |
| 7,923,560 B2 | 4/2011 | Wightman |
| 7,939,526 B2 | 5/2011 | Radmer |
| 7,943,609 B2 | 5/2011 | Griesgraber |
| 7,968,562 B2 | 6/2011 | Skwierczynski |
| 7,968,563 B2 | 6/2011 | Kshirsager |
| 7,993,659 B2 | 8/2011 | Noelle |
| 8,017,779 B2 | 9/2011 | Merrill |
| 8,026,366 B2 | 9/2011 | Prince |
| 8,034,938 B2 | 10/2011 | Griesgraber |
| 8,088,790 B2 | 1/2012 | Kshirsagar |
| 8,436,178 B2 | 5/2013 | Bonnert |
| 8,673,932 B2 | 3/2014 | Kshirsagar |
| 8,691,837 B2 | 4/2014 | Krepski |
| 8,697,873 B2 | 4/2014 | Krepski |
| 9,034,336 B2 | 5/2015 | Ferguson |
| 9,107,958 B2 | 8/2015 | Wightman |
| 9,334,268 B2 | 5/2016 | Hoves |
| 9,585,968 B2 | 3/2017 | Wightman |
| 2002/0055517 A1 | 5/2002 | Smith |
| 2002/0058674 A1 | 5/2002 | Hedenstrom |

(56) References Cited

U.S. PATENT DOCUMENTS

| | | |
|---|---|---|
| 2002/0107262 A1 | 8/2002 | Lindstrom |
| 2003/0133913 A1 | 7/2003 | Tomai |
| 2003/0139364 A1 | 7/2003 | Krieg |
| 2004/0014779 A1 | 1/2004 | Gorden |
| 2004/0132079 A1 | 7/2004 | Gupta |
| 2004/0175336 A1 | 9/2004 | Egging |
| 2004/0180919 A1 | 9/2004 | Lee |
| 2004/0191833 A1 | 9/2004 | Fink |
| 2004/0197865 A1 | 10/2004 | Gupta |
| 2004/0202720 A1 | 10/2004 | Wightman |
| 2004/0214851 A1 | 10/2004 | Birmachu |
| 2004/0258698 A1 | 12/2004 | Wightman |
| 2004/0265351 A1 | 12/2004 | Miller |
| 2005/0048072 A1 | 3/2005 | Kedl |
| 2005/0059072 A1 | 3/2005 | Birmachu |
| 2005/0070460 A1 | 3/2005 | Hammerbeck |
| 2005/0096259 A1 | 5/2005 | Tomai |
| 2005/0106300 A1 | 5/2005 | Chen |
| 2005/0158325 A1 | 7/2005 | Hammerbeck |
| 2005/0165043 A1 | 7/2005 | Miller |
| 2005/0171072 A1 | 8/2005 | Tomai |
| 2005/0239735 A1 | 10/2005 | Miller |
| 2005/0245562 A1 | 11/2005 | Echeverria |
| 2006/0045885 A1 | 3/2006 | Kedl |
| 2006/0045886 A1 | 3/2006 | Kedl |
| 2006/0051374 A1 | 3/2006 | Miller |
| 2006/0088542 A1 | 4/2006 | Braun |
| 2006/0142202 A1 | 6/2006 | Alkan |
| 2006/0142235 A1 | 6/2006 | Miller |
| 2006/0195067 A1 | 8/2006 | Wolter |
| 2006/0216333 A1 | 9/2006 | Miller |
| 2007/0060754 A1 | 3/2007 | Lindstrom |
| 2007/0066639 A1 | 3/2007 | Kshirsagar |
| 2007/0072893 A1 | 3/2007 | Krepski |
| 2007/0099901 A1 | 5/2007 | Krepski |
| 2007/0123559 A1 | 5/2007 | Statham |
| 2007/0166384 A1 | 7/2007 | Zarraga |
| 2007/0167479 A1 | 7/2007 | Busch |
| 2007/0213355 A1 | 9/2007 | Capraro |
| 2007/0219196 A1 | 9/2007 | Krepski |
| 2007/0243215 A1 | 10/2007 | Miller |
| 2007/0259881 A1 | 11/2007 | Dellaria |
| 2007/0259907 A1 | 11/2007 | Prince |
| 2007/0292456 A1 | 12/2007 | Hammerbeck |
| 2008/0015184 A1 | 1/2008 | Kshirsagar |
| 2008/0039533 A1 | 2/2008 | Sahouani |
| 2008/0063714 A1 | 3/2008 | Sahouani |
| 2008/0119508 A1 | 5/2008 | Slade |
| 2008/0188513 A1 | 8/2008 | Skwierczynski |
| 2008/0193468 A1 | 8/2008 | Levy |
| 2008/0193474 A1 | 8/2008 | Griesgraber |
| 2008/0207674 A1 | 8/2008 | Stoesz |
| 2008/0213308 A1 | 9/2008 | Valiante |
| 2008/0262021 A1 | 10/2008 | Capraro |
| 2008/0262022 A1 | 10/2008 | Lee |
| 2008/0306252 A1 | 12/2008 | Crooks |
| 2008/0306266 A1 | 12/2008 | Martin |
| 2008/0312434 A1 | 12/2008 | Lindstrom |
| 2008/0318998 A1 | 12/2008 | Prince |
| 2009/0005371 A1 | 1/2009 | Rice |
| 2009/0005376 A1 | 1/2009 | Krepski |
| 2009/0017076 A1 | 1/2009 | Miller |
| 2009/0023720 A1 | 1/2009 | Kshirsagar |
| 2009/0023722 A1 | 1/2009 | Coleman |
| 2009/0029988 A1 | 1/2009 | Kshirsagar |
| 2009/0030030 A1 | 1/2009 | Bonk |
| 2009/0030031 A1 | 1/2009 | Kshirsagar |
| 2009/0035323 A1 | 2/2009 | Stoermer |
| 2009/0062272 A1 | 3/2009 | Bonk |
| 2009/0069299 A1 | 3/2009 | Merrill |
| 2009/0069314 A1 | 3/2009 | Kshirsagar |
| 2009/0075980 A1 | 3/2009 | Hays |
| 2009/0099161 A1 | 4/2009 | Rice |
| 2009/0105295 A1 | 4/2009 | Kshirsagar |
| 2009/0124611 A1 | 5/2009 | Hays |
| 2009/0124652 A1 | 5/2009 | Ach |
| 2009/0163532 A1 | 6/2009 | Perman |
| 2009/0163533 A1 | 6/2009 | Hays |
| 2009/0176821 A1 | 7/2009 | Kshirsagar |
| 2009/0202443 A1 | 8/2009 | Miller |
| 2009/0221551 A1 | 9/2009 | Kshirsagar |
| 2009/0221556 A1 | 9/2009 | Kshirsagar |
| 2009/0240055 A1 | 9/2009 | Krepski |
| 2009/0246174 A1 | 10/2009 | Rook |
| 2009/0253695 A1 | 10/2009 | Kshirsagar |
| 2009/0270443 A1 | 10/2009 | Stoermer |
| 2009/0298821 A1 | 12/2009 | Kshirsagar |
| 2009/0306388 A1 | 12/2009 | Zimmerman |
| 2010/0028381 A1 | 2/2010 | Gorski |
| 2010/0056557 A1 | 3/2010 | Benninghoff |
| 2010/0096287 A1 | 4/2010 | Stoesz |
| 2010/0113565 A1 | 5/2010 | Gorden |
| 2010/0152230 A1 | 6/2010 | Dellaria |
| 2010/0158928 A1 | 6/2010 | Stoermer |
| 2010/0173906 A1 | 7/2010 | Griesgraber |
| 2010/0180902 A1 | 7/2010 | Miller |
| 2010/0240693 A1 | 9/2010 | Lundquist |
| 2011/0021554 A1 | 1/2011 | Stoesz |
| 2013/0230578 A1 | 9/2013 | Wightman |
| 2017/0173164 A1 | 6/2017 | Wightman |

FOREIGN PATENT DOCUMENTS

| | | |
|---|---|---|
| JP | 09176116 | 7/1997 |
| JP | 09208584 | 8/1997 |
| JP | 11080156 | 3/1999 |
| JP | 11-222432 | 8/1999 |
| JP | 2000-247884 | 9/2000 |
| WO | WO 1998-017279 | 4/1998 |
| WO | WO 2000-076505 | 12/2000 |
| WO | WO 2002-036592 | 5/2002 |
| WO | WO 2004-032829 | 4/2004 |
| WO | WO 2005-003064 | 1/2005 |
| WO | WO 2005-018555 | 3/2005 |
| WO | WO 2005-051317 | 6/2005 |
| WO | WO 2006-028451 | 3/2006 |
| WO | WO 2006-028962 | 3/2006 |
| WO | WO 2006-063072 | 6/2006 |
| WO | WO 2006-121528 | 11/2006 |
| WO | WO 2007-007775 | 3/2007 |
| WO | WO 2012-167081 | 12/2012 |
| WO | WO 2017-040233 | 3/2017 |

OTHER PUBLICATIONS

Brennan, "Automated Bioassay of Interferons in Micro-test Plates.", Biotechniques, 1983, vol. 78, 6 pages.

Chollet, "Development of a Topically Active Imiquimod Formulation.", Pharmaceutical Development and Technology, 1999, vol. 4, No. 1, pp. 35-43.

Gerster "Synthesis and Structure-Activity-Relationships of 1H-Imidazo[4.5-c] quinolines That Induce Interferon Production" J. Med Chem. 2005, vol. 48, pp. 3481-3491.

Gubitz, "Chiral separation by chromatographic and electromigration techniques: A review", Biopharmaceutics and Drug Disposition, 2001, vol. 22, pp. 291-336.

Izumi, "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", Bioorganic & Medicinal Chemistry, 2003, vol. 11, pp. 2541-2550.

Jain, "Chemical and Pharmacological Investigations of Some ω-Substituted Alkylamino-3-aminopyridines.", J. Med. Chem., 1968, vol. 11, pp. 87-92.

Mane, "Racemic drug resolution : A comprehensive guide", Analytical Methods, 2016, vol. 8, pp. 7567-7586.

Masiukiewicz, "Organic Preparations and Procedures International (OPPI)", vol. 34, 2002, pp. 531-537.

Okamoto, "Chiral HPLC for efficient resolution of enantiomers", Chemical Society Reviews, 2008, vol. 37, pp. 2593-2608.

Smirnov, "Vaccine Adjuvant Activity of 3M-052: An Imidazoquinoline Designed for Local Activity without Systemic Cytokine Induction", Vaccine 29, pp. 5434-5442 (2011).

(56) References Cited

OTHER PUBLICATIONS

Testerman, "Cytokine Induction by the Immunomodulators Imiquimod and S-27609.", Journal of Leukocyte Biology, 1995, vol. 58, pp. 365-372.
Wozniak, "The Amination of 3-nitro-1,5-naphthyridines by Liquid Ammonia/Potassium Permanganate[1,2]. A New and Convenient Amination Method.", Journal of the Royal Netherlands Chemical Society, 1983, vol. 102, pp. 511-513.
Wuts, "Greene's Protective Groups in Organic Synthesis", John Wiley & Sons, 2014, Table of Contents, 7 pages.
International Search report for PCT International Application No. PCT/IB2018/060122 dated Feb. 27, 2019, 5 pages.

AMIDE SUBSTITUTED IMIDAZO[4,5-C]QUINOLINE COMPOUNDS WITH A BRANCHED CHAIN LINKING GROUP FOR USE AS AN IMMUNE RESPONSE MODIFIER

CROSS REFERENCE TO RELATED APPLICATIONS

This application is a national stage filing under 35 U.S.C. 371 of PCT/IB2018/060122, filed Dec. 14, 2018, which claims the benefit of U.S. Provisional Patent Application No. 62/608,334, filed Dec. 20, 2017, the disclosure of which is incorporated by reference herein its/their entirety.

BACKGROUND

Some drug compounds act by stimulating certain key aspects of the immune system, as well as by suppressing certain other aspects (e.g., U.S. Pat. No. 6,039,969 (Tomai et al.) and U.S. Pat. No. 6,200,592 (Tomai et al.)). These compounds are sometimes referred to as immune response modifiers (IRMs). Some IRM compounds are useful for treating viral diseases, neoplasias, and $T_H2$-mediated diseases. Some IRM compounds are useful as vaccine adjuvants.

IRM compounds have been reported based on the following bicyclic and tricyclic ring systems: 1H-imidazo[4,5-c] quinolin-4-amines (e.g., U.S. Pat. No. 4,689,338 (Gerster)); 1H-imidazo[4,5-c]pyridin-4-amines (e.g., U.S. Pat. No. 5,446,153 (Lindstrom et al.)); 1H-imidazo[4,5-c][1,5]naphthyidin-4-amines (e.g., U.S. Pat. No. 6,194,425 (Gerster et al.)); thiazolo[4,5-c]quinolone-4-amines and oxazolo[4,5-c] quinolone-4-amines (e.g., U.S. Pat. No. 6,110,929 (Gerster et al.)); 6,7,8,9-1H-tetrahydro-1H-imidazo[4,5-c]quinolin-4-amines (e.g., U.S. Pat. No. 5,352,784 (Nikolaides et al.)); 2H-pyrazolo[3,4-c]quinolone-4-amines (e.g., U.S. Pat. No. 7,544,697 (Hays et al.)); and N-1 and 2-substituted 1H-imidazo[4,5-c]quinolin-4-amines (e.g., U.S. Pat. No. 6,331,539 (Crooks et al.), U.S. Pat. No. 6,451,810 (Coleman et al.), U.S. Pat. No. 6,664,264 (Dellaria et al.), U.S. Pat. No. 8,691,837 (Krepski et al.), U.S. Pat. No. 8,088,790 (Kshirsagar et al.), U.S. Pat. No. 8,673,932 (Kshirsagar et al.), U.S. Pat. No. 8,697,873 (Krepski et al.), and U.S. Pat. No. 7,915,281 (Moser et al.)).

SUMMARY

New compounds that can be useful in inducing cytokine biosynthesis in humans and animals are disclosed. Such compounds are of the following Formula I:

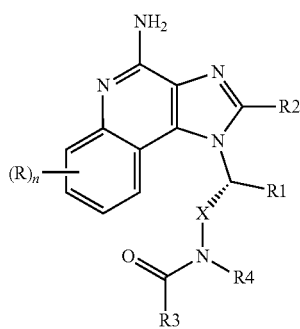

Formula I wherein R, R1, R2, R3, R4, X, and n are as defined below.

The racemate (Formula VI) is also disclosed wherein R, R1, R2, R3, R4, X, and n are as defined below.

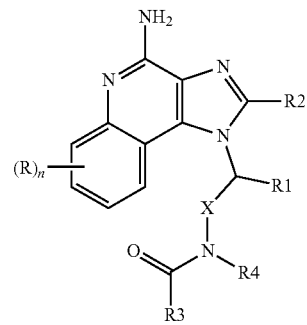

Formula VI

The compounds and salts, such as pharmaceutically acceptable salts, of Formula I and Formula VI can be used as immune response modifiers due to their ability to induce cytokine biosynthesis (e.g., induce the synthesis of at least one cytokine) and otherwise modulate the immune response when administered to humans or animals. The compounds can therefore be used in the treatment of a variety of conditions such as viral diseases and tumors that are responsive to such changes in the immune response. The compounds can also be used as vaccine adjuvants when administered in combination with a vaccine.

Pharmaceutical compositions containing an effective amount of a compound of Formula I or a compound of Formula VI (including pharmaceutically acceptable salts thereof) are disclosed.

Also disclosed are methods of inducing cytokine biosynthesis in a human or animal, treating a viral disease in a human or animal, and treating a neoplastic disease in a human or animal by administering to the human or animal a compound of Formula I or a Compound of Formula VI and/or pharmaceutically acceptable salt thereof.

Methods for synthesizing compounds of Formula I and compounds of Formula VI are provided.

The above summary of the present invention is not intended to describe each disclosed embodiment or every implementation of the present invention. The description that follows more particularly exemplifies illustrative embodiments. In several places throughout the description, guidance is provided through lists of examples, which can be used in various combinations. In each instance, the recited list serves only as a representative group and should not be interpreted as an exhaustive list.

DETAILED DESCRIPTION

As used herein, "a", "an", "the", "at least one", and "one or more" are used interchangeably and are intended to include both the singular and the plural except in cases where the singular alone is specifically called for or clearly required by the context.

As used herein, "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

"Ph" is used as an abbreviation for a phenyl group.

"BOC" is used as an abbreviation for —C(O)OC(CH$_3$)$_3$.

"CBZ" is used as an abbreviation for —C(O)OCH$_2$Ph.

As used herein, "pharmaceutically acceptable carriers" include those carriers that can deliver therapeutically effective amounts of one or more of the compounds or salts of the disclosure to a subject by a chosen route of administration, are generally tolerated by the subject, and have an acceptable toxicity profile (preferably minimal to no toxicity at an administered dose). Some suitable pharmaceutically acceptable carriers are described in Remington's Pharmaceutical Sciences, 18$^{th}$ Edition (1990), Mack Publishing Co. and can be readily selected by one of ordinary skill in the art.

"Therapeutically effective amount" and "effective amount" are defined as an amount of compound or salt sufficient to induce a therapeutic or prophylactic effect, such as cytokine induction, immunomodulation, antitumor activity, and/or antiviral activity.

"Treat", "Treatment" or variations thereof refer to reducing, limiting progression, ameliorating, preventing, or resolving to any extent the symptoms or signs related to a condition.

"Ameliorate" and "ameliorating" refers to any reduction in the extent, severity, frequency, and/or likelihood of a symptom or clinical characteristic of a particular condition.

"Antigen" refers to any substance that can be bound by an antibody in a manner that is immuno-specific to some degree.

The terms "alkyl", "alkenyl", "alkynyl" and the prefix "alk-" are inclusive of straight chain groups, branched chain groups, cyclic groups, and combinations thereof, e.g., cycloalkyl and cycloalkenyl. Alkyl groups are saturated aliphatic hydrocarbons. Alkenyl groups are unsaturated aliphatic hydrocarbons having one or more carbon-carbon double bonds. Alkynyl groups are unsaturated aliphatic hydrocarbons having one or more carbon-carbon triple bonds. Unless otherwise specified, these groups contain from 1 to 20 carbon atoms, with alkenyl groups containing from 2 to 20 carbon atoms and alkynyl groups containing from 2-20 atoms. In some embodiments, these groups have a total of up to 20 carbon atoms, up to 18 carbon atoms, up to 16 carbon atoms, up to 14 carbon atoms, up to 12 carbon atoms, up to 10 carbon atoms, up to 8 carbon atoms, up to 3 carbon atoms, or up to 2 carbon atoms. In some embodiments, these groups have at least 1 carbon atom, at least 2 carbon atoms, at least 3 carbon atoms, or at least 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, norbornenyl, and the like.

The term "$C_{x-y}$alkyl", "$C_{x-y}$alkoxy", and "$C_{x-y}$alkylene" are inclusive of straight chain groups, branched chain groups, cyclic groups, and combinations thereof that have X to Y carbon atoms. For example, a "$C_{1-5}$alkyl" includes alkyl groups of 1 carbon, 2 carbons, 3 carbons, 4 carbons, and 5 carbons. Some examples of "$C_{1-5}$alkyl" include methyl, ethyl, n-propyl, isopropyl, isobutyl, isomeric pentyls, cyclopropyl, cyclopentyl, —CH$_2$-cyclopropyl.

Unless otherwise specified, "alkylene", "alkenylene", and "alkynylene" are the diradical equivalents of the "alkyl", "alkenyl", and "alkynyl" defined above. The terms, "alkylenyl", "alkenylenyl", and "alkynylenyl" are used when "alkylene", "alkenylene", and "alkynylene" respectively, are substituted. For example, an alkoxyalkylenyl group comprises an alkylene moiety to which an alkoxy group is attached (e.g., —CH$_2$OCH$_3$, —CH$_2$CH$_2$OCH$_3$, —CH$_2$OCH$_2$CH$_3$, etc.). As a further example, a hydroxyalkylenyl group comprises an alkylene moiety to which a hydroxyl group is attached (e.g., —CH$_2$OH, —CH$_2$CH$_2$OH, etc.). As yet another example arylalkylenyl group comprises an alkylene moiety to which an aryl group is attached [e.g., —CH$_2$Ph, —CH$_2$CH$_2$Ph, etc.].

An alkylene group with carbon atoms optionally "interrupted" by one or more —O— groups refers to having carbon atoms on either side of the —O—. Examples include —CH$_2$CH$_2$—O—CH$_2$CH$_2$—, —CH$_2$—CH$_2$—O—CH$_2$—CH$_2$—O—CH$_2$CH$_2$—, —(CH$_2$)$_{2-4}$—(OCH$_2$CH$_2$—)$_{1-5}$, —(CH$_2$)$_{2-6}$—(OCH$_2$CH$_2$—)$_{1-4}$, etc.

The term "aryl" as used herein includes carbocyclic aromatic rings or ring systems. Examples of aryl groups include phenyl (designated by the abbreviation "Ph" herein), naphthyl, and biphenyl.

The terms "arylene", "-arylene-", "heteroarylene", and "-heteroarylene-" are the diradical equivalents of the "aryl" and "heteroaryl" groups defined above. The terms "arylenyl" and "heteroarylenyl" are used when "arylene" and "heteroarylene" are substituted. For example, an alkylarylenyl group comprises an arylene moiety to which an alkyl group is attached (e.g., -Ph-CH$_3$).

The "salt" of a compound includes pharmaceutically acceptable salts, such as those described in Berge, Stephen M., "Pharmaceutical Salts", *Journal of Pharmaceutical Sciences*, 1977, 66, pages 1-19. For example, salts can be prepared by reacting a free base compound (that is, one not in a salt form) with an inorganic or organic acid such as, for example, hydrochloric acid, sulfuric acid, hydrobromic acid, methane sulfonic acid, ethane sulfonic acid, malic acid, maleic acid, acetic acid, trifluoroacetic acid, para-toluenesulfonic acid, salicylic acid, succinic acid, tartaric acid, citric acid, pamoic acid, xinafoic acid, oxalic acid, and the like. Typical pharmaceutically acceptable salts include hydrochloride and dihydrochloride.

This disclosure provides compounds of the following Formula I:

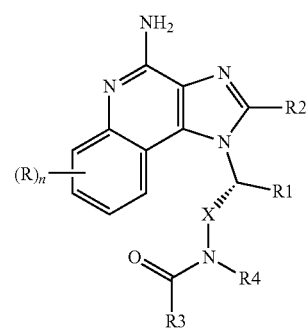

Formula I wherein R, R1, R2, R3, R4, X, and n are as defined below; and pharmaceutically acceptable salts thereof.

For compounds and salts, such as pharmaceutically acceptable salts, of Formula I:

R is selected from the group consisting of halogen, hydroxy, alkyl, alkoxy, and —C(O)—O-alkyl;

n is an integer 0 or 1;

X is alkylene, wherein the alkylene group can be optionally interrupted by one or more —O— groups;

R1 is selected from the group consisting of $C_{1-5}$alkyl and —$C_{1-3}$alkylene-O—$C_{1-3}$alkyl;

R2 is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$;

R3 is alkyl, wherein the alkyl group can be optionally interrupted by one or more —O— groups;

R4 is selected from the group consisting of hydrogen, methyl, ethyl, n-propyl, and isopropyl.

In some embodiments of Formula I, n is 0.

In some embodiments of Formula I, R is selected from the group consisting of halogen, hydroxy, $C_{1-7}$alkyl, $C_{1-7}$alkoxy, and —C(O)—O—$C_{1-5}$alkyl.

In some embodiments of Formula I, R is selected from the group consisting of halogen and hydroxy.

In some embodiments of Formula I, R is a halogen.

In some embodiments of Formula I, R is selected from the group consisting of hydroxy, F, and Cl.

In some embodiments of Formula I, R1 is —$C_{1-3}$alkylene-O—$C_{1-3}$alkyl.

In some embodiments of Formula I, R1 is selected from the group consisting of —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$OCH$_3$, —CH$_2$OCH$_2$CH$_3$, and —CH$_2$CH$_2$OCH$_3$.

In some embodiments of Formula I, R1 is selected from the group consisting of —CH$_2$OCH$_3$, —CH$_2$OCH$_2$CH$_3$, and —CH$_2$CH$_2$OCH$_3$.

In some embodiments of Formula I, R1 is selected from the group consisting of —CH$_2$OCH$_3$, —CH$_2$OCH$_2$CH$_3$.

In some embodiments of Formula I, R2 is selected from the group consisting of hydrogen, methyl, and ethyl.

In some embodiments of Formula I, R2 is hydrogen.

In some embodiments of Formula I, R2 is selected from the group consisting of hydrogen, —CH$_3$, —CH$_2$CH$_3$, —CH$_2$CH$_2$CH$_3$, —CH$_2$CH$_2$CH$_2$CH$_3$.

In some embodiments of Formula I, R3 is $C_{1-19}$alkyl.
In some embodiments of Formula I, R3 is $C_{1-4}$alkyl.
In some embodiments of Formula I, R3 is $C_{5-17}$alkyl.
In some embodiments of Formula I, R3 is $C_{7-19}$alkyl.
In some embodiments of Formula I, R3 is $C_{7-17}$alkyl.
In some embodiments of Formula I, R3 is $C_{9-19}$alkyl.
In some embodiments of Formula I, R3 is $C_{9-17}$alkyl.
In some embodiments of Formula I, R3 is $C_{11-17}$alkyl.
In some embodiments of Formula I, R3 is $C_{11-15}$alkyl.
In some embodiments of Formula I, R3 is $C_{7-11}$alkyl.
In some embodiments of Formula I, R3 is $C_{19}$alkyl.
In some embodiments of Formula I, R3 is $C_{17}$alkyl.
In some embodiments of Formula I, R3 is $C_{15}$alkyl.
In some embodiments of Formula I, R3 is $C_{13}$alkyl.
In some embodiments of Formula I, R3 is $C_{11}$alkyl.
In some embodiments of Formula I, R3 is —(CH$_2$)$_{4-18}$CH$_3$.
In some embodiments of Formula I, R3 is —(CH$_2$)$_{6-16}$CH$_3$.
In some embodiments of Formula I, R3 is —(CH$_2$)$_{8-16}$CH$_3$.
In some embodiments of Formula I, R3 is —(CH$_2$)$_{10-16}$CH$_3$.

In some embodiments of Formula I, R3 is selected from the group consisting of —CH$_3$, —CH$_2$CH$_3$, —CH$_2$CH$_2$CH$_3$, —CH(CH$_3$)$_2$, —CH$_2$(CH$_2$)$_2$CH$_3$, —CH$_2$CH(CH$_3$)$_2$, —CH$_2$(CH$_2$)$_3$CH$_3$, —CH$_2$(CH$_2$)$_4$CH$_3$, —CH$_2$(CH$_2$)$_5$CH$_3$, —CH$_2$(CH$_2$)$_6$CH$_3$, —CH$_2$(CH$_2$)$_7$CH$_3$, —CH$_2$(CH$_2$)$_8$CH$_3$, —CH$_2$(CH$_2$)$_9$CH$_3$, —CH$_2$(CH$_2$)$_{10}$CH$_3$, —CH$_2$(CH$_2$)$_{11}$CH$_3$, —CH$_2$(CH$_2$)$_{12}$CH$_3$, —CH$_2$(CH$_2$)$_{13}$CH$_3$, —CH$_2$(CH$_2$)$_{14}$CH$_3$, —CH$_2$(CH$_2$)$_{15}$CH$_3$, —CH$_2$(CH$_2$)$_{16}$CH$_3$, and —CH$_2$(CH$_2$)$_{17}$CH$_3$.

In some embodiments of Formula I, R3 is selected from the group consisting of —CH$_3$, —CH$_2$CH$_3$, —CH$_2$CH$_2$CH$_3$, —CH(CH$_3$)$_2$, —CH$_2$(CH$_2$)$_2$CH$_3$, —CH$_2$CH(CH$_3$)$_2$, —CH$_2$(CH$_2$)$_3$CH$_3$, —CH$_2$(CH$_2$)$_4$CH$_3$.

In some embodiments of Formula I, R3 is selected from the group consisting of —CH$_2$(CH$_2$)$_5$CH$_3$, —CH$_2$(CH$_2$)$_7$CH$_3$, —CH$_2$(CH$_2$)$_9$CH$_3$, —CH$_2$(CH$_2$)$_{11}$CH$_3$, —CH$_2$(CH$_2$)$_{13}$CH$_3$, —CH$_2$(CH$_2$)$_{15}$CH$_3$, and —CH$_2$(CH$_2$)$_{17}$CH$_3$.

In some embodiments of Formula I, R3 is selected from the group consisting of —CH$_2$(CH$_2$)$_9$CH$_3$, —CH$_2$(CH$_2$)$_{11}$CH$_3$, and —CH$_2$(CH$_2$)$_{13}$CH$_3$.

In some embodiments of Formula I, R3 is —CH$_2$(CH$_2$)$_7$CH$_3$.
In some embodiments of Formula I, R3 is —CH$_2$(CH$_2$)$_9$CH$_3$.
In some embodiments of Formula I, R3 is —CH$_2$(CH$_2$)$_{11}$CH$_3$.
In some embodiments of Formula I, R3 is —CH$_2$(CH$_2$)$_{13}$CH$_3$.

In some embodiments of Formula I, R3 is selected from the group consisting of —CH$_2$CH$_2$—O—(CH$_2$)$_{1-16}$CH$_3$, —CH$_2$CH$_2$CH$_2$—O—(CH$_2$)$_{1-15}$CH$_3$, —CH$_2$(CH$_2$)$_2$CH$_2$—O—(CH$_2$)$_{1-14}$CH$_3$, —CH$_2$(CH$_2$)$_3$CH$_2$—O—(CH$_2$)$_{1-13}$CH$_3$, —CH$_2$(CH$_2$)$_4$CH$_2$—O—(CH$_2$)$_{1-12}$CH$_3$, —CH$_2$(CH$_2$)$_5$CH$_2$—O—(CH$_2$)$_{1-11}$CH$_3$, —CH$_2$(CH$_2$)$_6$CH$_2$—O—(CH$_2$)$_{1-10}$CH$_3$, —CH$_2$(CH$_2$)$_7$CH$_2$—O—(CH$_2$)$_{1-9}$CH$_3$, —CH$_2$(CH$_2$)$_8$CH$_2$—O—(CH$_2$)$_{1-8}$CH$_3$, —CH$_2$(CH$_2$)$_9$CH$_2$—O—(CH$_2$)$_{1-7}$CH$_3$, —CH$_2$(CH$_2$)$_{10}$CH$_2$—O—(CH$_2$)$_{1-6}$CH$_3$, —CH$_2$(CH$_2$)$_{11}$CH$_2$—O—(CH$_2$)$_{1-5}$CH$_3$, —CH$_2$(CH$_2$)$_{12}$CH$_2$—O—(CH$_2$)$_{1-4}$CH$_3$, —CH$_2$(CH$_2$)$_{13}$CH$_2$—O—(CH$_2$)$_{1-3}$CH$_3$, —CH$_2$(CH$_2$)$_{14}$CH$_2$—O—(CH$_2$)$_{1-2}$CH$_3$, —CH$_2$(CH$_2$)$_{15}$CH$_2$—O—CH$_2$CH$_3$, —CH$_2$(CH$_2$)$_{1-17}$—OCH$_3$.

In some embodiments of Formula I, R4 is selected from the group consisting of hydrogen and methyl.

In some embodiments of Formula I, R4 is hydrogen.

In some embodiments of Formula I, X is alkylene.

In some embodiments of Formula I, X is a $C_{1-8}$alkylene optionally interrupted by one or more —O— groups.

In some embodiments of Formula I, X is $C_{1-8}$alkylene.
In some embodiments of Formula I, X is $C_{2-6}$alkylene.
In some embodiments of Formula I, X is $C_{2-5}$alkylene.
In some embodiments of Formula I, X is a $C_{2-4}$alkylene.

In some embodiments of Formula I, X is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$—O—CH$_2$CH$_2$—, and —CH$_2$CH$_2$—O—CH$_2$CH$_2$CH$_2$—.

In some embodiments of Formula I, X is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—.

In some embodiments of Formula I, X is —CH$_2$CH$_2$CH$_2$—.

In some embodiments of Formula I, X is alkylene optionally interrupted by one or more —O— groups; R1 is selected from the group consisting of $C_{1-5}$alkyl and —$C_{1-3}$alkylene-O—$C_{1-3}$alkyl; R2 is selected from the group consisting of hydrogen, methyl, and ethyl; R3 is $C_{7-17}$alkyl; R4 is hydrogen; and n is 0.

In some embodiments of Formula I, X is $C_{2-5}$alkylene; R1 is selected from the group consisting of —CH$_2$OCH$_3$ and —CH$_2$OCH$_2$CH$_3$; R2 is selected from the group consisting of hydrogen, methyl, and ethyl; R3 is C$_{7-17}$alkyl; R4 is hydrogen; and n is 0.

In some embodiments of Formula I, X is C$_{2-5}$alkylene; R1 is selected from the group consisting of —CH$_2$OCH$_3$ and —CH$_2$OCH$_2$CH$_3$; R2 is hydrogen; R3 is C$_{7-17}$alkyl; R4 is hydrogen; and n is 0.

In some embodiments of Formula I, X is selected from the group consisting of —CH$_2$CH$_2$CH$_2$—, —CH$_2$CH$_2$CH$_2$CH$_2$—, and —CH$_2$CH$_2$CH$_2$CH$_2$—; R1 is selected from the group consisting of —CH$_2$OCH$_3$ and —CH$_2$OCH$_2$CH$_3$; R2 is selected from the group consisting of hydrogen, methyl, and ethyl; R3 is C$_{7-17}$alkyl; R4 is hydrogen; and n is 0.

In some embodiments of Formula I, X is —CH$_2$CH$_2$CH$_2$—; R1 is selected from the group consisting of —CH$_2$OCH$_3$, —CH$_2$OCH$_2$CH$_3$; R2 is hydrogen; R3 is C$_{7-17}$alkyl; R4 is hydrogen; and n is 0.

In some embodiments of Formula I, X is —CH$_2$CH$_2$CH$_2$—; R1 is selected from the group consisting of —CH$_2$OCH$_3$ and —CH$_2$OCH$_2$CH$_3$; R2 is hydrogen; R3 is C$_{9-15}$alkyl; R4 is hydrogen; and n is 0.

In some embodiments of Formula I, X is —CH$_2$CH$_2$CH$_2$—; R1 is selected from the group consisting of —CH$_2$OCH$_3$ and —CH$_2$OCH$_2$CH$_3$; R2 is hydrogen; R3 is C$_{11-15}$alkyl; R4 is hydrogen; and n is 0.

In some embodiments of Formula I, X is —CH$_2$CH$_2$CH$_2$—; R1 is selected from the group consisting of —CH$_2$OCH$_3$ and —CH$_2$OCH$_2$CH$_3$; R2 is hydrogen; R3 is selected from the group consisting of —CH$_2$(CH$_2$)$_7$CH$_3$, —CH$_2$(CH$_2$)$_9$CH$_3$, —CH$_2$(CH$_2$)$_{11}$CH$_3$, and —CH$_2$(CH$_2$)$_{13}$CH$_3$; R4 is hydrogen; and n is 0.

In some embodiments of Formula I, X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_7$CH$_3$; R4 is hydrogen; and n is 0.

In some embodiments of Formula I, X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_9$CH$_3$; R4 is hydrogen; and n is 0.

In some embodiments of Formula I, X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_{11}$CH$_3$; R4 is hydrogen; and n is 0.

In some embodiments of Formula I, X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_{13}$CH$_3$; R4 is hydrogen; and n is 0.

In some embodiments of Formula I, X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_{15}$CH$_3$; R4 is hydrogen; and n is 0.

In some embodiments of Formula I, the compound is present in the form of a salt. The salt is typically a pharmaceutically acceptable salt. Most commonly the salt is a hydrochloride or dihydrochloride salt.

In some embodiments, the compound of Formula I has an enantiomeric purity of at least 80% enantiomeric excess (80% ee). In some embodiments, the compound of Formula I has an enantiomeric purity of at least 90% enantiomeric excess (90% ee). In some embodiments, the compound of Formula I has an enantiomeric purity of at least 95% enantiomeric excess (95% ee). In some embodiments, the compound of Formula I has an enantiomeric purity of at least 97% enantiomeric excess (97% ee). In some embodiments, the compound of Formula I has an enantiomeric purity of at least 98% enantiomeric excess (98% ee). In some embodiments, the compound of Formula I has an enantiomeric purity of at least 99% enantiomeric excess (99% ee). In some embodiments, the compound of Formula I has an enantiomeric purity of at least 99.5% enantiomeric excess (99.5% ee). In some embodiments, the compound of Formula I has an enantiomeric purity of at least 99.8% enantiomeric excess (99.8% ee).

In preferred embodiments, the compound of Formula I has an enantiomeric purity of at least 95% ee, at least 97% ee, or at least 98% ee.

The compounds of Formulas II, III, IV, and V described below are useful as intermediate compounds for the preparation of compounds of Formula I.

This disclosure provides intermediate compounds of the following Formula II:

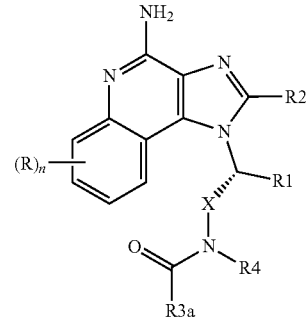

Formula II wherein R, R1, R2, R4, X, and n are as defined above for Formula I; R3a is selected from the group consisting of —OC(CH$_3$)$_3$, —OCH$_2$Ph, and —OCH$_2$-(9-fluorenyl); and pharmaceutically acceptable salts thereof.

In some embodiments of Formula II, X is selected from the group consisting of —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

In some embodiments of Formula II, X is —CH$_2$CH$_2$CH$_2$—.

In some embodiments of Formula II, X is alkylene optionally interrupted by one or more —O— groups; R1 is selected from the group consisting of C$_{1-5}$alkyl and —C$_{1-3}$alkylene-O—C$_{1-3}$alkyl; R2 is selected from the group consisting of hydrogen, methyl, and ethyl; R3a is —OC(CH$_3$)$_3$; R4 is hydrogen; and n is 0.

In some embodiments of Formula II, X is C$_{2-5}$alkylene; R1 is selected from the group consisting of —CH$_2$OCH$_3$ and —CH$_2$OCH$_2$CH$_3$; R2 is selected from the group consisting of hydrogen, methyl, and ethyl; R3a is —OC(CH$_3$)$_3$; R4 is hydrogen; and n is 0.

In some embodiments of Formula II, X is C$_{2-5}$alkylene; R1 is selected from the group consisting of —CH$_2$OCH$_3$ and —CH$_2$OCH$_2$CH$_3$; R2 is hydrogen; R3a is —OC(CH$_3$)$_3$; R4 is hydrogen; and n is 0.

In some embodiments of Formula II, X is selected from the group consisting of —CH$_2$CH$_2$CH$_2$—, —CH$_2$CH$_2$CH$_2$CH$_2$—, and —CH$_2$CH$_2$CH$_2$CH$_2$—; R1 is selected from the group consisting of —CH$_2$OCH$_3$ and —CH$_2$OCH$_2$CH$_3$; R2 is selected from the group consisting of hydrogen, methyl, and ethyl; R3a is —OC(CH$_3$)$_3$; R4 is hydrogen; and n is 0.

In some embodiments of Formula II, X is —CH$_2$CH$_2$CH$_2$—; R1 is selected from the group consisting of —CH$_2$OCH$_3$ and —CH$_2$OCH$_2$CH$_3$; R2 is hydrogen; R3a is —OC(CH$_3$)$_3$; R4 is hydrogen; and n is 0.

In some embodiments of Formula II, the compound is present in the form of a salt. The salt is typically a pharmaceutically acceptable salt. Most commonly the salt is a hydrochloride or dihydrochloride salt.

This disclosure provides intermediate compounds of the following Formula III:

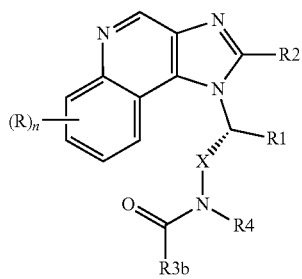

Formula III wherein R, R1, R2, R4, X, and n are as defined above for Formulas I and II; R3b is selected from the group consisting of alkyl, —OC(CH$_3$)$_3$, —OCH$_2$Ph, and —OCH$_2$-(9-fluorenyl); and pharmaceutically acceptable salts thereof.

In some embodiments of Formula III, X is selected from the group consisting of —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

In some embodiments of Formula III, R3b is —C$_{1-10}$alkyl.

In some embodiments of Formula III, R3b is —C$_{10-20}$alkyl.

In some embodiments of Formula III, X is —CH$_2$CH$_2$CH$_2$—.

In some embodiments of Formula III, X is alkylene optionally interrupted by one or more —O— groups; R1 is selected from the group consisting of C$_{1-5}$alkyl and —C$_{1-3}$alkylene-O—C$_{1-3}$alkyl; R2 is selected from the group consisting of hydrogen, methyl, and ethyl; R3b is alkyl or —OC(CH$_3$)$_3$; R4 is hydrogen; and n is 0.

In some embodiments of Formula III, X is C$_{2-5}$alkylene; R1 is selected from the group consisting of —CH$_2$OCH$_3$ and —CH$_2$OCH$_2$CH$_3$; R2 is selected from the group consisting of hydrogen, methyl, and ethyl; R3b is —OC(CH$_3$)$_3$; R4 is hydrogen; and n is 0.

In some embodiments of Formula III, X is C$_{2-5}$alkylene; R1 is selected from the group consisting of —CH$_2$OCH$_3$ and —CH$_2$OCH$_2$CH$_3$; R2 is hydrogen; R3b is —OC(CH$_3$)$_3$; R4 is hydrogen; and n is 0.

In some embodiments of Formula III, X is selected from the group consisting of —CH$_2$CH$_2$CH$_2$—, —CH$_2$CH$_2$CH$_2$CH$_2$—, and —CH$_2$CH$_2$CH$_2$CH$_2$—; R1 is selected from the group consisting of —CH$_2$OCH$_3$ and —CH$_2$OCH$_2$CH$_3$; R2 is selected from the group consisting of hydrogen, methyl, and ethyl; R3b is —OC(CH$_3$)$_3$; R4 is hydrogen; and n is 0.

In some embodiments of Formula III, X is —CH$_2$CH$_2$CH$_2$—; R1 is selected from the group consisting of —CH$_2$OCH$_3$, —CH$_2$OCH$_2$CH$_3$; R2 is hydrogen; R3b is —OC(CH$_3$)$_3$; R4 is hydrogen; and n is 0.

In some embodiments of Formula III, the compound is present in the form of a salt. The salt is typically a pharmaceutically acceptable salt. Most commonly the salt is a hydrochloride or dihydrochloride salt.

This disclosure provides intermediate compounds of the following Formula IV:

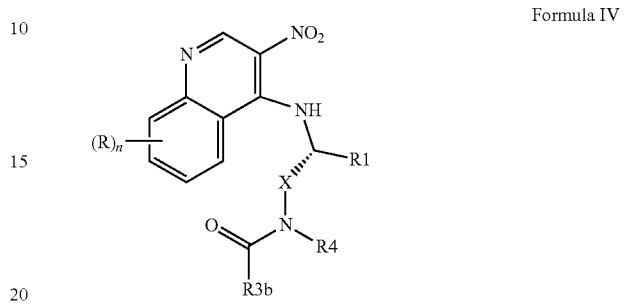

Formula IV wherein R, R1, R4, X, R3b and n are as defined above for Formulas I and III; and pharmaceutically acceptable salts thereof.

In some embodiments of Formula IV, X is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$—.

In some embodiments of Formula IV, X is —CH$_2$CH$_2$CH$_2$—.

In some embodiments of Formula IV, R3b is —C$_{1-10}$alkyl.

In some embodiments of Formula IV, R3b is —C$_{10-20}$alkyl.

In some embodiments of Formula IV, X is alkylene optionally interrupted by one or more —O— groups; R1 is selected from the group consisting of C$_{1-5}$alkyl and —C$_{1-3}$alkylene-O—C$_{1-3}$alkyl; R3b is alkyl or —OC(CH$_3$)$_3$; R4 is hydrogen; and n is 0.

In some embodiments of Formula IV, X is C$_{2-5}$alkylene; R1 is selected from the group consisting of —CH$_2$OCH$_3$ and —CH$_2$OCH$_2$CH$_3$; R3b is —OC(CH$_3$)$_3$; R4 is hydrogen; and n is 0.

In some embodiments of Formula IV, X is C$_{2-5}$alkylene; R1 is selected from the group consisting of —CH$_2$OCH$_3$ and —CH$_2$OCH$_2$CH$_3$; R3b is —OC(CH$_3$)$_3$; R4 is hydrogen; and n is 0.

In some embodiments of Formula IV, X is selected from the group consisting of —CH$_2$CH$_2$CH$_2$—, —CH$_2$CH$_2$CH$_2$CH$_2$—, and —CH$_2$CH$_2$CH$_2$CH$_2$—; R1 is selected from the group consisting of —CH$_2$OCH$_3$ and —CH$_2$OCH$_2$CH$_3$; R3b is —OC(CH$_3$)$_3$; R4 is hydrogen; and n is 0.

In some embodiments of Formula IV, X is —CH$_2$CH$_2$CH$_2$—; R1 is selected from the group consisting of —CH$_2$OCH$_3$ and —CH$_2$OCH$_2$CH$_3$; R3b is —OC(CH$_3$)$_3$; R4 is hydrogen; and n is 0.

In some embodiments of Formula IV, the compound is present in the form of a salt. The salt is typically a pharmaceutically acceptable salt. Most commonly the salt is a hydrochloride or dihydrochloride salt.

This disclosure provides intermediate compounds of the following Formula V:

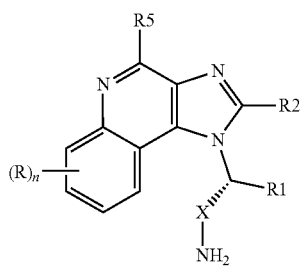

Formula V wherein R, R1, R2, X, and n are as defined above for Formulas I and II; R5 is hydrogen or —NH$_2$; and pharmaceutically acceptable salts thereof.

In some embodiments of Formula V, X is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—.

In some embodiments of Formula V, X is —CH$_2$CH$_2$CH$_2$—.

In some embodiments of Formula V, X is alkylene optionally interrupted by one or more —O— groups; R1 is selected from the group consisting of C$_{1-5}$alkyl and —C$_{1-3}$alkylene-O—C$_{1-3}$alkyl; R2 is selected from the group consisting of hydrogen, methyl, and ethyl; R5 hydrogen or —NH$_2$; and n is 0.

In some embodiments of Formula V, X is C$_{2-5}$alkylene; R1 is selected from the group consisting of —CH$_2$OCH$_3$ and —CH$_2$OCH$_2$CH$_3$; R2 is selected from the group consisting of hydrogen, methyl, and ethyl; R5 hydrogen or —NH$_2$; and n is 0.

In some embodiments of Formula V, X is C$_{2-5}$alkylene; R1 is selected from the group consisting of —CH$_2$OCH$_3$ and —CH$_2$OCH$_2$CH$_3$; R2 is hydrogen; R5 hydrogen or —NH$_2$; and n is 0.

In some embodiments of Formula V, X is selected from the group consisting of —CH$_2$CH$_2$CH$_2$—, —CH$_2$CH$_2$CH$_2$CH$_2$—, and —CH$_2$CH$_2$CH$_2$CH$_2$—; R1 is selected from the group consisting of —CH$_2$OCH$_3$ and —CH$_2$OCH$_2$CH$_3$; R2 is selected from the group consisting of hydrogen, methyl, and ethyl; R5 hydrogen or —NH$_2$; and n is 0.

In some embodiments of Formula V, X is —CH$_2$CH$_2$CH$_2$—; R1 is selected from the group consisting of —CH$_2$OCH$_3$ and —CH$_2$OCH$_2$CH$_3$; R2 is hydrogen; R5 hydrogen or —NH$_2$; and n is 0.

In some embodiments of Formula V, the compound is present in the form of a salt. The salt is typically a pharmaceutically acceptable salt. Most commonly the salt is a hydrochloride or dihydrochloride salt.

In some embodiments, the compound selected from Formulas II-V has an enantiomeric purity of at least 80% enantiomeric excess (80% ee). In some embodiments, the compound selected from Formulas II-V has an enantiomeric purity of at least 90% enantiomeric excess (90% ee). In some embodiments, the compound selected from Formulas II-V has an enantiomeric purity of at least 95% enantiomeric excess (95% ee). In some embodiments, the compound selected from Formulas II-V an enantiomeric purity of at least 97% enantiomeric excess (97% ee). In some embodiments, the compound selected from Formulas II-V has an enantiomeric purity of at least 98% enantiomeric excess (98% ee). In some embodiments, the compound selected from Formulas II-V has an enantiomeric purity of at least 99% enantiomeric excess (99% ee). In some embodiments, the compound selected from Formulas II-V has an enantiomeric purity of at least 99.5% enantiomeric excess (99.5% ee). In some embodiments, the compound selected from Formulas II-V has an enantiomeric purity of at least 99.8% enantiomeric excess (99.8% ee).

This disclosure provides compounds of the following Formula VI:

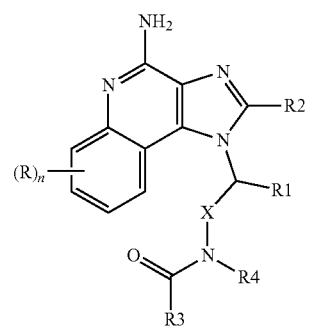

Formula VI wherein R, R1, R2, R3, R4, X, and n are as defined above for Formula I; and pharmaceutically acceptable salts thereof.

In some embodiments of Formula VI, n is 0.

In some embodiments of Formula VI, R is selected from the group consisting of halogen, hydroxy, C$_1$-7 alkoxy, and —C(O)—O—C$_{1-5}$alkyl.

In some embodiments of Formula VI, R is selected from the group consisting of halogen and hydroxy.

In some embodiments of Formula VI, R is a halogen.

In some embodiments of Formula VI, R is selected from the group consisting of hydroxy, F, and Cl.

In some embodiments of Formula VI, R1 is —C$_{1-3}$alkylene-O—C$_{1-3}$alkyl.

In some embodiments of Formula VI, R1 is selected from the group consisting of —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$OCH$_3$, —CH$_2$OCH$_2$CH$_3$, and —CH$_2$CH$_2$OCH$_3$.

In some embodiments of Formula VI, R1 is selected from the group consisting of —CH$_2$OCH$_3$, —CH$_2$OCH$_2$CH$_3$, and —CH$_2$CH$_2$OCH$_3$.

In some embodiments of Formula VI, R1 is selected from the group consisting of —CH$_2$OCH$_3$, —CH$_2$OCH$_2$CH$_3$.

In some embodiments of Formula VI, R2 is selected from the group consisting of hydrogen, methyl, and ethyl.

In some embodiments of Formula VI, R2 is hydrogen.

In some embodiments of Formula VI, R2 is selected from the group consisting of hydrogen, —CH$_3$, —CH$_2$CH$_3$, —CH$_2$CH$_2$CH$_3$, —CH$_2$CH$_2$CH$_2$CH$_3$.

In some embodiments of Formula VI, R3 is C$_{1-19}$alkyl.
In some embodiments of Formula VI, R3 is C$_{1-4}$alkyl.
In some embodiments of Formula VI, R3 is C$_{5-17}$alkyl.
In some embodiments of Formula VI, R3 is C$_{7-19}$alkyl.
In some embodiments of Formula VI, R3 is C$_{7-17}$alkyl.
In some embodiments of Formula VI, R3 is C$_{9-19}$alkyl.
In some embodiments of Formula VI, R3 is C$_{9-17}$alkyl.
In some embodiments of Formula VI, R3 is C$_{11-17}$alkyl.
In some embodiments of Formula VI, R3 is C$_{11-15}$alkyl.
In some embodiments of Formula VI, R3 is C$_{7-11}$alkyl.
In some embodiments of Formula VI, R3 is C$_{19}$alkyl.
In some embodiments of Formula VI, R3 is C$_{17}$alkyl.
In some embodiments of Formula VI, R3 is C$_{15}$alkyl.
In some embodiments of Formula VI, R3 is C$_{13}$alkyl.

In some embodiments of Formula VI, R3 is $C_{11}$alkyl.

In some embodiments of Formula VI, R3 is $-(CH_2)_{4-18}CH_3$.

In some embodiments of Formula VI, R3 is $-(CH_2)_{6-16}CH_3$.

In some embodiments of Formula VI, R3 is $-(CH_2)_{8-16}CH_3$.

In some embodiments of Formula VI, R3 is $-(CH_2)_{10-16}CH_3$.

In some embodiments of Formula VI, R3 is selected from the group consisting of $-CH_3$, $-CH_2CH_3$, $-CH_2CH_2CH_3$, $-CH(CH_3)_2$, $-CH_2(CH_2)_2CH_3$, $-CH_2CH_2(CH_3)_2$, $-CH_2(CH_2)_3CH_3$, $-CH_2(CH_2)_4CH_3$, $-CH_2(CH_2)_5CH_3$, $-CH_2(CH_2)_6CH_3$, $-CH_2(CH_2)_7CH_3$, $-CH_2(CH_2)_8CH_3$, $-CH_2(CH_2)_9CH_3$, $-CH_2(CH_2)_{10}CH_3$, $-CH_2(CH_2)_{11}CH_3$, $-CH_2(CH_2)_{12}CH_3$, $-CH_2(CH_2)_{13}CH_3$, $-CH_2(CH_2)_{14}CH_3$, $-CH_2(CH_2)_{15}CH_3$, $-CH_2(CH_2)_{16}CH_3$, and $-CH_2(CH_2)_{17}CH_3$.

In some embodiments of Formula VI, R3 is selected from the group consisting of $-CH_3$, $-CH_2CH_3$, $-CH_2CH_2CH_3$, $-CH(CH_3)_2$, $-CH_2(CH_2)_2CH_3$, $-CH_2CH_2(CH_3)_2$, $-CH_2(CH_2)_3CH_3$, and $-CH_2(CH_2)_4CH_3$.

In some embodiments of Formula VI, R3 is selected from the group consisting of $-CH_2(CH_2)_5CH_3$, $-CH_2(CH_2)_7CH_3$, $-CH_2(CH_2)_9CH_3$, $-CH_2(CH_2)_{11}CH_3$, $-CH_2(CH_2)_{13}CH_3$, $-CH_2(CH_2)_{15}CH_3$, and $-CH_2(CH_2)_{17}CH_3$.

In some embodiments of Formula VI, R3 is selected from the group consisting of $-CH_2(CH_2)_9CH_3$, $-CH_2(CH_2)_{11}CH_3$, and $-CH_2(CH_2)_{13}CH_3$.

In some embodiments of Formula VI, R3 is $-CH_2(CH_2)_7CH_3$.

In some embodiments of Formula VI, R3 is $-CH_2(CH_2)_9CH_3$.

In some embodiments of Formula VI, R3 is $-CH_2(CH_2)_{11}CH_3$.

In some embodiments of Formula VI, R3 is $-CH_2(CH_2)_{13}CH_3$.

In some embodiments of Formula VI, R3 is selected from the group consisting of $-CH_2CH_2-O-(CH_2)_{1-16}CH_3$, $-CH_2CH_2CH_2-O-(CH_2)_{1-15}CH_3$, $-CH_2(CH_2)_2CH_2-O-(CH_2)_{1-14}CH_3$, $-CH_2(CH_2)_3CH_2-O-(CH_2)_{1-13}CH_3$, $-CH_2(CH_2)_4CH_2-O-(CH_2)_{1-12}CH_3$, $-CH_2(CH_2)_5CH_2-O-(CH_2)_{1-11}CH_3$, $-CH_2(CH_2)_6CH_2-O-(CH_2)_{1-10}CH_3$, $-CH_2(CH_2)_7CH_2-O-(CH_2)_{1-9}CH_3$, $-CH_2(CH_2)_8CH_2-O-(CH_2)_{1-8}CH_3$, $-CH_2(CH_2)_9CH_2-O-(CH_2)_{1-7}CH_3$, $-CH_2(CH_2)_{10}CH_2-O-(CH_2)_{1-6}CH_3$, $-CH_2(CH_2)_{11}CH_2-O-(CH_2)_{1-5}CH_3$, $-CH_2(CH_2)_{12}CH_2-O-(CH_2)_{1-4}CH_3$, $-CH_2(CH_2)_{13}CH_2-O-(CH_2)_{1-3}CH_3$, $-CH_2(CH_2)_{14}CH_2-O-(CH_2)_{1-2}CH_3$, $-CH_2(CH_2)_{15}CH_2-O-CH_2CH_3$, $-CH_2(CH_2)_{1-17}-OCH_3$.

In some embodiments of Formula VI, R4 is selected from the group consisting of hydrogen and methyl.

In some embodiments of Formula VI, R4 is hydrogen.

In some embodiments of Formula VI, X is alkylene.

In some embodiments of Formula VI, X is a $C_{1-5}$alkylene optionally interrupted by one or more $-O-$ groups.

In some embodiments of Formula VI, X is $C_{1-5}$alkylene.

In some embodiments of Formula VI, X is $C_{2-6}$alkylene.

In some embodiments of Formula VI, X is $C_{2-5}$alkylene.

In some embodiments of Formula VI, X is a $C_{2-4}$alkylene.

In some embodiments of Formula VI, X is selected from the group consisting of $-CH_2-$, $-CH_2CH_2-$, $-CH_2CH_2CH_2-$, $-CH_2CH_2CH_2CH_2-$, $-CH_2CH_2CH_2CH_2CH_2-$, $-CH_2CH_2CH_2CH_2CH_2CH_2-$, $-CH_2CH_2-O-CH_2CH_2-$, and $-CH_2CH_2-O-CH_2CH_2CH_2-$.

In some embodiments of Formula VI, X is selected from the group consisting of $-CH_2-$, $-CH_2CH_2-$, $-CH_2CH_2CH_2-$, $-CH_2CH_2CH_2CH_2-$, and $-CH_2CH_2CH_2CH_2CH_2-$.

In some embodiments of Formula VI, X is $-CH_2CH_2CH_2-$.

In some embodiments of Formula VI, X is alkylene optionally interrupted by one or more $-O-$ groups; R1 is selected from the group consisting of $C_{1-5}$alkyl and $-C_{1-3}$alkylene-O-$C_{1-3}$alkyl; R2 is selected from the group consisting of hydrogen, methyl, and ethyl; R3 is $C_{7-17}$alkyl; R4 is hydrogen; and n is 0.

In some embodiments of Formula VI, X is $C_{2-5}$alkylene; R1 is selected from the group consisting of $-CH_2OCH_3$ and $-CH_2OCH_2CH_3$; R2 is selected from the group consisting of hydrogen, methyl, and ethyl; R3 is $C_{7-17}$alkyl; R4 is hydrogen; and n is 0.

In some embodiments of Formula VI, X is $C_{2-5}$alkylene; R1 is selected from the group consisting of $-CH_2OCH_3$ and $-CH_2OCH_2CH_3$; R2 is hydrogen; R3 is $C_{7-17}$alkyl; R4 is hydrogen; and n is 0.

In some embodiments of Formula VI, X is selected from the group consisting of $-CH_2CH_2CH_2-$, $-CH_2CH_2CH_2CH_2-$, and $-CH_2CH_2CH_2CH_2-$; R1 is selected from the group consisting of $-CH_2OCH_3$ and $-CH_2OCH_2CH_3$; R2 is selected from the group consisting of hydrogen, methyl, and ethyl; R3 is $C_{7-17}$alkyl; R4 is hydrogen; and n is 0.

In some embodiments of Formula VI, X is $-CH_2CH_2CH_2-$; R1 is selected from the group consisting of $-CH_2OCH_3$ and $-CH_2OCH_2CH_3$; R2 is hydrogen; R3 is $C_{7-17}$alkyl; R4 is hydrogen; and n is 0.

In some embodiments of Formula VI, X is $-CH_2CH_2CH_2-$; R1 is selected from the group consisting of $-CH_2OCH_3$ and $-CH_2OCH_2CH_3$; R2 is hydrogen; R3 is $C_{9-15}$alkyl; R4 is hydrogen; and n is 0.

In some embodiments of Formula VI, X is $-CH_2CH_2CH_2-$; R1 is selected from the group consisting of $-CH_2OCH_3$ and $-CH_2OCH_2CH_3$; R2 is hydrogen; R3 is $C_{11-15}$alkyl; R4 is hydrogen; and n is 0.

In some embodiments of Formula VI, X is $-CH_2CH_2CH_2-$; R1 is selected from the group consisting of $-CH_2OCH_3$ and $-CH_2OCH_2CH_3$; R2 is hydrogen; R3 is selected from the group consisting of $-CH_2(CH_2)_7CH_3$, $-CH_2(CH_2)_9CH_3$, $-CH_2(CH_2)_{11}CH_3$, and $-CH_2(CH_2)_{13}CH_3$; R4 is hydrogen; and n is 0.

In some embodiments of Formula VI, X is $-CH_2CH_2CH_2-$; R1 is selected from the group consisting of $-CH_2OCH_3$ and $-CH_2OCH_2CH_3$; R2 is hydrogen; R3 is $-CH_2(CH_2)_7CH_3$; R4 is hydrogen; and n is 0.

In some embodiments of Formula VI, X is $-CH_2CH_2CH_2-$; R1 is selected from the group consisting of $-CH_2OCH_3$ and $-CH_2OCH_2CH_3$; R2 is hydrogen; R3 is $-CH_2(CH_2)_9CH_3$; R4 is hydrogen; and n is 0.

In some embodiments of Formula VI, X is $-CH_2CH_2CH_2-$; R1 is selected from the group consisting of $-CH_2OCH_3$ and $-CH_2OCH_2CH_3$; R2 is hydrogen; R3 is $-CH_2(CH_2)_{11}CH_3$; R4 is hydrogen; and n is 0.

In some embodiments of Formula VI, X is $-CH_2CH_2CH_2-$; R1 is selected from the group consisting of $-CH_2OCH_3$ and $-CH_2OCH_2CH_3$; R2 is hydrogen; R3 is $-CH_2(CH_2)_{13}CH_3$; R4 is hydrogen; and n is 0.

In some embodiments of Formula VI, X is $-CH_2CH_2CH_2-$; R1 is selected from the group consisting of —CH$_2$OCH$_3$ and —CH$_2$OCH$_2$CH$_3$; R2 is hydrogen; R3 is —CH$_2$(CH$_2$)$_{15}$CH$_3$; R4 is hydrogen; and n is 0.

In some embodiments of Formula VI, the compound is present in the form of a salt. The salt is typically a pharmaceutically acceptable salt. Most commonly the salt is a hydrochloride or dihydrochloride salt.

For the compounds of Formulas I, II, III, V, and VI, the substituent R is preferably attached at either C-7 or C-8 of the imidazo[4,5-c]quinoline ring. The R substituent is most preferably attached at C-7 of the imidazo[4,5-c]quinoline ring. The numbering for the imidazo[4,5-c]quinoline ring is shown in Figure A.

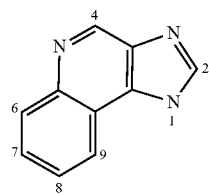

Figure A

Exemplary compounds of Formula I or Formula VI are presented in Tables 1-24. In Tables 1-24, each row represents a specific compound with n, R1, R2, R3, R4, and X defined.

TABLE 1

| n | R1 | R2 | R3 | R4 | X |
|---|---|---|---|---|---|
| 0 | —CH$_2$OCH$_3$ | H | —(CH$_2$)$_4$CH$_3$ | H | —CH$_2$— |
| 0 | —CH$_2$OCH$_3$ | H | —(CH$_2$)$_5$CH$_3$ | H | —CH$_2$— |
| 0 | —CH$_2$OCH$_3$ | H | —(CH$_2$)$_6$CH$_3$ | H | —CH$_2$— |
| 0 | —CH$_2$OCH$_3$ | H | —(CH$_2$)$_7$CH$_3$ | H | —CH$_2$— |
| 0 | —CH$_2$OCH$_3$ | H | —(CH$_2$)$_8$CH$_3$ | H | —CH$_2$— |
| 0 | —CH$_2$OCH$_3$ | H | —(CH$_2$)$_{10}$CH$_3$ | H | —CH$_2$— |
| 0 | —CH$_2$OCH$_3$ | H | —(CH$_2$)$_{12}$CH$_3$ | H | —CH$_2$— |
| 0 | —CH$_2$OCH$_3$ | H | —(CH$_2$)$_{14}$CH$_3$ | H | —CH$_2$— |
| 0 | —CH$_2$OCH$_3$ | H | —(CH$_2$)$_{16}$CH$_3$ | H | —CH$_2$— |
| 0 | —CH$_2$OCH$_3$ | H | —(CH$_2$)$_{18}$CH$_3$ | H | —CH$_2$— |

TABLE 2

| n | R1 | R2 | R3 | R4 | X |
|---|---|---|---|---|---|
| 0 | —CH$_2$OCH$_3$ | H | —(CH$_2$)$_4$CH$_3$ | H | —(CH$_2$)$_2$— |
| 0 | —CH$_2$OCH$_3$ | H | —(CH$_2$)$_5$CH$_3$ | H | —(CH$_2$)$_2$— |
| 0 | —CH$_2$OCH$_3$ | H | —(CH$_2$)$_6$CH$_3$ | H | —(CH$_2$)$_2$— |
| 0 | —CH$_2$OCH$_3$ | H | —(CH$_2$)$_7$CH$_3$ | H | —(CH$_2$)$_2$— |
| 0 | —CH$_2$OCH$_3$ | H | —(CH$_2$)$_8$CH$_3$ | H | —(CH$_2$)$_2$— |
| 0 | —CH$_2$OCH$_3$ | H | —(CH$_2$)$_{10}$CH$_3$ | H | —(CH$_2$)$_2$— |
| 0 | —CH$_2$OCH$_3$ | H | —(CH$_2$)$_{12}$CH$_3$ | H | —(CH$_2$)$_2$— |
| 0 | —CH$_2$OCH$_3$ | H | —(CH$_2$)$_{14}$CH$_3$ | H | —(CH$_2$)$_2$— |
| 0 | —CH$_2$OCH$_3$ | H | —(CH$_2$)$_{16}$CH$_3$ | H | —(CH$_2$)$_2$— |
| 0 | —CH$_2$OCH$_3$ | H | —(CH$_2$)$_{18}$CH$_3$ | H | —(CH$_2$)$_2$— |

TABLE 3

| n | R1 | R2 | R3 | R4 | X |
|---|---|---|---|---|---|
| 0 | —CH$_2$OCH$_3$ | H | —(CH$_2$)$_4$CH$_3$ | H | —(CH$_2$)$_3$— |
| 0 | —CH$_2$OCH$_3$ | H | —(CH$_2$)$_5$CH$_3$ | H | —(CH$_2$)$_3$— |
| 0 | —CH$_2$OCH$_3$ | H | —(CH$_2$)$_6$CH$_3$ | H | —(CH$_2$)$_3$— |
| 0 | —CH$_2$OCH$_3$ | H | —(CH$_2$)$_7$CH$_3$ | H | —(CH$_2$)$_3$— |
| 0 | —CH$_2$OCH$_3$ | H | —(CH$_2$)$_8$CH$_3$ | H | —(CH$_2$)$_3$— |
| 0 | —CH$_2$OCH$_3$ | H | —(CH$_2$)$_{10}$CH$_3$ | H | —(CH$_2$)$_3$— |
| 0 | —CH$_2$OCH$_3$ | H | —(CH$_2$)$_{12}$CH$_3$ | H | —(CH$_2$)$_3$— |
| 0 | —CH$_2$OCH$_3$ | H | —(CH$_2$)$_{14}$CH$_3$ | H | —(CH$_2$)$_3$— |

TABLE 3-continued

| n | R1 | R2 | R3 | R4 | X |
|---|---|---|---|---|---|
| 0 | —CH$_2$OCH$_3$ | H | —(CH$_2$)$_{16}$CH$_3$ | H | —(CH$_2$)$_3$— |
| 0 | —CH$_2$OCH$_3$ | H | —(CH$_2$)$_{18}$CH$_3$ | H | —(CH$_2$)$_3$— |

TABLE 4

| n | R1 | R2 | R3 | R4 | X |
|---|---|---|---|---|---|
| 0 | —CH$_2$OCH$_3$ | H | —(CH$_2$)$_4$CH$_3$ | H | —(CH$_2$)$_4$— |
| 0 | —CH$_2$OCH$_3$ | H | —(CH$_2$)$_5$CH$_3$ | H | —(CH$_2$)$_4$— |
| 0 | —CH$_2$OCH$_3$ | H | —(CH$_2$)$_6$CH$_3$ | H | —(CH$_2$)$_4$— |
| 0 | —CH$_2$OCH$_3$ | H | —(CH$_2$)$_7$CH$_3$ | H | —(CH$_2$)$_4$— |
| 0 | —CH$_2$OCH$_3$ | H | —(CH$_2$)$_8$CH$_3$ | H | —(CH$_2$)$_4$— |
| 0 | —CH$_2$OCH$_3$ | H | —(CH$_2$)$_{10}$CH$_3$ | H | —(CH$_2$)$_4$— |
| 0 | —CH$_2$OCH$_3$ | H | —(CH$_2$)$_{12}$CH$_3$ | H | —(CH$_2$)$_4$— |
| 0 | —CH$_2$OCH$_3$ | H | —(CH$_2$)$_{14}$CH$_3$ | H | —(CH$_2$)$_4$— |
| 0 | —CH$_2$OCH$_3$ | H | —(CH$_2$)$_{16}$CH$_3$ | H | —(CH$_2$)$_4$— |
| 0 | —CH$_2$OCH$_3$ | H | —(CH$_2$)$_{18}$CH$_3$ | H | —(CH$_2$)$_4$— |

TABLE 5

| n | R1 | R2 | R3 | R4 | X |
|---|---|---|---|---|---|
| 0 | —CH$_2$OCH$_2$CH$_3$ | H | —(CH$_2$)$_4$CH$_3$ | H | —CH$_2$— |
| 0 | —CH$_2$OCH$_2$CH$_3$ | H | —(CH$_2$)$_5$CH$_3$ | H | —CH$_2$— |
| 0 | —CH$_2$OCH$_2$CH$_3$ | H | —(CH$_2$)$_6$CH$_3$ | H | —CH$_2$— |
| 0 | —CH$_2$OCH$_2$CH$_3$ | H | —(CH$_2$)$_7$CH$_3$ | H | —CH$_2$— |
| 0 | —CH$_2$OCH$_2$CH$_3$ | H | —(CH$_2$)$_8$CH$_3$ | H | —CH$_2$— |
| 0 | —CH$_2$OCH$_2$CH$_3$ | H | —(CH$_2$)$_{10}$CH$_3$ | H | —CH$_2$— |
| 0 | —CH$_2$OCH$_2$CH$_3$ | H | —(CH$_2$)$_{12}$CH$_3$ | H | —CH$_2$— |
| 0 | —CH$_2$OCH$_2$CH$_3$ | H | —(CH$_2$)$_{14}$CH$_3$ | H | —CH$_2$— |
| 0 | —CH$_2$OCH$_2$CH$_3$ | H | —(CH$_2$)$_{16}$CH$_3$ | H | —CH$_2$— |
| 0 | —CH$_2$OCH$_2$CH$_3$ | H | —(CH$_2$)$_{18}$CH$_3$ | H | —CH$_2$— |

TABLE 6

| n | R1 | R2 | R3 | R4 | X |
|---|---|---|---|---|---|
| 0 | —CH$_2$OCH$_2$CH$_3$ | H | —(CH$_2$)$_4$CH$_3$ | H | —(CH$_2$)$_2$— |
| 0 | —CH$_2$OCH$_2$CH$_3$ | H | —(CH$_2$)$_5$CH$_3$ | H | —(CH$_2$)$_2$— |
| 0 | —CH$_2$OCH$_2$CH$_3$ | H | —(CH$_2$)$_6$CH$_3$ | H | —(CH$_2$)$_2$— |
| 0 | —CH$_2$OCH$_2$CH$_3$ | H | —(CH$_2$)$_7$CH$_3$ | H | —(CH$_2$)$_2$— |
| 0 | —CH$_2$OCH$_2$CH$_3$ | H | —(CH$_2$)$_8$CH$_3$ | H | —(CH$_2$)$_2$— |
| 0 | —CH$_2$OCH$_2$CH$_3$ | H | —(CH$_2$)$_{10}$CH$_3$ | H | —(CH$_2$)$_2$— |
| 0 | —CH$_2$OCH$_2$CH$_3$ | H | —(CH$_2$)$_{12}$CH$_3$ | H | —(CH$_2$)$_2$— |
| 0 | —CH$_2$OCH$_2$CH$_3$ | H | —(CH$_2$)$_{14}$CH$_3$ | H | —(CH$_2$)$_2$— |
| 0 | —CH$_2$OCH$_2$CH$_3$ | H | —(CH$_2$)$_{16}$CH$_3$ | H | —(CH$_2$)$_2$— |
| 0 | —CH$_2$OCH$_2$CH$_3$ | H | —(CH$_2$)$_{18}$CH$_3$ | H | —(CH$_2$)$_2$— |

TABLE 7

| n | R1 | R2 | R3 | R4 | X |
|---|---|---|---|---|---|
| 0 | —CH$_2$OCH$_2$CH$_3$ | H | —(CH$_2$)$_4$CH$_3$ | H | —(CH$_2$)$_3$— |
| 0 | —CH$_2$OCH$_2$CH$_3$ | H | —(CH$_2$)$_5$CH$_3$ | H | —(CH$_2$)$_3$— |
| 0 | —CH$_2$OCH$_2$CH$_3$ | H | —(CH$_2$)$_6$CH$_3$ | H | —(CH$_2$)$_3$— |
| 0 | —CH$_2$OCH$_2$CH$_3$ | H | —(CH$_2$)$_7$CH$_3$ | H | —(CH$_2$)$_3$— |
| 0 | —CH$_2$OCH$_2$CH$_3$ | H | —(CH$_2$)$_8$CH$_3$ | H | —(CH$_2$)$_3$— |
| 0 | —CH$_2$OCH$_2$CH$_3$ | H | —(CH$_2$)$_{10}$CH$_3$ | H | —(CH$_2$)$_3$— |
| 0 | —CH$_2$OCH$_2$CH$_3$ | H | —(CH$_2$)$_{12}$CH$_3$ | H | —(CH$_2$)$_3$— |
| 0 | —CH$_2$OCH$_2$CH$_3$ | H | —(CH$_2$)$_{14}$CH$_3$ | H | —(CH$_2$)$_3$— |
| 0 | —CH$_2$OCH$_2$CH$_3$ | H | —(CH$_2$)$_{16}$CH$_3$ | H | —(CH$_2$)$_3$— |
| 0 | —CH$_2$OCH$_2$CH$_3$ | H | —(CH$_2$)$_{18}$CH$_3$ | H | —(CH$_2$)$_3$— |

TABLE 8

| n | R1 | R2 | R3 | R4 | X |
|---|---|---|---|---|---|
| 0 | —$CH_2OCH_2CH_3$ | H | —$(CH_2)_4CH_3$ | H | —$(CH_2)_4$— |
| 0 | —$CH_2OCH_2CH_3$ | H | —$(CH_2)_5CH_3$ | H | —$(CH_2)_4$— |
| 0 | —$CH_2OCH_2CH_3$ | H | —$(CH_2)_6CH_3$ | H | —$(CH_2)_4$— |
| 0 | —$CH_2OCH_2CH_3$ | H | —$(CH_2)_7CH_3$ | H | —$(CH_2)_4$— |
| 0 | —$CH_2OCH_2CH_3$ | H | —$(CH_2)_8CH_3$ | H | —$(CH_2)_4$— |
| 0 | —$CH_2OCH_2CH_3$ | H | —$(CH_2)_{10}CH_3$ | H | —$(CH_2)_4$— |
| 0 | —$CH_2OCH_2CH_3$ | H | —$(CH_2)_{12}CH_3$ | H | —$(CH_2)_4$— |
| 0 | —$CH_2OCH_2CH_3$ | H | —$(CH_2)_{14}CH_3$ | H | —$(CH_2)_4$— |
| 0 | —$CH_2OCH_2CH_3$ | H | —$(CH_2)_{16}CH_3$ | H | —$(CH_2)_4$— |
| 0 | —$CH_2OCH_2CH_3$ | H | —$(CH_2)_{18}CH_3$ | H | —$(CH_2)_4$— |

TABLE 9

| n | R1 | R2 | R3 | R4 | X |
|---|---|---|---|---|---|
| 0 | —$CH_2OCH_3$ | —$CH_3$ | —$(CH_2)_4CH_3$ | H | —$CH_2$— |
| 0 | —$CH_2OCH_3$ | —$CH_3$ | —$(CH_2)_5CH_3$ | H | —$CH_2$— |
| 0 | —$CH_2OCH_3$ | —$CH_3$ | —$(CH_2)_6CH_3$ | H | —$CH_2$— |
| 0 | —$CH_2OCH_3$ | —$CH_3$ | —$(CH_2)_7CH_3$ | H | —$CH_2$— |
| 0 | —$CH_2OCH_3$ | —$CH_3$ | —$(CH_2)_8CH_3$ | H | —$CH_2$— |
| 0 | —$CH_2OCH_3$ | —$CH_3$ | —$(CH_2)_{10}CH_3$ | H | —$CH_2$— |
| 0 | —$CH_2OCH_3$ | —$CH_3$ | —$(CH_2)_{12}CH_3$ | H | —$CH_2$— |
| 0 | —$CH_2OCH_3$ | —$CH_3$ | —$(CH_2)_{14}CH_3$ | H | —$CH_2$— |
| 0 | —$CH_2OCH_3$ | —$CH_3$ | —$(CH_2)_{16}CH_3$ | H | —$CH_2$— |
| 0 | —$CH_2OCH_3$ | —$CH_3$ | —$(CH_2)_{18}CH_3$ | H | —$CH_2$— |

TABLE 10

| n | R1 | R2 | R3 | R4 | X |
|---|---|---|---|---|---|
| 0 | —$CH_2OCH_3$ | —$CH_3$ | —$(CH_2)_4CH_3$ | H | —$(CH_2)_2$— |
| 0 | —$CH_2OCH_3$ | —$CH_3$ | —$(CH_2)_5CH_3$ | H | —$(CH_2)_2$— |
| 0 | —$CH_2OCH_3$ | —$CH_3$ | —$(CH_2)_6CH_3$ | H | —$(CH_2)_2$— |
| 0 | —$CH_2OCH_3$ | —$CH_3$ | —$(CH_2)_7CH_3$ | H | —$(CH_2)_2$— |
| 0 | —$CH_2OCH_3$ | —$CH_3$ | —$(CH_2)_8CH_3$ | H | —$(CH_2)_2$— |
| 0 | —$CH_2OCH_3$ | —$CH_3$ | —$(CH_2)_{10}CH_3$ | H | —$(CH_2)_2$— |
| 0 | —$CH_2OCH_3$ | —$CH_3$ | —$(CH_2)_{12}CH_3$ | H | —$(CH_2)_2$— |
| 0 | —$CH_2OCH_3$ | —$CH_3$ | —$(CH_2)_{14}CH_3$ | H | —$(CH_2)_2$— |
| 0 | —$CH_2OCH_3$ | —$CH_3$ | —$(CH_2)_{16}CH_3$ | H | —$(CH_2)_2$— |
| 0 | —$CH_2OCH_3$ | —$CH_3$ | —$(CH_2)_{18}CH_3$ | H | —$(CH_2)_2$— |

TABLE 11

| n | R1 | R2 | R3 | R4 | X |
|---|---|---|---|---|---|
| 0 | —$CH_2OCH_3$ | —$CH_3$ | —$(CH_2)_4CH_3$ | H | —$(CH_2)_3$— |
| 0 | —$CH_2OCH_3$ | —$CH_3$ | —$(CH_2)_5CH_3$ | H | —$(CH_2)_3$— |
| 0 | —$CH_2OCH_3$ | —$CH_3$ | —$(CH_2)_6CH_3$ | H | —$(CH_2)_3$— |
| 0 | —$CH_2OCH_3$ | —$CH_3$ | —$(CH_2)_7CH_3$ | H | —$(CH_2)_3$— |
| 0 | —$CH_2OCH_3$ | —$CH_3$ | —$(CH_2)_8CH_3$ | H | —$(CH_2)_3$— |
| 0 | —$CH_2OCH_3$ | —$CH_3$ | —$(CH_2)_{10}CH_3$ | H | —$(CH_2)_3$— |
| 0 | —$CH_2OCH_3$ | —$CH_3$ | —$(CH_2)_{12}CH_3$ | H | —$(CH_2)_3$— |
| 0 | —$CH_2OCH_3$ | —$CH_3$ | —$(CH_2)_{14}CH_3$ | H | —$(CH_2)_3$— |
| 0 | —$CH_2OCH_3$ | —$CH_3$ | —$(CH_2)_{16}CH_3$ | H | —$(CH_2)_3$— |
| 0 | —$CH_2OCH_3$ | —$CH_3$ | —$(CH_2)_{18}CH_3$ | H | —$(CH_2)_3$— |

TABLE 12

| n | R1 | R2 | R3 | R4 | X |
|---|---|---|---|---|---|
| 0 | —$CH_2OCH_3$ | —$CH_3$ | —$(CH_2)_4CH_3$ | H | —$(CH_2)_4$— |
| 0 | —$CH_2OCH_3$ | —$CH_3$ | —$(CH_2)_5CH_3$ | H | —$(CH_2)_4$— |
| 0 | —$CH_2OCH_3$ | —$CH_3$ | —$(CH_2)_6CH_3$ | H | —$(CH_2)_4$— |
| 0 | —$CH_2OCH_3$ | —$CH_3$ | —$(CH_2)_7CH_3$ | H | —$(CH_2)_4$— |
| 0 | —$CH_2OCH_3$ | —$CH_3$ | —$(CH_2)_8CH_3$ | H | —$(CH_2)_4$— |
| 0 | —$CH_2OCH_3$ | —$CH_3$ | —$(CH_2)_{10}CH_3$ | H | —$(CH_2)_4$— |
| 0 | —$CH_2OCH_3$ | —$CH_3$ | —$(CH_2)_{12}CH_3$ | H | —$(CH_2)_4$— |
| 0 | —$CH_2OCH_3$ | —$CH_3$ | —$(CH_2)_{14}CH_3$ | H | —$(CH_2)_4$— |
| 0 | —$CH_2OCH_3$ | —$CH_3$ | —$(CH_2)_{16}CH_3$ | H | —$(CH_2)_4$— |
| 0 | —$CH_2OCH_3$ | —$CH_3$ | —$(CH_2)_{18}CH_3$ | H | —$(CH_2)_4$— |

TABLE 13

| n | R1 | R2 | R3 | R4 | X |
|---|---|---|---|---|---|
| 0 | —$CH_2OCH_2CH_3$ | —$CH_3$ | —$(CH_2)_4CH_3$ | H | —$CH_2$— |
| 0 | —$CH_2OCH_2CH_3$ | —$CH_3$ | —$(CH_2)_5CH_3$ | H | —$CH_2$— |
| 0 | —$CH_2OCH_2CH_3$ | —$CH_3$ | —$(CH_2)_6CH_3$ | H | —$CH_2$— |
| 0 | —$CH_2OCH_2CH_3$ | —$CH_3$ | —$(CH_2)_7CH_3$ | H | —$CH_2$— |
| 0 | —$CH_2OCH_2CH_3$ | —$CH_3$ | —$(CH_2)_8CH_3$ | H | —$CH_2$— |
| 0 | —$CH_2OCH_2CH_3$ | —$CH_3$ | —$(CH_2)_{10}CH_3$ | H | —$CH_2$— |
| 0 | —$CH_2OCH_2CH_3$ | —$CH_3$ | —$(CH_2)_{12}CH_3$ | H | —$CH_2$— |
| 0 | —$CH_2OCH_2CH_3$ | —$CH_3$ | —$(CH_2)_{14}CH_3$ | H | —$CH_2$— |
| 0 | —$CH_2OCH_2CH_3$ | —$CH_3$ | —$(CH_2)_{16}CH_3$ | H | —$CH_2$— |
| 0 | —$CH_2OCH_2CH_3$ | —$CH_3$ | —$(CH_2)_{18}CH_3$ | H | —$CH_2$— |

TABLE 14

| n | R1 | R2 | R3 | R4 | X |
|---|---|---|---|---|---|
| 0 | —$CH_2OCH_2CH_3$ | —$CH_3$ | —$(CH_2)_4CH_3$ | H | —$(CH_2)_2$— |
| 0 | —$CH_2OCH_2CH_3$ | —$CH_3$ | —$(CH_2)_5CH_3$ | H | —$(CH_2)_2$— |
| 0 | —$CH_2OCH_2CH_3$ | —$CH_3$ | —$(CH_2)_6CH_3$ | H | —$(CH_2)_2$— |
| 0 | —$CH_2OCH_2CH_3$ | —$CH_3$ | —$(CH_2)_7CH_3$ | H | —$(CH_2)_2$— |
| 0 | —$CH_2OCH_2CH_3$ | —$CH_3$ | —$(CH_2)_8CH_3$ | H | —$(CH_2)_2$— |
| 0 | —$CH_2OCH_2CH_3$ | —$CH_3$ | —$(CH_2)_{10}CH_3$ | H | —$(CH_2)_2$— |
| 0 | —$CH_2OCH_2CH_3$ | —$CH_3$ | —$(CH_2)_{12}CH_3$ | H | —$(CH_2)_2$— |
| 0 | —$CH_2OCH_2CH_3$ | —$CH_3$ | —$(CH_2)_{14}CH_3$ | H | —$(CH_2)_2$— |
| 0 | —$CH_2OCH_2CH_3$ | —$CH_3$ | —$(CH_2)_{16}CH_3$ | H | —$(CH_2)_2$— |
| 0 | —$CH_2OCH_2CH_3$ | —$CH_3$ | —$(CH_2)_{18}CH_3$ | H | —$(CH_2)_2$— |

TABLE 15

| n | R1 | R2 | R3 | R4 | X |
|---|---|---|---|---|---|
| 0 | —$CH_2OCH_2CH_3$ | —$CH_3$ | —$(CH_2)_4CH_3$ | H | —$(CH_2)_3$— |
| 0 | —$CH_2OCH_2CH_3$ | —$CH_3$ | —$(CH_2)_5CH_3$ | H | —$(CH_2)_3$— |
| 0 | —$CH_2OCH_2CH_3$ | —$CH_3$ | —$(CH_2)_6CH_3$ | H | —$(CH_2)_3$— |
| 0 | —$CH_2OCH_2CH_3$ | —$CH_3$ | —$(CH_2)_7CH_3$ | H | —$(CH_2)_3$— |
| 0 | —$CH_2OCH_2CH_3$ | —$CH_3$ | —$(CH_2)_8CH_3$ | H | —$(CH_2)_3$— |
| 0 | —$CH_2OCH_2CH_3$ | —$CH_3$ | —$(CH_2)_{10}CH_3$ | H | —$(CH_2)_3$— |
| 0 | —$CH_2OCH_2CH_3$ | —$CH_3$ | —$(CH_2)_{12}CH_3$ | H | —$(CH_2)_3$— |
| 0 | —$CH_2OCH_2CH_3$ | —$CH_3$ | —$(CH_2)_{14}CH_3$ | H | —$(CH_2)_3$— |
| 0 | —$CH_2OCH_2CH_3$ | —$CH_3$ | —$(CH_2)_{16}CH_3$ | H | —$(CH_2)_3$— |
| 0 | —$CH_2OCH_2CH_3$ | —$CH_3$ | —$(CH_2)_{18}CH_3$ | H | —$(CH_2)_3$— |

TABLE 16

| n | R1 | R2 | R3 | R4 | X |
|---|---|---|---|---|---|
| 0 | —$CH_2OCH_2CH_3$ | —$CH_3$ | —$(CH_2)_4CH_3$ | H | —$(CH_2)_4$— |
| 0 | —$CH_2OCH_2CH_3$ | —$CH_3$ | —$(CH_2)_5CH_3$ | H | —$(CH_2)_4$— |
| 0 | —$CH_2OCH_2CH_3$ | —$CH_3$ | —$(CH_2)_6CH_3$ | H | —$(CH_2)_4$— |
| 0 | —$CH_2OCH_2CH_3$ | —$CH_3$ | —$(CH_2)_7CH_3$ | H | —$(CH_2)_4$— |
| 0 | —$CH_2OCH_2CH_3$ | —$CH_3$ | —$(CH_2)_8CH_3$ | H | —$(CH_2)_4$— |
| 0 | —$CH_2OCH_2CH_3$ | —$CH_3$ | —$(CH_2)_{10}CH_3$ | H | —$(CH_2)_4$— |
| 0 | —$CH_2OCH_2CH_3$ | —$CH_3$ | —$(CH_2)_{12}CH_3$ | H | —$(CH_2)_4$— |
| 0 | —$CH_2OCH_2CH_3$ | —$CH_3$ | —$(CH_2)_{14}CH_3$ | H | —$(CH_2)_4$— |
| 0 | —$CH_2OCH_2CH_3$ | —$CH_3$ | —$(CH_2)_{16}CH_3$ | H | —$(CH_2)_4$— |
| 0 | —$CH_2OCH_2CH_3$ | —$CH_3$ | —$(CH_2)_{18}CH_3$ | H | —$(CH_2)_4$— |

TABLE 17

| n | R1 | R2 | R3 | R4 | X |
|---|---|---|---|---|---|
| 0 | —$CH_2OCH_3$ | —$CH_2CH_3$ | —$(CH_2)_4CH_3$ | H | —$CH_2$— |
| 0 | —$CH_2OCH_3$ | —$CH_2CH_3$ | —$(CH_2)_5CH_3$ | H | —$CH_2$— |
| 0 | —$CH_2OCH_3$ | —$CH_2CH_3$ | —$(CH_2)_6CH_3$ | H | —$CH_2$— |
| 0 | —$CH_2OCH_3$ | —$CH_2CH_3$ | —$(CH_2)_7CH_3$ | H | —$CH_2$— |
| 0 | —$CH_2OCH_3$ | —$CH_2CH_3$ | —$(CH_2)_8CH_3$ | H | —$CH_2$— |
| 0 | —$CH_2OCH_3$ | —$CH_2CH_3$ | —$(CH_2)_{10}CH_3$ | H | —$CH_2$— |
| 0 | —$CH_2OCH_3$ | —$CH_2CH_3$ | —$(CH_2)_{12}CH_3$ | H | —$CH_2$— |
| 0 | —$CH_2OCH_3$ | —$CH_2CH_3$ | —$(CH_2)_{14}CH_3$ | H | —$CH_2$— |
| 0 | —$CH_2OCH_3$ | —$CH_2CH_3$ | —$(CH_2)_{16}CH_3$ | H | —$CH_2$— |
| 0 | —$CH_2OCH_3$ | —$CH_2CH_3$ | —$(CH_2)_{18}CH_3$ | H | —$CH_2$— |

TABLE 18

| n | R1 | R2 | R3 | R4 | X |
|---|---|---|---|---|---|
| 0 | —$CH_2OCH_3$ | —$CH_2CH_3$ | —$(CH_2)_4CH_3$ | H | —$(CH_2)_2$— |
| 0 | —$CH_2OCH_3$ | —$CH_2CH_3$ | —$(CH_2)_5CH_3$ | H | —$(CH_2)_2$— |
| 0 | —$CH_2OCH_3$ | —$CH_2CH_3$ | —$(CH_2)_6CH_3$ | H | —$(CH_2)_2$— |
| 0 | —$CH_2OCH_3$ | —$CH_2CH_3$ | —$(CH_2)_7CH_3$ | H | —$(CH_2)_2$— |
| 0 | —$CH_2OCH_3$ | —$CH_2CH_3$ | —$(CH_2)_8CH_3$ | H | —$(CH_2)_2$— |
| 0 | —$CH_2OCH_3$ | —$CH_2CH_3$ | —$(CH_2)_{10}CH_3$ | H | —$(CH_2)_2$— |
| 0 | —$CH_2OCH_3$ | —$CH_2CH_3$ | —$(CH_2)_{12}CH_3$ | H | —$(CH_2)_2$— |
| 0 | —$CH_2OCH_3$ | —$CH_2CH_3$ | —$(CH_2)_{14}CH_3$ | H | —$(CH_2)_2$— |
| 0 | —$CH_2OCH_3$ | —$CH_2CH_3$ | —$(CH_2)_{16}CH_3$ | H | —$(CH_2)_2$— |
| 0 | —$CH_2OCH_3$ | —$CH_2CH_3$ | —$(CH_2)_{18}CH_3$ | H | —$(CH_2)_2$— |

TABLE 19

| n | R1 | R2 | R3 | R4 | X |
|---|---|---|---|---|---|
| 0 | —$CH_2OCH_3$ | —$CH_2CH_3$ | —$(CH_2)_4CH_3$ | H | —$(CH_2)_3$— |
| 0 | —$CH_2OCH_3$ | —$CH_2CH_3$ | —$(CH_2)_5CH_3$ | H | —$(CH_2)_3$— |
| 0 | —$CH_2OCH_3$ | —$CH_2CH_3$ | —$(CH_2)_6CH_3$ | H | —$(CH_2)_3$— |
| 0 | —$CH_2OCH_3$ | —$CH_2CH_3$ | —$(CH_2)_7CH_3$ | H | —$(CH_2)_3$— |
| 0 | —$CH_2OCH_3$ | —$CH_2CH_3$ | —$(CH_2)_8CH_3$ | H | —$(CH_2)_3$— |
| 0 | —$CH_2OCH_3$ | —$CH_2CH_3$ | —$(CH_2)_{10}CH_3$ | H | —$(CH_2)_3$— |
| 0 | —$CH_2OCH_3$ | —$CH_2CH_3$ | —$(CH_2)_{12}CH_3$ | H | —$(CH_2)_3$— |
| 0 | —$CH_2OCH_3$ | —$CH_2CH_3$ | —$(CH_2)_{14}CH_3$ | H | —$(CH_2)_3$— |
| 0 | —$CH_2OCH_3$ | —$CH_2CH_3$ | —$(CH_2)_{16}CH_3$ | H | —$(CH_2)_3$— |
| 0 | —$CH_2OCH_3$ | —$CH_2CH_3$ | —$(CH_2)_{18}CH_3$ | H | —$(CH_2)_3$— |

TABLE 20

| n | R1 | R2 | R3 | R4 | X |
|---|---|---|---|---|---|
| 0 | —$CH_2OCH_3$ | —$CH_2CH_3$ | —$(CH_2)_4CH_3$ | H | —$(CH_2)_4$— |
| 0 | —$CH_2OCH_3$ | —$CH_2CH_3$ | —$(CH_2)_5CH_3$ | H | —$(CH_2)_4$— |
| 0 | —$CH_2OCH_3$ | —$CH_2CH_3$ | —$(CH_2)_6CH_3$ | H | —$(CH_2)_4$— |
| 0 | —$CH_2OCH_3$ | —$CH_2CH_3$ | —$(CH_2)_7CH_3$ | H | —$(CH_2)_4$— |
| 0 | —$CH_2OCH_3$ | —$CH_2CH_3$ | —$(CH_2)_8CH_3$ | H | —$(CH_2)_4$— |
| 0 | —$CH_2OCH_3$ | —$CH_2CH_3$ | —$(CH_2)_{10}CH_3$ | H | —$(CH_2)_4$— |
| 0 | —$CH_2OCH_3$ | —$CH_2CH_3$ | —$(CH_2)_{12}CH_3$ | H | —$(CH_2)_4$— |
| 0 | —$CH_2OCH_3$ | —$CH_2CH_3$ | —$(CH_2)_{14}CH_3$ | H | —$(CH_2)_4$— |
| 0 | —$CH_2OCH_3$ | —$CH_2CH_3$ | —$(CH_2)_{16}CH_3$ | H | —$(CH_2)_4$— |
| 0 | —$CH_2OCH_3$ | —$CH_2CH_3$ | —$(CH_2)_{18}CH_3$ | H | —$(CH_2)_4$— |

TABLE 21

| n | R1 | R2 | R3 | R4 | X |
|---|---|---|---|---|---|
| 0 | —$CH_2OCH_2CH_3$ | —$CH_2CH_3$ | —$(CH_2)_4CH_3$ | H | —$CH_2$— |
| 0 | —$CH_2OCH_2CH_3$ | —$CH_2CH_3$ | —$(CH_2)_5CH_3$ | H | —$CH_2$— |
| 0 | —$CH_2OCH_2CH_3$ | —$CH_2CH_3$ | —$(CH_2)_6CH_3$ | H | —$CH_2$— |
| 0 | —$CH_2OCH_2CH_3$ | —$CH_2CH_3$ | —$(CH_2)_7CH_3$ | H | —$CH_2$— |
| 0 | —$CH_2OCH_2CH_3$ | —$CH_2CH_3$ | —$(CH_2)_8CH_3$ | H | —$CH_2$— |
| 0 | —$CH_2OCH_2CH_3$ | —$CH_2CH_3$ | —$(CH_2)_{10}CH_3$ | H | —$CH_2$— |
| 0 | —$CH_2OCH_2CH_3$ | —$CH_2CH_3$ | —$(CH_2)_{12}CH_3$ | H | —$CH_2$— |
| 0 | —$CH_2OCH_2CH_3$ | —$CH_2CH_3$ | —$(CH_2)_{14}CH_3$ | H | —$CH_2$— |
| 0 | —$CH_2OCH_2CH_3$ | —$CH_2CH_3$ | —$(CH_2)_{16}CH_3$ | H | —$CH_2$— |
| 0 | —$CH_2OCH_2CH_3$ | —$CH_2CH_3$ | —$(CH_2)_{18}CH_3$ | H | —$CH_2$— |

TABLE 22

| n | R1 | R2 | R3 | R4 | X |
|---|---|---|---|---|---|
| 0 | —$CH_2OCH_2CH_3$ | —$CH_2CH_3$ | —$(CH_2)_4CH_3$ | H | —$(CH_2)_2$— |
| 0 | —$CH_2OCH_2CH_3$ | —$CH_2CH_3$ | —$(CH_2)_5CH_3$ | H | —$(CH_2)_2$— |
| 0 | —$CH_2OCH_2CH_3$ | —$CH_2CH_3$ | —$(CH_2)_6CH_3$ | H | —$(CH_2)_2$— |
| 0 | —$CH_2OCH_2CH_3$ | —$CH_2CH_3$ | —$(CH_2)_7CH_3$ | H | —$(CH_2)_2$— |
| 0 | —$CH_2OCH_2CH_3$ | —$CH_2CH_3$ | —$(CH_2)_8CH_3$ | H | —$(CH_2)_2$— |
| 0 | —$CH_2OCH_2CH_3$ | —$CH_2CH_3$ | —$(CH_2)_{10}CH_3$ | H | —$(CH_2)_2$— |
| 0 | —$CH_2OCH_2CH_3$ | —$CH_2CH_3$ | —$(CH_2)_{12}CH_3$ | H | —$(CH_2)_2$— |
| 0 | —$CH_2OCH_2CH_3$ | —$CH_2CH_3$ | —$(CH_2)_{14}CH_3$ | H | —$(CH_2)_2$— |
| 0 | —$CH_2OCH_2CH_3$ | —$CH_2CH_3$ | —$(CH_2)_{16}CH_3$ | H | —$(CH_2)_2$— |
| 0 | —$CH_2OCH_2CH_3$ | —$CH_2CH_3$ | —$(CH_2)_{18}CH_3$ | H | —$(CH_2)_2$— |

TABLE 23

| n | R1 | R2 | R3 | R4 | X |
|---|---|---|---|---|---|
| 0 | —$CH_2OCH_2CH_3$ | —$CH_2CH_3$ | —$(CH_2)_4CH_3$ | H | —$(CH_2)_3$— |
| 0 | —$CH_2OCH_2CH_3$ | —$CH_2CH_3$ | —$(CH_2)_5CH_3$ | H | —$(CH_2)_3$— |
| 0 | —$CH_2OCH_2CH_3$ | —$CH_2CH_3$ | —$(CH_2)_6CH_3$ | H | —$(CH_2)_3$— |
| 0 | —$CH_2OCH_2CH_3$ | —$CH_2CH_3$ | —$(CH_2)_7CH_3$ | H | —$(CH_2)_3$— |
| 0 | —$CH_2OCH_2CH_3$ | —$CH_2CH_3$ | —$(CH_2)_8CH_3$ | H | —$(CH_2)_3$— |
| 0 | —$CH_2OCH_2CH_3$ | —$CH_2CH_3$ | —$(CH_2)_{10}CH_3$ | H | —$(CH_2)_3$— |
| 0 | —$CH_2OCH_2CH_3$ | —$CH_2CH_3$ | —$(CH_2)_{12}CH_3$ | H | —$(CH_2)_3$— |
| 0 | —$CH_2OCH_2CH_3$ | —$CH_2CH_3$ | —$(CH_2)_{14}CH_3$ | H | —$(CH_2)_3$— |
| 0 | —$CH_2OCH_2CH_3$ | —$CH_2CH_3$ | —$(CH_2)_{16}CH_3$ | H | —$(CH_2)_3$— |
| 0 | —$CH_2OCH_2CH_3$ | —$CH_2CH_3$ | —$(CH_2)_{18}CH_3$ | H | —$(CH_2)_3$— |

TABLE 24

| n | R1 | R2 | R3 | R4 | X |
|---|---|---|---|---|---|
| 0 | —$CH_2OCH_2CH_3$ | —$CH_2CH_3$ | —$(CH_2)_4CH_3$ | H | —$(CH_2)_4$— |
| 0 | —$CH_2OCH_2CH_3$ | —$CH_2CH_3$ | —$(CH_2)_5CH_3$ | H | —$(CH_2)_4$— |
| 0 | —$CH_2OCH_2CH_3$ | —$CH_2CH_3$ | —$(CH_2)_6CH_3$ | H | —$(CH_2)_4$— |
| 0 | —$CH_2OCH_2CH_3$ | —$CH_2CH_3$ | —$(CH_2)_7CH_3$ | H | —$(CH_2)_4$— |
| 0 | —$CH_2OCH_2CH_3$ | —$CH_2CH_3$ | —$(CH_2)_8CH_3$ | H | —$(CH_2)_4$— |
| 0 | —$CH_2OCH_2CH_3$ | —$CH_2CH_3$ | —$(CH_2)_{10}CH_3$ | H | —$(CH_2)_4$— |
| 0 | —$CH_2OCH_2CH_3$ | —$CH_2CH_3$ | —$(CH_2)_{12}CH_3$ | H | —$(CH_2)_4$— |
| 0 | —$CH_2OCH_2CH_3$ | —$CH_2CH_3$ | —$(CH_2)_{14}CH_3$ | H | —$(CH_2)_4$— |
| 0 | —$CH_2OCH_2CH_3$ | —$CH_2CH_3$ | —$(CH_2)_{16}CH_3$ | H | —$(CH_2)_4$— |
| 0 | —$CH_2OCH_2CH_3$ | —$CH_2CH_3$ | —$(CH_2)_{18}CH_3$ | H | —$(CH_2)_4$— |

The disclosure provides a method of inducing cytokine biosynthesis in a human or animal by administering to the human or animal an effective amount of a compound or salt selected from the group consisting of any one of the above embodiments of Formula I and Formula VI.

The disclosure provides a method of inducing cytokine biosynthesis in a human or animal by administering to the human or animal an effective amount of a compound or salt selected from the group consisting of Formula I and Formula VI; wherein n is 0, R1 is —$CH_2OCH_3$ or —$CH_2OCH_2CH_3$, R2 is hydrogen, methyl, or ethyl, R3 is $C_{5-19}$alkyl, R4 is hydrogen, and X is —$CH_2CH_2CH_2$—.

The disclosure provides a method of inducing cytokine biosynthesis in a human or animal by administering to the human or animal an effective amount of a compound or salt selected from the group consisting of Formula I and Formula VI; wherein n is 0, R1 is —$CH_2OCH_3$ or —$CH_2OCH_2CH_3$, R2 is hydrogen, methyl, or ethyl, R3 is $C_{9-17}$alkyl, R4 is hydrogen, and X is —$CH_2CH_2CH_2$—.

The disclosure provides a method of inducing cytokine biosynthesis in a human or animal by administering to the human or animal an effective amount of a compound or salt selected from the group consisting of Formula I and Formula VI; wherein n is 0, R1 is —CH$_2$OCH$_2$CH$_3$, R2 is hydrogen, R3 is C$_{5-19}$alkyl, R4 is hydrogen, and X is —CH$_2$CH$_2$CH$_2$—.

The disclosure provides a method of inducing cytokine biosynthesis in a human or animal by administering to the human or animal an effective amount of a compound or salt selected from the group consisting of Formula I and Formula VI; wherein n is 0, R1 is —CH$_2$OCH$_2$CH$_3$, R2 is hydrogen, R3 is C$_{9-17}$alkyl, R4 is hydrogen, and X is —CH$_2$CH$_2$CH$_2$—.

The disclosure provides a method of inducing cytokine biosynthesis in a human or animal by administering to the human or animal an effective amount of a compound or salt selected from the group consisting of Formula I and Formula VI; wherein n is 0, R1 is —CH$_2$OCH$_2$CH$_3$, R2 is —CH$_3$, R3 is C$_{5-19}$alkyl, R4 is hydrogen, and X is —CH$_2$CH$_2$CH$_2$—.

The disclosure provides a method of inducing cytokine biosynthesis in a human or animal by administering to the human or animal an effective amount of a compound or salt selected from the group consisting of Formula I and Formula VI; wherein n is 0, R1 is —CH$_2$OCH$_2$CH$_3$, R2 is —CH$_3$, R3 is C$_{9-17}$alkyl, R4 is hydrogen, and X is —CH$_2$CH$_2$CH$_2$—.

The disclosure provides a method of inducing cytokine biosynthesis in a human or animal by administering to the human or animal an effective amount of a compound or salt selected from the group consisting of Formula I and Formula VI; wherein n is 0, R1 is —CH$_2$OCH$_2$CH$_3$, R2 is —CH$_2$CH$_3$, R3 is C$_{5-19}$alkyl, R4 is hydrogen, and X is —CH$_2$CH$_2$CH$_2$—.

The disclosure provides a method of inducing cytokine biosynthesis in a human or animal by administering to the human or animal an effective amount of a compound or salt selected from the group consisting of Formula I and Formula VI; wherein n is 0, R1 is —CH$_2$OCH$_2$CH$_3$, R2 is —CH$_2$CH$_3$, R3 is C$_{9-17}$alkyl, R4 is hydrogen, and X is —CH$_2$CH$_2$CH$_2$—.

The disclosure provides a method of inducing IFN-alpha biosynthesis in a human or animal by administering to the human or animal an effective amount of a compound or salt selected from any one of the above embodiments of Formula I and Formula VI.

The disclosure provides a method of inducing IFN-gamma biosynthesis in a human or animal by administering to the human or animal an effective amount of a compound or salt selected from any one of the above embodiments of Formula I and Formula VI.

The disclosure provides a method of inducing TNF-alpha biosynthesis in a human or animal by administering to the human or animal an effective amount of a compound or salt selected from any one of the above embodiments of Formula I and Formula VI.

The disclosure provides a method of inducing IP-10 biosynthesis in a human or animal by administering to the human or animal an effective amount of a compound or salt selected from any one of the above embodiments of Formula I and Formula VI.

The disclosure provides a method for treating a viral disease in a human or animal by administering to the human or animal an effective amount of a compound or salt selected from any one of the above embodiments of Formula I and Formula VI.

The disclosure provides a method for treating a neoplastic disease in a human or animal by administering to the human or animal an effective amount of a compound or salt selected from any one of the above embodiments of Formula I and Formula VI.

The compounds of the disclosure may be synthesized by synthetic routes that include processes analogous to those well known in the chemical arts, particularly in light of the description contained herein. The starting materials are generally available from commercial sources such as the Sigma-Aldrich Company (St. Louis, Mo.) or are readily prepared using methods well known to those of ordinary skill in the art (e.g., prepared by methods generally described in Louis F. Fieser and Mary Fieser, Reagents for Organic Synthesis, v. 1-26, Wiley, New York; Alan R Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der Organischen Chemie, 4, Aufl. Ed. Springer-Verlag, Berlin, Germany, including supplements (also available via the Beilstein online database)).

Compounds of the disclosure can be prepared, for example, according to Reaction Schemes I and II where X, R, R2, R3, and n are as described above. In step (1) of Reaction Scheme I, a suitable diaminoalkylcarboxylic acid of Formula X (such as for example (S)-2,3-diaminopropionic acid, (S)-2,4-diaminobutyric acid, L-ornithine, L-lysine, (S)-2,7-diaminoheptanoic acid, (S)-2,8-diaminooctanoic acid, etc.) can be protected with BOC and CBZ groups according to the general procedure described by Masiukiewicz, *Organic Preparations and Procedures International (OPPI)*, volume 34, 2002, pages 531-537. The compound of Formula X can be reacted with a solution of cupric acetate in water followed by a solution of di-tert-butylcarbonate (BOC-anhydride) in acetone and then 8-quinolinol. In step (2), the resulting mixture can then be sequentially reacted with a solution of N-hydroxysuccinimide, sodium carbonate, and benzyl chlorocarbonate (CBZ-Cl) to provide the compound of Formula XI. The carboxylic acid moiety of Formula XI can be reduced in step (3) to a primary alcohol (Formula XII) by reacting the compound with ethylchloroformate and a tertiary amine to form a mixed anhydride that can be subsequently reduced with NaBH$_4$. The compound of Formula XII can then be reacted in step (4) with an alkylating agent such a for example a dialkysulfate or an alkylhalide. The resulting ether of Formula XIII can be deprotected in step (5) using hydrogen and catalytic palladium on carbon to provide the CBZ deprotected compound of Formula XIV.

In Reaction Scheme II, a 4-chloro-3-nitroquinoline of Formula XV is reacted in step (6) with the compound of Formula XIV to provide a 3-nitroquinolin-4-amine of Formula XVI. The reaction can be carried out by adding the amine of Formula XIV to a solution of Formula XV in a suitable solvent such as dichloromethane in the presence of a tertiary amine such as triethylamine. Formula XVI is an embodiment of Formula IV. The 4-chloro-3-nitroquinoline compound of Formula XV and substituted analogs are known compounds (see for example, U.S. Pat. No. 3,700,674 (Diehl et al.); U.S. Pat. No. 5,389,640 (Gerster et al.); U.S. Pat. No. 6,110,929 (Gerster et al.); U.S. Pat. No. 7,923,560 (Wightman et al.), and references cited therein). In many cases, substituted analogs of Formula XV (for example n=1 and R being a halogen, alkoxy or benzyloxy group) can be prepared starting with commercially available substituted anilines.

In step (7) of Reaction Scheme II, the nitro group of Formula XVI can be reduced to an amino group. The reduction can be carried out in a pressure bottle using hydrogen, a catalytic amount of palladium or platinum on carbon, and a solvent such as methanol or acetonitrile. The reaction can be carried out with a Parr apparatus. In step (8) of Reaction Scheme II, the resulting 3,4-diamine compound can be reacted with a carboxylic acid ($R_2CO_2H$) to provide a 1H-imidazo[4,5-c]quinoline of Formula XVII. Suitable equivalents to carboxylic acids include acyl chlorides, thioesters, and 1,1-dialkoxyalkyl alkanoates. The carboxylic acid or equivalent is selected so that it will provide the desired R2 substituent in a compound of Formula XVII. For example, triethylorthoformate will provide a compound where R2 is hydrogen and trimethyl orthovalerate will provide a compound where R2 is n-butyl. The reaction can be carried out without a solvent or with an inert solvent. Optionally, a catalyst such as pyridine hydrochloride can be included. Formula XVII is an embodiment of Formula III.

In step (9) of Reaction Scheme II, the 1H-imidazo[4,5-c]quinoline of Formula XVII can be oxidized to provide a 1H-imidazo[4,5-c]quinoline-5N-oxide using a conventional oxidizing agent capable of forming an N-oxide. Preferably, a solution of the compound of Formula XVII in a suitable solvent such as chloroform or dichloromethane is reacted with 3-chloroperbenzoic acid at ambient temperature.

In step (10) of Reaction Scheme II, the N-oxide compound can be aminated to provide a 1H-imidazo[4,5-c]quinoline-4-amine of Formula XVIII. Step (10) involves reacting the N-oxide compound with an acylating agent and an aminating agent in an inert solvent such as dichloromethane or chloroform. Suitable acylating agents include alkyl- or arylsulfonyl chlorides such as benzenesulfonyl chloride, methanesulfonyl chloride, or para-toluenesulfonyl chloride. Ammonium hydroxide is a suitable aminating agent. Formula XVIII is an embodiment of Formula II.

In step (11) of Reaction Scheme II, the BOC protecting group can be removed using concentrated hydrochloric acid in ethanol with heating to provide the compound of Formula XIX. Formula XIX is an embodiment of Formula V.

In step (12) of Reaction Scheme II, the 1H-imida[4,5-c]quinoline-4-amine of Formula XIX is converted to an amide of Formula XX using conventional synthetic methods. For example, the compound of Formula XIX can be reacted with a suitable carboxylic acid chloride (R3C(O)Cl) in an inert solvent (such as dichloromethane or N,N-dimethylformamide) and a tertiary amine (such as triethylamine). The carboxylic acid chloride is selected so that it will provide the desired R3 substituent in the compound of Formula XX. Formula XX is an embodiment of Formula I.

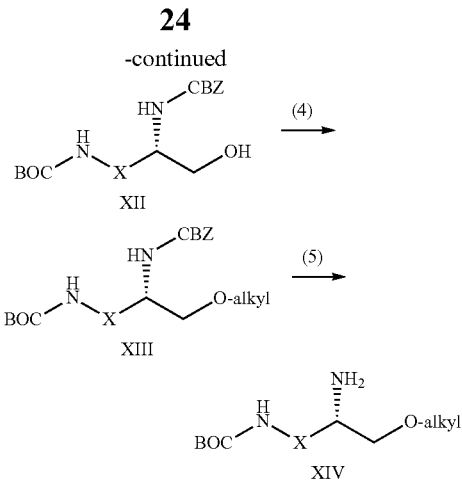

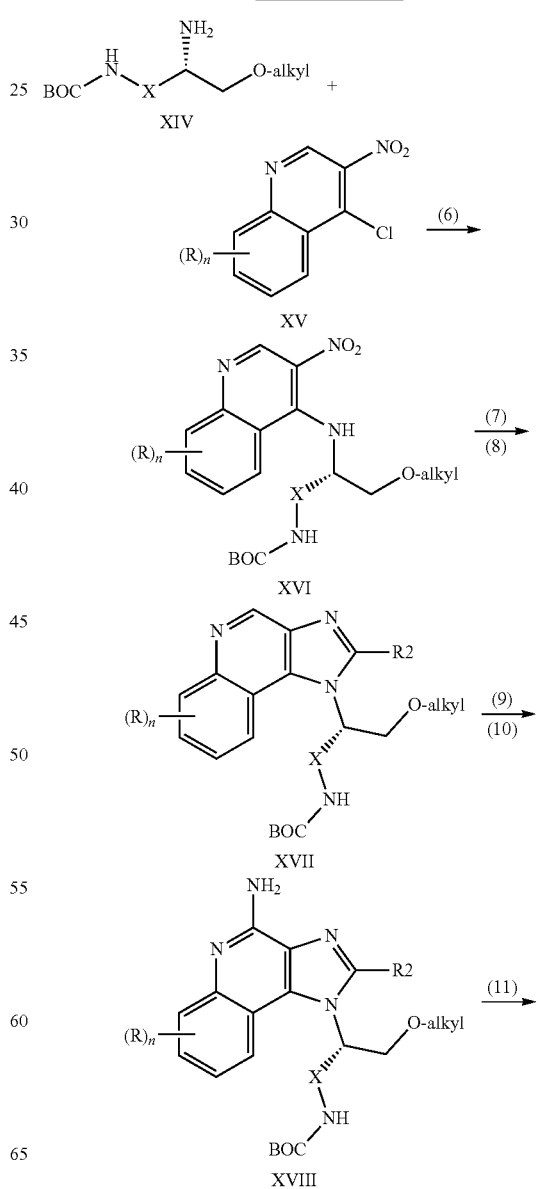

Reaction Scheme II

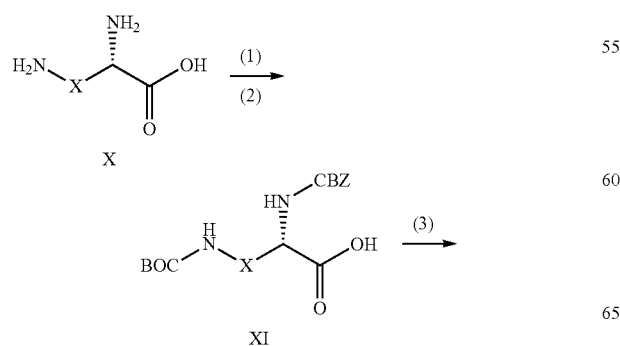

Reaction Scheme I

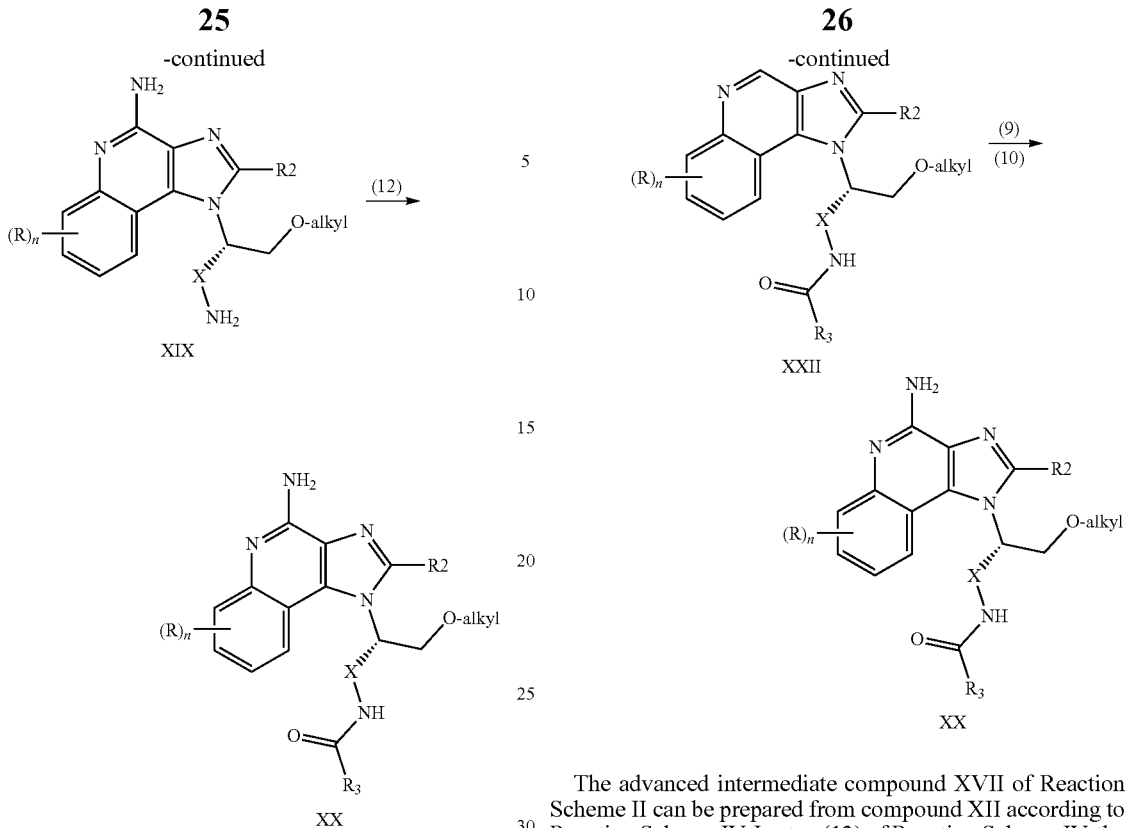

The compounds of the disclosure may also be synthesized by an alternate synthetic route in which the order of the reaction steps in Reaction Scheme II are changed as shown in Reaction Scheme III. Starting with the compound of Formula XVII, the synthetic steps (11) and (12) are performed before the synthetic steps (9) and (10). Formula XXI is an embodiment of Formula V and Formula XX is an embodiment of Formula I.

Reaction Scheme III

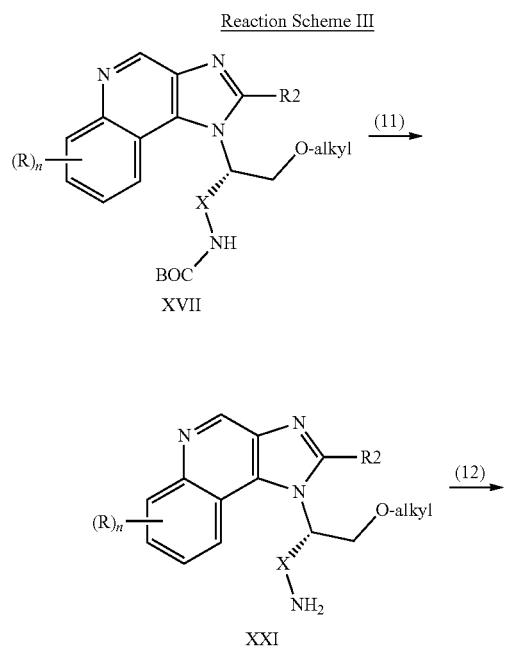

The advanced intermediate compound XVII of Reaction Scheme II can be prepared from compound XII according to Reaction Scheme IV. In step (13) of Reaction Scheme IV, the CBZ protecting group can be removed from compound XII using hydrogen and catalytic palladium on carbon to provide the compound of Formula XXIII. In Step (14) of Reaction Scheme IV, a 4-chloro-3-nitroquinoline (Formula XV) can be reacted with compound of Formula XXIII to provide a 3-nitroquinoline-4-amine of Formula XXIV. The reaction can be carried out by adding the amine of Formula XXIII to a solution of Formula XV in a suitable solvent such as dichloromethane in the presence of a tertiary amine such as triethylamine. In step (15) of Reaction Scheme IV, the nitro group of Formula XXIV is reduced to an amino group. The reaction can be carried out in a pressure bottle using hydrogen, a catalytic amount of palladium or platinum on carbon, and a solvent such as methanol or acetonitrile. The reaction can be carried out with a Parr apparatus. In step (16) of Reaction Scheme IV, the resulting 3,4-diamine substituted compound can be reacted with a carboxylic acid or carboxylic acid equivalent according to the method described for step (8) of reaction Scheme II. In step (17) of Reaction Scheme IV, the alcohol substituent of the compound of Formula XXV can be reacted with an alkylating agent such as for example a dialkylsulfate or an alkyl halide to form the compound of Formula XVII.

Reaction Scheme IV

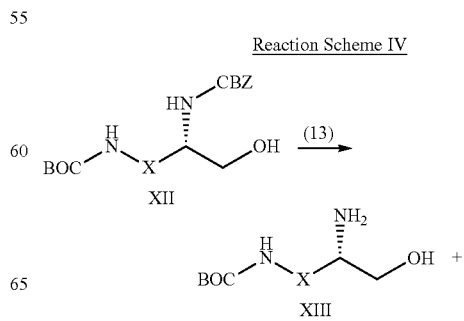

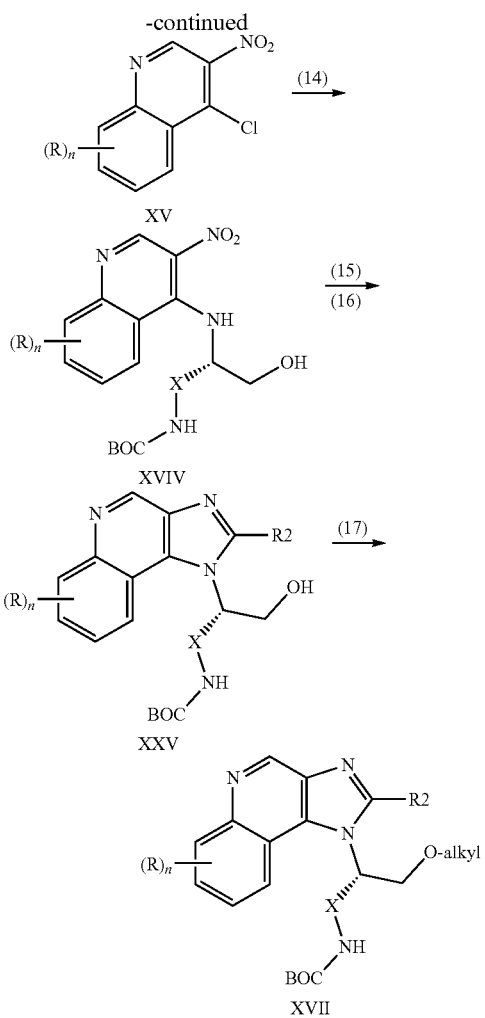

Reductive amination of the alkyl amine XIX of Reaction Scheme II or the alkyl amine XXI of Reaction Scheme III using an alkyl aldehyde[R4C(O)H] prior to step (12) can be used to create compounds of the description (described above) where R4 is alkyl.

Compounds of the disclosure can be prepared according to Reaction Schemes I-IV with the starting alpha-amino acid compound of Formula X being replaced with a beta-amino acid compound, such as for example (S)-3,4-diaminobutanoic acid, (5)-beta-lysine, (S)-beta-homolysine, or amine protected analogs of a beta-amino acid.

The compounds of the disclosure of Formula VI can also be prepared from the procedures of Reaction Schemes I and II by using the racemic version of the diaminoalkylcarboxylic acid of Formula X.

Compounds of Formula I can be prepared by starting the reaction scheme with a diaminoalkylcarboxylic acid of Formula X that has high enantiomeric purity. Alternatively, a racemic mixture of diaminoalkylcarboxylic acid or a diaminoalkylcarboxylic acid of low enantiomeric purity (for example, 10-70% enantiomeric excess) can be used with the final product isolated as the desired Formula I enantiomer using any suitable procedure for the resolution of a mixture of enantiomers. A well-known method for the resolution of a mixture of enantiomers is HPLC chromatography using a column with a chiral stationary phase (CSP). Another standard method for the resolution of a mixture of enantiomers involves reacting the mixture with an optically pure carboxylic acid to form diastereomeric salts that can be readily separated by for example recrystallization or chromatography methods. Regeneration of the free base completes the resolution process. Examples of resolving agents that are available in high enantiomeric purity include, but are not limited to, (+)-tartaric acid, (−)-mandelic acid, (−)-malic acid, (+)-camphor-10-sulfonic acid, and (+)-2,3-dibenzoyl-tartaric acid. If needed, different types of resolution steps can be combined and multiple resolution steps can be utilized to achieve the desired enantiomeric purity. The enantiomeric purity is represented as the percent enantiomeric excess (% ee). Methods for the resolution of isomers are described in the references: Y. Okamoto, Chemical Society Reviews, 2008, 37, pages 2593-2608; G. Gubitz, Biopharmaceutics and Drug Disposition, 2001, 22, pages 291-336; and S. Mane, Analytical Methods, 2016, 8, pages 7567-7586.

In addition, compounds of Formulas II-V can be prepared from a racemic mixture or low enantiomeric purity mixture using a suitable resolution method as described above.

In the preparation of the compounds of the disclosure it is understood by one of ordinary skill in the art that it may be necessary to protect a particular functional group while reacting other functional groups of an intermediate compound. The need for such protection will vary depending on the nature of the particular functional group and the conditions of the particular reaction step. A review of reactions for protecting and deprotecting functional groups can be found in P. G. M. Wuts, Greene's Protective Groups in Organic Synthesis, John Wiley & Sons, New York, USA, 2014.

Conventional methods and techniques of separation and purification can be used to isolate the IRM compounds used in the compositions of the disclosure. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

The enantiomeric excess of the compounds of the disclosure can be determined using standard analytical assays such as gas chromatography or HPLC with a column having a chiral stationary phase (CSP). Suitable columns with a CSP are available from Chiral Technologies, Inc., Westchester, Pa.

Enantiomeric excess (% ee) is calculated according to Equation 1.

$$\text{enantiomeric excess (\% } ee) = \frac{(\text{mole \% of major enantiomer}) - (\text{mol \% of minor enantiomer})}{(\text{mole \% of major enantiomer}) + (\text{mole \% of minor enantiomer})} \times 100. \qquad \text{Equation 1}$$

Enantiomeric excess (% ee) can be calculated from a chiral HPLC chromatogram by comparing the peak areas of the major enantiomer and minor enantiomer signals according to Equation 2.

$$\text{enantiomeric excess (\% } ee) = \frac{(\text{peak area of major enantiomer}) - (\text{peak area of minor enantiomer})}{(\text{peak area of major enantiomer}) + (\text{peak area of minor enantiomer})} \times 100. \qquad \text{Equation 2}$$

Prodrugs of the disclosed compounds can also be prepared by attaching to the compounds a functional group that can be cleaved under physiological conditions. Typically, a cleavable functional group will be cleaved in vivo by various mechanisms (such a through a chemical (e.g., hydrolysis) or enzymatic transformation) to yield a compound of the disclosure. A discussion of the use of prodrugs is provided by T. Higuchi and W. Stella. "Prodrugs as Novel Delivery Systems", vol. 14 of the ACS Symposium Series, and in Bioreversible Carriers in Drug Design, ed. Edward B. Roche, American Pharmaceutical Association and Pergamon Press, 1987.

Pharmaceutical Compositions and Biological Activity

Pharmaceutical compositions of the disclosure are also contemplated. Pharmaceutical compositions of the disclosure contain a therapeutically effective amount of a compound or salt of the disclosure (described herein) in combination with a pharmaceutically acceptable carrier.

The compound of Formula I or Formula VI may be provided in any pharmaceutical composition suitable for administration to a subject (human or animal) and may be present in the pharmaceutical composition in any suitable form (for example as a solution, a suspension, an emulsion, or any form of a mixture). The pharmaceutical composition may be formulated with any pharmaceutically acceptable excipient, carrier, or vehicle. In some embodiments, the pharmaceutically acceptable carrier comprises water (for example phosphate buffered saline or citrate buffered saline). In some embodiments, the pharmaceutically carrier comprises an oil (for example corn, sesame, cottonseed, soybean, or safflower oil). The pharmaceutical composition may further include one or more additives including suspending agents, surfactants, dispersing agents, and preservatives (such as an anti-oxidant).

In some embodiments of the pharmaceutical composition, the compound of Formula I or Formula VI can be incorporated in a homogeneously dispersed formulation. In some embodiments of the pharmaceutical composition, the compound of Formula I or Formula VI can be incorporated in an emulsified formulation. In some embodiments of the pharmaceutical composition, the compound of Formula I or Formula VI can be incorporated in an oil-in-water formulation. An oil-in-water formulation can comprise an oil component, an aqueous component, and one or more surfactants (for example formulations comprising soybean oil, TWEEN 80, SPAN 85, and phosphate buffered saline). In some embodiments of the pharmaceutical composition, the compound of Formula I or Formula VI can be incorporated into a liposome formulation.

In some embodiments, the pharmaceutical composition can further comprise an antigen in an amount effective to generate an immune response against the antigen. In some embodiments, the antigen is a vaccine.

The pharmaceutical composition can be administered in any suitable manner (parenterally or non-parenterally). In some embodiments, the pharmaceutical composition can be administered by an intradermal, subcutaneous, intramuscular, or intravenous injection.

In any embodiment of a pharmaceutical composition comprising a compound of Formula I, the compound of Formula I is present in the composition in at least 80% enantiomeric excess, at least 90% enantiomeric excess, at least 95% enantiomeric excess, at least 96% enantiomeric excess, at least 96% enantiomeric excess, at least 97% enantiomeric excess, at least 98% enantiomeric excess, at least 99% enantiomeric excess, at least 99.5% enantiomeric, or at least 99.8% enantiomeric excess.

In preferred embodiments of pharmaceutical compositions comprising a compound of Formula I, the compound of Formula I is present in at least 95% enantiomeric excess, at least 96% enantiomeric excess, at least 97% enantiomeric excess, or at least 98% enantiomeric excess.

In any embodiment of a pharmaceutical composition comprising a compound of Formula I, the opposite enantiomer to the compound of Formula I is present in the composition in less than 10%, less than 5%, less than 2.5%, less than 2%, less than 1.5%, less than 1%, less than 0.5%, less than 0.25%, or less than 0.1%.

In preferred embodiments of pharmaceutical compositions comprising a compound of Formula I, the opposite enantiomer to the compound of Formula I is present in less than 2.5%, less than 2%, less than 1.5%, or less than or equal to 1%.

The exact amount of compound or salt used in a pharmaceutical composition of the disclosure will vary according to factors known to those of skill in the art, such as the physical and chemical nature of the compound or salt, the nature of the carrier, and the intended dosing regimen.

In some embodiments, the concentration of the compound of Formula I or the compound of Formula VI in the pharmaceutical composition can be from about 0.05 to 2.4 mg/mL. In some embodiments, the concentration of the compound of Formula I or the compound of Formula VI in the pharmaceutical composition can be from about 0.0005 to 0.06 mg/mL. In some embodiments, the concentration of the compound of Formula I or the compound of Formula VI in the pharmaceutical composition can be from about 0.0005 to 0.01 mg/mL. In some embodiments, the concentration of the compound of Formula I or the compound of Formula VI in the pharmaceutical composition can be from about 0.001 to 0.01 mg/mL. In some embodiments, the concentration of the compound of Formula I or the compound of Formula VI in the pharmaceutical composition can be from about 0.0005 to 0.005 mg/mL.

In some embodiments, the compositions of the disclosure will contain sufficient active ingredient or prodrug to provide a dose of about 100 nanograms per kilogram (ng/kg) to about 50 milligrams per kilogram (mg/kg), preferably about 10 micrograms per kilogram (ng/kg) to about 5 mg/kg, of the compound or salt to the subject.

In some embodiments, the compositions of the disclosure will contain sufficient active ingredient or prodrug to provide a dose of for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)×0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used to administer the compounds or salts of the disclosure to a human or animal. Dosage forms that can be used include, for example, tablets, lozenges, capsules, parenteral formulations, creams, ointments, topical gels, aerosol formulations, liquid formulations (e.g., aqueous formulation), transdermal patches, and the like. These dosage forms can be prepared with conventional pharmaceutically acceptable carriers and additives using conventional methods, which generally include the step of bringing the active ingredient into association with the carrier. A preferred dosage form has one or more of compounds or salts of the disclosure dissolved in an aqueous formulation.

Compounds or salts disclosed herein induce the production of certain cytokines in experiments performed according to the description of the Examples. These results indicate that the compounds or salts are useful for enhancing the immune response in a number of different ways, making them useful in the treatment of a variety of disorders.

The compounds or salts described herein can be administered as the single therapeutic agent in the treatment regimen, or the compounds or salts described herein may be administered in combination with other active agents, including antivirals, antibiotics, proteins, peptides, oligonucleotides, antibodies, etc.

Compounds or salts described herein induce the production of cytokines (e.g., IFN-alpha, IFN-gamma, TNF-alpha, IP-10) in experiments performed according to the tests set forth below. These results indicate that the compounds of the disclosure or salts are useful for activating the immune response in a number of different ways, rendering them useful in the treatment of a variety of disorders. As such, the compounds or salts of the disclosure (particularly compounds or salts of Formulas I and VI) are agonists of cytokine biosynthesis and production, particularly agonists of IFN-alpha, IFN-gamma, TNF-alpha, and IP-10 cytokine biosynthesis and production.

It is believed that one way in which the compounds or salts of the disclosure (particularly compounds or salts of Formulas I and VI) induce cytokine production is through the activation of Toll-like receptors (TLRs) in the immune system, particularly TLR-7 and/or TLR-8, however other mechanisms may be involved. It is believed that in the immune system pathways (i.e., mechanisms) for cytokine induction, the compounds or salts of the disclosure (Formulas I and VI) primarily act as agonists of TLR-7 and/or TLR-8, however other pathways or activities may be involved.

Administration of the compounds or salts described herein can induce the production of interferon-alpha (IFN-alpha), interferon-gamma (IFN-gamma), tumor necrosis factor-alpha (TNF-alpha), and IP-10 in cells. Cytokines whose biosynthesis can be induced by compounds or salts of the disclosure include IFN-alpha, IFN-gamma, TNF-alpha, IP-10, and a variety of other cytokines. Among other effects, these cytokines can inhibit virus production and tumor cell growth, making the compounds or salts useful in the treatment of viral diseases and neoplastic diseases. Accordingly, the disclosure provides a method of inducing cytokine biosynthesis in a human or animal by administering an effective amount of a compound or salt of the disclosure to the human or animal. The human or animal to which the compound or salt is administered for induction of cytokine production may have one or more diseases, disorders, or conditions described below, for example a viral disease or a neoplastic disease, and administration of the compound or salt may provide therapeutic treatment. Alternatively, the compound or salt may be administered to the human or animal prior to the human or animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. In addition, the compounds or salts may cause proliferation and differentiation of B-lymphocytes.

Conditions for which compounds or salts or compositions identified herein may be used as treatment include, but are not limited to:

Viral diseases such as, for example, diseases resulting from infection by an adenovirus, a herpes virus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenza virus, avian influenza), a paramyxovirus (e.g., parainfluenza virus, mumps virus, measles virus, and respiratory syncytial virus (RSV), a coronavirus (e.g., SARS), a papovavirus (e.g., papillomaviruses, such as those that cause genital warts, common warts, or plantar warts), hepadnavirus (e.g., hepatitis B virus), a flavivirus (e.g., hepatitis C virus or Dengue virus), or a retrovirus (e.g., a lentivirus such as HIV), and ebola virus.

Neoplastic diseases such as bladder cancer, cervical dysplasia, cervical cancer, actinic keratosis, basal cell carcinoma, cutaneous T-cell lymphoma, mycosis fungoides, Sezary Syndrome, HPV associated head and neck cancer (e.g., HPV positive oropharyngeal squamous cell carcinoma), Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, esophageal cancer, and other cancers;

$T_H2$-mediated atopic diseases such as atopic dermatitis or eczema, eosinophilia, asthma, allergy, allergic rhinitis, and Omenn's syndrome;

Diseases associated with wound repair, such as, for example, inhibition of keloid formation and other types of scarring (e.g., enhancing wound healing, including chronic wounds);

Parasitic diseases including but not limited to malaria, leishmaniasis, cryptosporidiosis, toxoplasmosis, and trypanosome infection.

In addition, a compound, salt, or pharmaceutical composition described herein may be used as a vaccine adjuvant for use in conjunction with any material that increases either humoral and/or cell mediated immune responses, such as, for example, tumor antigens (e.g., MAGE-3, NY-ESO-1); live viral, bacterial, or parasitic immunogens; inactivated viral, protozoal, fungal, or bacterial immunogens; toxoids; toxins; polysaccharides; proteins; glycoproteins; peptides; cellular vaccines; DNA vaccines; autologous vaccines; recombinant proteins; and the like.

Examples of vaccines that can benefit from use of a compound, salt, or composition identified herein as a vaccine adjuvant include BCG vaccine, cholera vaccine, plague vaccine, typhoid vaccine, hepatitis A vaccine, hepatitis B vaccine, hepatitis C vaccine, influenza A vaccine, influenza B vaccine, malaria vaccine, parainfluenza vaccine, polio vaccine, rabies vaccine, measles vaccine, mumps vaccine, rubella vaccine, yellow fever vaccine, tetanus vaccine, diphtheria vaccine, haemophilus influenza b vaccine, tuberculosis vaccine, meningococcal and pneumococcal vaccines, adenovirus vaccine, HIV vaccine, chicken pox vaccine, cytomegalovirus vaccine, dengue vaccine, feline leukemia vaccine, fowl plague vaccine, HSV-1 vaccine and HSV-2 vaccine, hog cholera vaccine, Japanese encephalitis vaccine, respiratory syncytial virus vaccine, rotavirus vaccine, papilloma virus vaccine, yellow fever vaccine, and ebola virus vaccine.

Compounds, salts, or pharmaceutical compositions identified herein may be particularly useful as vaccine adjuvants when used in conjunction with tumor antigens associated with colorectal cancer, head and neck cancer, breast cancer, lung cancer and melanoma.

Compounds, salts, or pharmaceutical compositions identified herein may be particularly useful in individuals having compromised immune function. For example, compounds, salts, or compositions may be used for treating opportunistic infections and tumors that occur after suppression of cell mediated immunity in, for example, transplant patients, cancer patients, and HIV patients.

One or more of the above diseases or types of diseases, for example, a viral disease or neoplastic disease may be treated in a human or animal in need thereof (having the disease) by administering a therapeutically effective amount of a compound, salt, or composition to the human or animal.

A human or animal may also be vaccinated by administering an effective amount of a compound, salt, or composition described herein as a vaccine adjuvant. In one embodiment, a method of vaccinating a human or animal includes administering an effective amount of a compound, salt, or composition described herein to the human or animal as a vaccine adjuvant. The vaccine adjuvant can be co-administered with the material that increases one or more humoral and cell mediated immune responses by including each in the same composition. Alternatively, the vaccine adjuvant and the material that increases either humoral and/or cell mediated immune responses can be in separate compositions.

Compounds, salts, or compositions identified herein may as prophylactic or therapeutic vaccine adjuvants in veterinary applications. Compounds, salts, or compositions identified herein may be administered to, for example, horses, cattle, sheep, dogs, cats, poultry (such as chickens or turkeys), etc.

Compounds or salts or compositions identified herein may be particularly useful when an effective amount is administered to a human or animal to treat bladder cancer, cervical dysplasia, actinic keratosis, basal cell carcinoma, genital warts, herpes virus infection, or cutaneous T-cell lymphoma. For these conditions, administration of the compound, salt, or composition of the disclosure is preferably topical (i.e., applied directly to the surface of a tumor, a lesion, a wart, or an infected tissue, etc.).

In one embodiment an effective amount of compound, salt, or composition described herein, such as an aqueous composition is administered into the bladder of a human or animal that has at least one tumor of the bladder by intravesical instillation (e.g., administration using a catheter).

An amount of a compound or salt effective to induce cytokine biosynthesis will typically cause one or more cell types, such as monocytes, macrophages, dendritic cells, and B-cells to produce an amount of one or more cytokines, such as, for example, IFN-alpha, IFN-gamma, TNF-alpha, and IP-10 that is increased (induced) over a background level of such cytokines. The precise dose will vary according to factors known in the art but is typically to be a dose of about 100 ng/kg to about 50 mg/kg, preferably about 10 ng/kg to about 5 mg/kg. In other embodiments, the amount can be, for example, from about 0.01 mg/m$^2$ to about 5.0 mg/m$^2$, (computed according to the Dubois method as described above) although in other embodiments the induction of cytokine biosynthesis may be performed by administering a compound or salt in a dose outside this range. In some of these embodiments, the method includes administering sufficient compound or salt or composition to provide a dose from about 0.1 mg/m$^2$ to about 2.0 mg/m$^2$ to the subject, for example, a dose of from about 0.4 mg/m$^2$ to about 1.2 mg/m$^2$.

A method of treating a viral infection in a human or animal and a method of treating a neoplastic disease in a human or animal can include administering an effective amount of a compound or salt described herein to the human or animal. An effective amount to treat or inhibit a viral infection can be an amount that will cause a reduction in one or more of the manifestations of viral infection, such as viral lesions, viral load, rate of virus production, and mortality as compared to untreated humans or animals. The precise amount that is effective for such treatment will vary according to factors known in the art but it is normally a dose of about 100 ng/kg to about 50 mg/kg, preferably about 10 ng/kg to about 5 mg/kg. An amount of a compound or salt effective to treat a neoplastic condition can be an amount that causes a reduction in tumor size or in the number of tumor foci. The precise amount will vary according to factors known in the art but is typically about 100 ng/kg to about 50 mg/kg, preferably about 10 ng/kg to about 5 mg/kg. In other embodiments, the amount is typically, for example, from about 0.01 mg/m$^2$ to about 5.0 mg/m$^2$, (computed according to the Dubois method as described above) although in some embodiments the induction of cytokine biosynthesis may be performed by administering a compound or salt in a dose outside this range. In some of these embodiments, the method includes administering sufficient compound or salt or composition to provide a dose from about 0.1 mg/m$^2$ to about 2.0 mg/m$^2$ to the subject, for example, a dose of from about 0.4 mg/m$^2$ to about 1.2 mg/m$^2$.

EMBODIMENTS

Embodiment 1 is a compound of Formula (I):

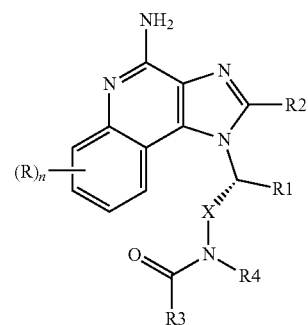

Formula I wherein:
n is an integer of 0 or 1;
R is selected from the group consisting of halogen, hydroxy, alkyl, alkoxy, and —C(O)—O-alkyl;
X is alkylene, wherein the alkylene group can be optionally interrupted by one or more —O— groups;
R1 is selected from the group consisting of $C_{1-5}$alkyl and —$C_{1-3}$alkylene-O—$C_{1-3}$alkyl;
R2 is selected from the group consisting of hydrogen, methyl, ethyl, n-propyl, n-butyl, —$CH_2OCH_3$, —$CH_2OCH_2CH_3$, and —$CH_2CH_2OCH_3$;
R3 is alkyl, wherein the alkyl group can be optionally interrupted by one or more —O— groups;

R4 is selected from the group consisting of hydrogen, methyl, ethyl, n-propyl, and isopropyl; or a pharmaceutically acceptable salt thereof.

Embodiment 2 is the compound or salt of embodiment 1, wherein R is selected from the group consisting of halogen, hydroxy, $C_{1-7}$alkyl, $C_{1-7}$ alkoxy, and —C(O)—O—$C_{1-5}$alkyl.

Embodiment 3 is the compound or salt of embodiment 1 or 2, wherein R is selected from the group consisting of hydroxy, F, and Cl.

Embodiment 4 is the compound or salt of any one of the embodiments 1-3, wherein R is selected from the group consisting of F and Cl.

Embodiment 5 is the compound or salt of embodiment 1, wherein n is 0.

Embodiment 6 is the compound or salt of any one of the embodiments 1-5, wherein R4 is selected from the group consisting of hydrogen, methyl, and ethyl.

Embodiment 7 is the compound or salt of any one of the embodiments 1-6, wherein R4 is hydrogen.

Embodiment 8 is the compound or salt of any one of the embodiments 1-7, wherein X is alkylene.

Embodiment 9 is the compound or salt of any one of the embodiments 1-8, wherein X is $C_{1-8}$alkylene.

Embodiment 10 is the compound or salt of any one of the embodiments 1-9, wherein X is $C_{1-5}$alkylene.

Embodiment 11 is the compound or salt of any one of the embodiments 1-9, wherein X is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, and —$CH_2CH_2CH_2CH_2CH_2CH_2CH_2CH_2$—.

Embodiment 12 is the compound or salt of any one of the embodiments 1-11, wherein X is selected from the group consisting of —$CH_2CH_2CH_2$—, —$CH_2CH_2CH_2CH_2$—, and —$CH_2CH_2CH_2CH_2CH_2$—.

Embodiment 13 is the compound or salt of any one of the embodiments 1-12, wherein X is —$CH_2CH_2CH_2$—.

Embodiment 14 is the compound or salt of any one of the embodiments 1-13, wherein R1 is —$CH_2OCH_3$ or —$CH_2OCH_2CH_3$.

Embodiment 15 is the compound or salt of any one of the embodiments 1-14, wherein R1 is —$CH_2OCH_2CH_3$.

Embodiment 16 is the compound or salt of any one of the embodiments 1-15, wherein R2 is selected from the group consisting of hydrogen, methyl, and ethyl.

Embodiment 17 is the compound or salt of any one of the embodiments 1-16, wherein R2 is hydrogen.

Embodiment 18 is the compound or salt of any one of the embodiments 1-17, wherein R3 is $C_{1-4}$alkyl.

Embodiment 19 is the compound or salt of any one of the embodiments 1-17, wherein R3 is $C_{5-19}$alkyl.

Embodiment 20 is the compound or salt of any one of the embodiments 1-17, wherein R3 is $C_{7-19}$alkyl.

Embodiment 21 is the compound or salt of any one of the embodiments 1-17, wherein R3 is $C_{9-19}$alkyl.

Embodiment 22 is the compound or salt of any one of the embodiments 1-17, wherein R3 is $C_{9-17}$alkyl.

Embodiment 23 is the compound or salt of any one of the embodiments 1-17, wherein R3 is $C_{9-15}$alkyl.

Embodiment 24 is the compound or salt of any one of the embodiments 1-17, wherein R3 is $C_{11-17}$alkyl.

Embodiment 25 is the compound or salt of any one of the embodiments 1-17, wherein R3 is selected from the group consisting of —$CH_2(CH_2)_{3-17}CH_3$.

Embodiment 26 is the compound or salt of any one of the embodiments 1-17, wherein R3 is selected from the group consisting of —$CH_2(CH_2)_3CH_3$, —$CH_2(CH_2)_4CH_3$, —$CH_2(CH_2)_5CH_3$, —$CH_2(CH_2)_6CH_3$, —$CH_2(CH_2)_7CH_3$, —$CH_2(CH_2)_9CH_3$, —$CH_2(CH_2)_{11}CH_3$, —$CH_2(CH_2)_{13}CH_3$, —$CH_2(CH_2)_{15}CH_3$, and —$CH_2(CH_2)_{17}CH_3$.

Embodiment 27 is the compound or salt of any one of the embodiments 1-17, wherein R3 is selected from the group consisting of —$CH_2(CH_2)_5CH_3$, —$CH_2(CH_2)_7CH_3$, —$CH_2(CH_2)_9CH_3$, —$CH_2(CH_2)_{11}CH_3$, —$CH_2(CH_2)_{13}CH_3$, —$CH_2(CH_2)_{15}CH_3$, and —$CH_2(CH_2)_{17}CH_3$.

Embodiment 28 is the compound or salt of any one of the embodiments 1-17, wherein R3 is selected from the group consisting of —$CH_2(CH_2)_7CH_3$, —$CH_2(CH_2)_9CH_3$, —$CH_2(CH_2)_{11}CH_3$, —$CH_2(CH_2)_{13}CH_3$, —$CH_2(CH_2)15CH_3$, and —$CH_2(CH_2)_{17}CH_3$.

Embodiment 29 is the compound or salt of any one of the embodiments 1-17, wherein R3 is —$CH_2(CH_2)_7CH_3$.

Embodiment 30 is the compound or salt of any one of the embodiments 1-17, wherein R3 is —$CH_2(CH_2)_9CH_3$.

Embodiment 31 is the compound or salt of any one of the embodiments 1-17, wherein R3 is —$CH_2(CH_2)_{11}CH_3$.

Embodiment 32 is the compound or salt of any one of the embodiments 1-17, wherein R3 is —$CH_2(CH_2)_{13}CH_3$.

Embodiment 33 is the compound or salt of any one of the embodiments 1-17, wherein R3 is —$CH_2(CH_2)_{15}CH_3$.

Embodiment 34 is the compound or salt of embodiment 1, wherein X is alkylene optionally interrupted by one or more —O— groups; R1 is selected from the group consisting of $C_{1-5}$alkyl and —$C_{1-3}$alkylene-O—$C_{1-3}$alkyl; R2 is selected from the group consisting of hydrogen, methyl, and ethyl; R3 is $C_{7-17}$alkyl; R4 is hydrogen; and n is 0.

Embodiment 35 is the compound or salt of embodiment 1, wherein X is $C_{2-5}$alkylene; R1 is selected from the group consisting of —$CH_2OCH_3$ and —$CH_2OCH_2CH_3$; R2 is selected from the group consisting of hydrogen, methyl, and ethyl; R3 is $C_{7-17}$alkyl; R4 is hydrogen; and n is 0.

Embodiment 36 is the compound or salt of embodiment 1, wherein X is $C_{2-5}$alkylene; R1 is selected from the group consisting of —$CH_2OCH_3$ and —$CH_2OCH_2CH_3$; R2 is hydrogen; R3 is $C_{7-17}$alkyl; R4 is hydrogen; and n is 0.

Embodiment 37 is the compound or salt of embodiment 1, wherein X is selected from the group consisting of —$CH_2CH_2CH_2$—, —$CH_2CH_2CH_2CH_2$—, and —$CH_2CH_2CH_2CH_2CH_2$—; R1 is selected from the group consisting of —$CH_2OCH_3$ and —$CH_2OCH_2CH_3$; R2 is selected from the group consisting of hydrogen, methyl, and ethyl; R3 is $C_{7-17}$alkyl; R4 is hydrogen; and n is 0.

Embodiment 38 is the compound or salt of embodiment 1, wherein X is —$CH_2CH_2CH_2$—; R1 is selected from the group consisting of —$CH_2OCH_3$ and —$CH_2OCH_2CH_3$; R2 is hydrogen; R3 is $C_{7-17}$alkyl; R4 is hydrogen; and n is 0.

Embodiment 39 is the compound or salt of embodiment 1, wherein X is —$CH_2CH_2CH_2$—; R1 is selected from the group consisting of —$CH_2OCH_3$ and —$CH_2OCH_2CH_3$; R2 is hydrogen; R3 is $C_{9-15}$alkyl; R4 is hydrogen; and n is 0.

Embodiment 40 is the compound or salt of embodiment 1, wherein X is —$CH_2CH_2CH_2$—; R1 is selected from the group consisting of —$CH_2OCH_3$ and —$CH_2OCH_2CH_3$; R2 is hydrogen; R3 is $C_{11-15}$alkyl; R4 is hydrogen; and n is 0.

Embodiment 41 is the compound or salt of embodiment 1, wherein X is —$CH_2CH_2CH_2$—; R1 is selected from the group consisting of —$CH_2OCH_3$ and —$CH_2OCH_2CH_3$; R2 is hydrogen; R3 is selected from the group consisting of —$CH_2(CH_2)_7CH_3$, —$CH_2(CH_2)_9CH_3$, —$CH_2(CH_2)_{11}CH_3$, and —$CH_2(CH_2)_{13}CH_3$; R4 is hydrogen; and n is 0.

Embodiment 42 is the compound or salt of embodiment 1, wherein X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_7$CH$_3$; R4 is hydrogen; and n is 0.

Embodiment 43 is the compound or salt of embodiment 1, wherein X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_9$CH$_3$; R4 is hydrogen; and n is 0.

Embodiment 44 is the compound or salt of embodiment 1, wherein X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_{11}$CH$_3$; R4 is hydrogen; and n is 0.

Embodiment 45 is the compound or salt of embodiment 1, wherein X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_{13}$CH$_3$; R4 is hydrogen; and n is 0.

Embodiment 46 is the compound or salt of embodiment 1, wherein X is —CH$_2$CH$_2$CH$_2$—; R1 is selected from the group consisting of —CH$_2$OCH$_3$ and —CH$_2$OCH$_2$CH$_3$; R2 is hydrogen; R3 is —CH$_2$(CH$_2$)$_{15}$CH$_3$; R4 is hydrogen; and n is 0.

Embodiment 47 is the compound or salt of any one of the embodiments 1-46, wherein the pharmaceutically acceptable salt is hydrochloride.

Embodiment 48 is a pharmaceutical composition comprising a therapeutically effective amount of a compound or salt of any one of the embodiments 1-47 in combination with a pharmaceutically acceptable carrier.

Embodiment 49 is the pharmaceutical composition of embodiment 48, wherein the compound or salt is present in at least 80% enantiomeric excess.

Embodiment 50 is the pharmaceutical composition of embodiment 48, wherein the compound or salt is present in at least 90% enantiomeric excess.

Embodiment 51 is the pharmaceutical composition of embodiment 48, wherein the compound or salt is present in at least 95% enantiomeric excess.

Embodiment 52 is the pharmaceutical composition of embodiment 48, wherein the compound or salt is present in at least 97% enantiomeric excess.

Embodiment 53 is the pharmaceutical composition of embodiment 48, wherein the compound or salt is present in at least 98% enantiomeric excess.

Embodiment 54 is the pharmaceutical composition of embodiment 48, wherein the compound or salt is present in at least 99% enantiomeric excess.

Embodiment 55 is the pharmaceutical composition of embodiment 48, wherein the compound or salt is present in at least 99.5% enantiomeric excess.

Embodiment 56 is the pharmaceutical composition of embodiment 48, wherein the compound or salt is present in at least 99.8% enantiomeric excess.

Embodiment 57 is the pharmaceutical composition of any one of the embodiments 48-56, further comprising an antigen.

Embodiment 58 is the pharmaceutical composition of any one of the embodiments 48-57 for use in treating an infectious disease in a human or animal.

Embodiment 59 is the pharmaceutical composition of any one of the embodiments 48-58 for use in treating a viral, bacterial, fungal, or parasitic infection in a human or animal.

Embodiment 60 is a method of inducing cytokine biosynthesis in a human or animal comprising administering an effective amount of a compound or salt of any one of the embodiments 1-47 to the human or animal.

Embodiment 61 is a method of inducing biosynthesis of IFN-alpha in a human or animal comprising administering an effective amount of a compound or salt of any one of the embodiments 1-47 to the human or animal.

Embodiment 62 is a method of inducing biosynthesis of IFN-gamma in a human or animal comprising administering an effective amount of a compound or salt of any one of the embodiments 1-47 to the human or animal.

Embodiment 63 is a method of inducing biosynthesis of TNF-alpha in a human or animal comprising administering an effective amount of a compound or salt of any one of the embodiments 1-47 to the human or animal.

Embodiment 64 is a method of inducing biosynthesis of IP-10 in a human or animal comprising administering an effective amount of a compound or salt of any one of the embodiments 1-47 to the human or animal.

Embodiment 65 is a compound or salt of any one of the embodiments 1-47 for use as a vaccine adjuvant in treating an infectious disease in a human or animal.

Embodiment 66 is a compound or salt of any one of the embodiments 1-47 for use as a vaccine adjuvant in treating a viral, bacterial, fungal, or parasitic infection in a human or animal.

Embodiment 67 is a compound or salt of embodiment 65 or 66, wherein the treatment is a therapeutic or prophylactic treatment.

Embodiment 68 is a compound selected from the group consisting of:

N-[(4S)-4-(4-aminoimidazo[4,5-c]quinolin-1-yl)-5-ethoxypentyl]acetamide;
N-[(4S)-4-(4-aminoimidazo[4,5-c]quinolin-1-yl)-5-ethoxypentyl]propanamide;
N-[(4S)-4-(4-aminoimidazo[4,5-c]quinolin-1-yl)-5-ethoxypentyl]-2-methylpropanamide;
N-[(4S)-4-(4-aminoimidazo[4,5-c]quinolin-1-yl)-5-ethoxypentyl]butanamide;
N-[(4S)-4-(4-aminoimidazo[4,5-c]quinolin-1-yl)-5-ethoxypentyl]-3-methylbutanamide;
N-[(4S)-4-(4-aminoimidazo[4,5-c]quinolin-1-yl)-5-ethoxypentyl]pentanamide;
N-[(4S)-4-(4-aminoimidazo[4,5-c]quinolin-1-yl)-5-ethoxypentyl]hexanamide;
N-[(4S)-4-(4-aminoimidazo[4,5-c]quinolin-1-yl)-5-ethoxypentyl]octanamide;
N-[(4S)-4-(4-aminoimidazo[4,5-c]quinolin-1-yl)-5-ethoxypentyl]nonanamide;
N-[(4S)-4-(4-aminoimidazo[4,5-c]quinolin-1-yl)-5-ethoxypentyl]decanamide; or a pharmaceutically acceptable salt thereof.

Embodiment 69 is a compound selected from the group consisting of:

N-[(4S)-4-(4-aminoimidazo[4,5-c]quinolin-1-yl)-5-ethoxypentyl]dodecanamide;
N-[(4S)-4-(4-aminoimidazo[4,5-c]quinolin-1-yl)-5-ethoxypentyl]tetradecanamide;
N-[(4S)-4-(4-aminoimidazo[4,5-c]quinolin-1-yl)-5-ethoxypentyl]hexadecanamide; or a pharmaceutically acceptable salt thereof.

Embodiment 70 is a compound selected from the group consisting of:

N-[(4S)-4-(4-aminoimidazo[4,5-c]quinolin-1-yl)-5-ethoxypentyl]octadecanamide;
N-[(4S)-4-(4-aminoimidazo[4,5-c]quinolin-1-yl)-5-ethoxypentyl]eicosanamide;
or a pharmaceutically acceptable salt thereof.

Embodiment 71 is a compound of Formula (VI):

Formula VI wherein:
n is an integer of 0 or 1;
R is selected from the group consisting of halogen, hydroxy, alkyl, alkoxy, and —C(O)—O-alkyl;
X is alkylene, wherein the alkylene group can be optionally interrupted by one or more —O— groups;
R1 is selected from the group consisting of $C_{1-5}$alkyl and —$C_{1-3}$alkylene-O—$C_{1-3}$alkyl;
R2 is selected from the group consisting of hydrogen, methyl, ethyl, n-propyl, and n-butyl, —CH$_2$OCH$_3$, —CH$_2$OCH$_2$CH$_3$, and —CH$_2$CH$_2$OCH$_3$;
R3 is alkyl, wherein the alkyl group can be optionally interrupted by one or more —O— groups;
R4 is selected from the group consisting of hydrogen, methyl, ethyl, n-propyl, and isopropyl; or a pharmaceutically acceptable salt thereof.

Embodiment 72 is the compound or salt of embodiment 71, wherein R is selected from the group consisting of halogen, hydroxy, $C_1$-7 alkoxy, and —C(O)—O—$C_{1-5}$alkyl.

Embodiment 73 is the compound or salt of embodiment 71 or 72, wherein R is selected from the group consisting of hydroxy, F, and Cl.

Embodiment 74 is the compound or salt of embodiment 71, wherein n is 0.

Embodiment 75 is the compound or salt of any one of the embodiments 71-74, wherein R4 is hydrogen.

Embodiment 76 is the compound or salt of any one of the embodiments 71-75, wherein R2 is selected from the group consisting of hydrogen, methyl, and ethyl.

Embodiment 77 is the compound or salt of any one of the embodiments 71-76, wherein R2 is hydrogen.

Embodiment 78 is the compound or salt of any one of the embodiments 71-77, wherein R3 is $C_{1-4}$alkyl.

Embodiment 79 is the compound or salt of any one of the embodiments 71-77, wherein R3 is $C_{5-19}$alkyl.

Embodiment 80 is the compound or salt of any one of the embodiments 71-77, wherein R3 is selected from the group consisting of —CH$_2$(CH$_2$)$_{3-17}$CH$_3$.

Embodiment 81 is the compound or salt of any one of the embodiments 71-80, wherein X is $C_{1-5}$alkylene.

Embodiment 82 is the compound or salt of any one of the embodiments 71-81, wherein X is $C_{2-5}$alkylene.

Embodiment 83 is the compound or salt of any one of the embodiments 71-81, wherein X is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, and —CH$_2$CH$_2$CH$_2$CH$_2$CH$_2$CH$_2$CH$_2$CH$_2$—.

Embodiment 84 is the compound or salt of any one of the embodiments 71-83, wherein X is selected from the group consisting of —CH$_2$CH$_2$CH$_2$—, —CH$_2$CH$_2$CH$_2$CH$_2$—, and —CH$_2$CH$_2$CH$_2$CH$_2$CH$_2$—.

Embodiment 85 is the compound or salt of any one of the embodiments 71-84, wherein X is —CH$_2$CH$_2$CH$_2$—.

Embodiment 86 is the compound or salt of embodiment 71, wherein X is selected from the group consisting of —CH$_2$CH$_2$CH$_2$—, —CH$_2$CH$_2$CH$_2$CH$_2$—, and —CH$_2$CH$_2$CH$_2$CH$_2$CH$_2$—; R1 is selected from the group consisting of —CH$_2$OCH$_3$ and —CH$_2$OCH$_2$CH$_3$; R2 is selected from the group consisting of hydrogen, methyl, and ethyl; R3 is $C_{7-17}$alkyl; R4 is hydrogen; and n is 0.

Embodiment 87 is the compound or salt of any one of the embodiments 71-86, wherein the pharmaceutically acceptable salt is hydrochloride.

Embodiment 88 is a compound selected from the group consisting of:
N-[4-(4-aminoimidazo[4,5-c]quinolin-1-yl)-5-ethoxy-pentyl]acetamide;
N-[4-(4-aminoimidazo[4,5-c]quinolin-1-yl)-5-ethoxy-pentyl]propanamide;
N-[4-(4-aminoimidazo[4,5-c]quinolin-1-yl)-5-ethoxy-pentyl]-2-methylpropanamide;
N-[4-(4-aminoimidazo[4,5-c]quinolin-1-yl)-5-ethoxy-pentyl]butanamide;
N-[4-(4-aminoimidazo[4,5-c]quinolin-1-yl)-5-ethoxy-pentyl]-3-methylbutanamide;
N-[4-(4-aminoimidazo[4,5-c]quinolin-1-yl)-5-ethoxy-pentyl]pentanamide;
N-[4-(4-aminoimidazo[4,5-c]quinolin-1-yl)-5-ethoxy-pentyl]hexanamide;
N-[4-(4-aminoimidazo[4,5-c]quinolin-1-yl)-5-ethoxy-pentyl]octanamide;
N-[4-(4-aminoimidazo[4,5-c]quinolin-1-yl)-5-ethoxy-pentyl]nonanamide;
N-[4-(4-aminoimidazo[4,5-c]quinolin-1-yl)-5-ethoxy-pentyl]decanamide; or a pharmaceutically acceptable salt thereof.

Embodiment 89 is a compound selected from the group consisting of:
N-[4-(4-aminoimidazo[4,5-c]quinolin-1-yl)-5-ethoxy-pentyl]dodecanamide;
N-[4-(4-aminoimidazo[4,5-c]quinolin-1-yl)-5-ethoxy-pentyl]tetradecanamide;
N-[4-(4-aminoimidazo[4,5-c]quinolin-1-yl)-5-ethoxy-pentyl]hexadecanamide; or a pharmaceutically acceptable salt thereof.

Embodiment 90 is a compound selected from the group consisting of:
N-[4-(4-aminoimidazo[4,5-c]quinolin-1-yl)-5-ethoxy-pentyl]octadecanamide;
N-[4-(4-aminoimidazo[4,5-c]quinolin-1-yl)-5-ethoxy-pentyl]eicosanamide; or a pharmaceutically acceptable salt thereof.

Embodiment 91 is a pharmaceutical composition comprising a therapeutically effective amount of a compound or salt of any one of the embodiments 71-90 in combination with a pharmaceutically acceptable carrier.

Embodiment 92 is the pharmaceutical composition of embodiment 91, further comprising an antigen.

Embodiment 93 is the pharmaceutical composition of embodiment 91 or 92 for use in treating an infectious disease in a human or animal.

Embodiment 94 is the pharmaceutical composition of any one of the Embodiments 91-93 for use in treating a viral, bacterial, fungal, or parasitic infection in a human or animal.

Embodiment 95 is a method of inducing cytokine biosynthesis in a human or animal comprising administering an effective amount of a compound or salt of any one of the embodiments 71-90 to the human or animal.

Embodiment 96 is a method of inducing biosynthesis of IFN-alpha in a human or animal comprising administering an effective amount of a compound or salt of any one of the embodiments 71-90 to the human or animal.

Embodiment 97 is a method of inducing biosynthesis of IFN-gamma in a human or animal comprising administering an effective amount of a compound or salt of any one of the embodiments 71-90 to the human or animal.

Embodiment 98 is a method of inducing biosynthesis of TNF-alpha in a human or animal comprising administering an effective amount of a compound or salt of any one of the embodiments 71-90 to the human or animal.

Embodiment 99 is a method of inducing biosynthesis of IP-10 in a human or animal comprising administering an effective amount of a compound or salt of any one of the embodiments 71-90 to the human or animal.

Embodiment 100 is a compound or salt of any one of the embodiments 71-90 for use as a vaccine adjuvant in treating an infectious disease in a human or animal.

Embodiment 101 is a compound or salt of any one of the embodiments 71-90 for use as a vaccine adjuvant in treating a viral, bacterial, fungal, or parasitic infection in a human or animal.

Embodiment 102 is a compound or salt of any one of the embodiments 71-90, wherein the treatment is a therapeutic or prophylactic treatment.

Objects and advantages of the disclosure are further illustrated by the examples provided herein. The particular materials and amounts thereof recited in these examples, as well as other conditions and details, are merely illustrative and are not intended to be limiting. The person of ordinary skill in the art, after carefully reviewing the entirety of this disclosure, will be able to use materials and conditions in addition to those specifically described in the examples.

EXAMPLES

Automated flash chromatography (AFC) for purification of compounds was conducted using a ISOLARA HPFC system (an automated high-performance flash chromatography purification product available from Biotage, Inc, Charlottesville, Va.). The eluent used for each purification is described in the examples. In some chromatographic separations, the solvent mixture 80/18/2 v/v/v chloroform/methanol/concentrated ammonium hydroxide (CMA) was used as the polar component of the eluent. In these separations, CMA was mixed with chloroform in the ratio indicated below.

Proton nuclear magnetic resonance ($^1$H NMR) analysis was conducted using a BRUKER A500 NMR spectrometer (Bruker Corporation, Billerica, Mass.).

N-delta-BOC—N-alpha-CBZ-L-ornithine (CAS number 7733-29-1) was prepared by the procedure of Masiukiewicz et al. in *Organic Preparations and Procedures International* (*OPPI*), volume 34, 2002, pages 531-537; or obtained from the Alfa Aesar Company, Haverhill, Mass.

Ethyl chloroformate, L-ornithine hydrochloride, sodium borohydride, 10% palladium on carbon, N-methylmorpholine, and 3-chloroperbenzoic acid (57-86%) were obtained from the Sigma-Aldrich Company, St. Louis, Mo.

Diethyl sulfate, triethyl orthoformate, 3% platinum on carbon, and pyridine hydrochloride were obtained from the Alfa Aesar Company, Haverhill, Mass.

Isobutylchloroformate, and myristoyl chloride were obtained from the Oakwood Products Incorporated, Estill, S.C.

Decanoyl chloride was obtained from TCI America, Portland, Oreg.

Stearoyl chloride was obtained from MP Biomedicals Corporation, Santa Ana, Calif.

Example 1

N-[(4S)-4-(4-aminoimidazo[4,5-c]quinolin-1-yl)-5-ethoxy-pentyl]octadecanamide

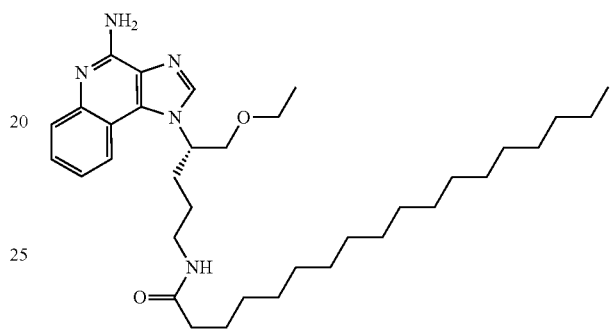

Part A

A stirred solution of N-delta-BOC—N-alpha-CBZ-L-ornithine (4.71 g, 12.9 mmol) dissolved in 15 mL of anhydrous tetrahydrofuran (THF) was cooled to negative 15° C. in an ice/methanol bath. The solution was combined with N-methyl morpholine (1.42 mL, 12.9 mmol) followed by the addition of ethyl chloroformate (1.23 mL, 12.9 mmol). After stirring for 5 minutes, the reaction mixture was filtered, rinsing with small portions THF, to remove N-methyl morpholine hydrochloride. The resulting filtrate was returned to the cold bath and a solution of 1.00 g of NaBH$_4$ in 7 mL of water was carefully added. After stirring for 20 minutes, the reaction mixture was combined with 100 mL of water followed by the addition of 75 mL of ethyl acetate. The layers were separated and the organic portion was washed with water and brine, dried over Na$_2$SO$_4$, filtered, and concentrated to give a colorless syrup. The syrup was concentrated from heptanes to provide 3.62 g of tert-butyl N-[(4S)-4-(benzyloxycarbonylamino)-5-hydroxy-pentyl]carbamate as a white solid.

Part B

A stirred solution of N-[(4S)-4-(benzyloxycarbonylamino)-5-hydroxy-pentyl]carbamate (3.62 g, 10.3 mmol) dissolved in 20 mL of toluene was combined with 1.15 g of 50% NaOH solution and diethyl sulfate (1.61 mL, 12.3 mmol). Tetrabutylammonium chloride hydrate (200 mg) was then added to the reaction mixture. After stirring for 2 hours, the reaction mixture was quenched with 10 mL of saturated NH$_4$OH solution and stirred for an additional 75 minutes. The reaction was then combined with water and the layers were separated. The organic layer was washed successively with water (2×) and brine, dried over Na$_2$SO$_4$, filtered, and concentrated under reduced pressure to give a colorless syrup. Purification by column chromatography (SiO$_2$, 20% ethyl acetate/hexanes to 50% ethyl acetate) provided 0.37 g of tert-butyl N-[(4S)-4-(benzyloxycarbonylamino)-5-ethoxy-pentyl]carbamate as a white crystalline solid.

Part C

A solution of tert-butyl N-[(4S)-4-(benzyloxycarbonylamino)-5-ethoxy-pentyl]carbamate (0.37 g, 0.97 mmol) in methanol was placed in a pressure bottle and 40 mg of 10% palladium on carbon was added. The bottle was then shaken under an atmosphere of hydrogen (40 PSI) overnight. The reaction mixture was filtered through a pad of CELITE, rinsing with methanol, and the filtrate was concentrated under reduced pressure to give 197 mg of tert-butyl N-[(4S)-4-amino-5-ethoxy-pentyl]carbamate as a colorless syrup.

Part D

A solution of tert-butyl N-[(4S)-4-amino-5-ethoxy-pentyl]carbamate (197 mg, 0.801 mmol) dissolved in 15 mL of dichloromethane was combined with 4-chloro-3-nitroquinoline (166 mg, 0.801 mmoL) and triethylamine (223 microliters, 1.60 mmol) and the reaction mixture was stirred under an atmosphere of nitrogen overnight. The reaction mixture was concentrated to give a yellow solid. The solid was dissolved in 20 mL of ethyl acetate and washed with water (3×) and brine. The organic portion was dried over $Na_2SO_4$, filtered, and concentrated to give a yellow solid. Purification by column chromatography ($SiO_2$, 20% ethyl acetate/hexanes to 50% ethyl acetate) provided 283 mg of tert-butyl N-[(4S)-5-ethoxy-4-[(3-nitro-4-quinolyl)amino]pentyl]carbamate as a yellow solid.

Part E

A suspension of tert-butyl N-[(4S)-5-ethoxy-4-[(3-nitro-4-quinolyl)amino]pentyl]carbamate (283 mg, 0.677 mmol) in 15 mL acetonitrile was placed in a pressure bottle and then 80 mg of 3% platinum on carbon was added. The bottle was then shaken under an atmosphere of hydrogen (40 PSI) for 90 minutes. The reaction mixture was filtered through a pad of CELITE, rinsing with acetonitrile, and the filtrate was concentrated under reduced pressure to give 262 mg of tert-butyl N-[(4S)-4-[(3-amino-4-quinolyl)amino]-5-ethoxy-pentyl]carbamate as an orange foam.

Part F

A solution of tert-butyl N-[(4S)-4-[(3-amino-4-quinolyl)amino]-5-ethoxy-pentyl]carbamate (262 mg, 0.67 mmol) dissolved in 10 mL of n-propyl acetate was combined with triethyl orthoformate (0.32 mL, 1.92 mmol) and 50 mg of pyridine hydrochloride and the mixture was heated to 105° C. overnight. The cooled reaction mixture was diluted with 25 mL of ethyl acetate and washed successively with saturated $NaHCO_3$ solution, water and brine. The organic portion was dried over $Na_2SO_4$, filtered, and concentrated to give a light brown syrup. Purification by column chromatography ($SiO_2$, 2.5% methanol/chloroform to 5% methanol/chloroform) provided 200 mg of tert-butyl N-[(4S)-5-ethoxy-4-imidazo[4,5-c]quinolin-1-yl-pentyl]carbamate as a light amber syrup.

Part G

A solution of tert-butyl N-[(4S)-5-ethoxy-4-imidazo[4,5-c]quinolin-1-yl-pentyl]carbamate (200 mg, 0.497 mmol) dissolved in 5 mL of dichloromethane was combined with 3-chloroperbenzoic acid (150 mg, 57-86%) and the reaction was stirred for 45 minutes. The reaction mixture was combined with 1 mL of concentrated $NH_4OH$ solution and p-toluenesulfonyl chloride (104 mg, 0.547 mmol). After stirring for 45 minutes, the reaction mixture was diluted with 10 mL of dichloromethane and washed with water (3×) and brine. The organic portion was dried over $Na_2SO_4$, filtered, and concentrated under reduced pressure. Purification by column chromatography ($SiO_2$, 33% CMA/chloroform to 50% CMA) gave a light brown syrup. The syrup was dissolved in 30 mL of dichloromethane and washed successively with 1N NaOH solution (2×), water and brine. The organic portion was dried over $Na_2SO_4$, filtered, and concentrated under reduced pressure. Further purification by column chromatography ($SiO_2$, 2.5% methanol/chloroform to 10% methanol/chloroform) provided 71 mg of tert-butyl N-[(4S)-4-(4-aminoimidazo[4,5-c]quinolin-1-yl)-5-ethoxy-pentyl]carbamate light brown syrup.

Part H

A solution of tert-butyl N-[(4S)-4-(4-aminoimidazo[4,5-c]quinolin-1-yl)-5-ethoxy-pentyl]carbamate (71 mg, 0.172 mmol) dissolved in 5 mL of ethanol was combined with 0.5 mL of concentrate hydrochloric acid solution. The mixture was heated to 90° C. for 60 minutes and then concentrated under reduced pressure. The resulting syrup was concentrated from ethanol to give 62 mg of 1-[(1S)-4-amino-1-(ethoxymethyl)butyl]imidazo[4,5-c]quinolin-4-amine dihydrochloride as a crusty white foam.

Part I

A solution of 1-[(1S)-4-amino-1-(ethoxymethyl)butyl]imidazo[4,5-c]quinolin-4-amine dihydrochloride (62 mg, 0.16 mmol) dissolved in 1.2 mL of anhydrous N,N-dimethylformamide (DMF) was combined with triethylamine (67 microliters, 0.48 mmol) and stearoyl chloride (50 mg, 0.16 mmol). After stirring for 90 minutes the reaction mixture was combined with 2 mL of dichloromethane and stirring was continued for 90 minutes. The reaction mixture was diluted with 20 mL of dichloromethane and water. A small amount of methanol was added to break up the resulting emulsion. The layers were separated and the organic portion was washed with water (2×) and brine. The organic portion was dried over $Na_2SO_4$, filtered, and concentrated under reduced pressure. Purification by column chromatography ($SiO_2$, 2.5% methanol/chloroform to 10% methanol/chloroform) gave 46 mg of a solid. Crystallization from 2 mL of hot acetonitrile provided 38 mg of N-[(4S)-4-(4-aminoimidazo[4,5-c]quinolin-1-yl)-5-ethoxy-pentyl]octadecanamide as white powder. $^1$H NMR ($CD_3OD$, 500 MHz) δ 8.41 (s, 1H), 8.27 (d, J=8.2 Hz, 1H), 7.74 (d, J=8.3 Hz, 1H), 7.54 (t, J=7.7 Hz, 1H), 7.38 (t, J=7.6 Hz, 1H), 5.39 (m, 1H), 4.01 (dd, J=5.8, 10.4 Hz, 1H), 3.93 (dd, J=3.8, 10.4 Hz, 1H), 3.52 (q, J=7.0 Hz, 2H), 3.22 (m, 2H), 2.19 (m, 2H), 2.14 (t, J=7.4 Hz, 2H), 1.63-1.51 (m, 4H), 1.32-1.23 (m, 24H), 1.12 (t, J=7.0 Hz, 3H), 0.92 (t, J=7.0 Hz, 3H).

Example 2

N-[(4S)-4-(4-aminoimidazo[4,5-c]quinolin-1-yl)-5-ethoxy-pentyl]tetradecanamide

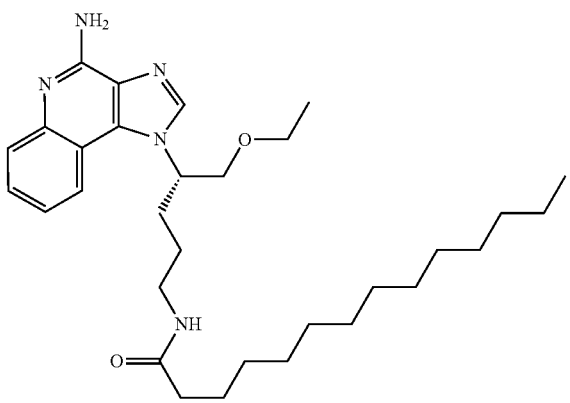 [SMILES: CCCCCCCCCCCCCC(=O)NCCC[C@@H](COCC)n1cnc2c(N)nc3ccccc3c21]

Part A

A stirred solution of N-delta-BOC—N-alpha-CBZ-L-ornithine (4.71 g, 12.9 mmol)] dissolved in 15 mL of anhydrous THF was cooled to negative 15° C. in an ice/methanol bath. N-methyl morpholine (1.43 mL, 13.0 mmol) was added to the solution followed by the addition of isobutyl chloroformate (1.69 mL, 13.0 mmol). After stirring for 5 minutes, the reaction mixture was filtered, rinsing with small portions THF, to remove N-methyl morpholine hydrochloride. The resulting filtrate was returned to the cold bath and a solution of 1.00 g $NaBH_4$ in 7 mL of $H_2O$ was carefully added. After stirring for 20 minutes, the reaction mixture was combined with 100 mL of water followed by the addition of 100 mL of ethyl acetate. The layers were separated and the aqueous portion was extracted with an additional 25 mL of ethyl acetate. The combined organic portions were washed with water and brine, dried over $Na_2SO_4$, filtered, and concentrated to give a colorless syrup. The syrup was concentrated from ethanol to provide 4.22 g of tert-butyl N-[(4S)-4-(benzyloxycarbonylamino)-5-hydroxy-pentyl]carbamate as a white solid.

Part B

A solution of tert-butyl N-[(4S)-4-(benzyloxycarbonylamino)-5-hydroxy-pentyl]carbamate (4.22 g, 12.0 mmol) in 50 mL of methanol was placed in a pressure bottle and 300 mg of 10% palladium on carbon was added. The bottle was then shaken under an atmosphere of hydrogen (40 PSI) overnight. The reaction mixture was filtered through a pad of CELITE, rinsing with MeOH, and the filtrate was concentrated under reduced pressure to give 2.61 g of tert-butyl N-[(4S)-4-amino-5-hydroxy-pentyl]carbamate as a colorless syrup.

Part C

A solution of tert-butyl N-[(4S)-4-amino-5-hydroxy-pentyl]carbamate (2.61 g, 12.0 mmol) dissolved in 50 mL of dichloromethane was combined with 4-chloro-3-nitroquinoline (2.49 g, 12.0 mmoL) and triethylamine (3.33 mL, 23.9 mmol) and the reaction mixture was stirred under an atmosphere of nitrogen overnight. The reaction mixture was concentrated to give a yellow solid. The solid was dissolved in 125 mL of ethyl acetate and washed with water (3×) and brine. The organic portion was dried over $Na_2SO_4$, filtered, and concentrated to give 4.23 g of tert-butyl N-[(4S)-5-hydroxy-4-[(3-nitro-4-quinolyl)amino]pentyl]carbamate as a yellow solid.

Part D

A suspension of tert-butyl N-[(4S)-5-hydroxy-4-[(3-nitro-4-quinolyl)amino]pentyl]carbamate (4.23 g, 10.8 mmol) in 125 mL acetonitrile was placed in a pressure bottle and 200 mg of 3% platinum on carbon was added. The bottle was then shaken under an atmosphere of hydrogen (40 PSI) for 4 hours. The reaction mixture was filtered through a pad of CELITE, rinsing with acetonitrile, and the filtrate was concentrated under reduced pressure to give 3.80 g of tert-butyl N-[(4S)-4-[(3-amino-4-quinolyl)amino]-5-hydroxy-pentyl]carbamate as an orange foam.

Part E

A solution of tert-butyl N-[(4S)-4-[(3-amino-4-quinolyl)amino]-5-hydroxy-pentyl]carbamate (3.80 g, 10.6 mmol) dissolved in 40 mL of n-propyl acetate was combined with triethyl orthoformate (3.50 mL, 21.1 mmol) and 300 mg of pyridine hydrochloride and the mixture was heated to 105° C. for 2 days. The cooled reaction mixture was diluted with 50 mL of ethyl acetate and washed successively with saturated $NaHCO_3$ solution, water and brine. The organic portion was dried over $Na_2SO_4$, filtered, and concentrated to give a light brown syrup. Purification by column chromatography ($SiO_2$, 1% methanol/chloroform to 10% methanol/chloroform) provided 2.40 g of tert-butyl N-[(4S)-5-hydroxy-4-imidazo[4,5-c]quinolin-1-yl-pentyl]carbamate as a white foam.

Part F

A 200 mL bound bottom flask was charged with 1.04 g of 50% aqueous NaOH solution and 150 mg of tetrabutylammonium chloride hydrate. A solution of tert-butyl N-[(4S)-5-hydroxy-4-imidazo[4,5-c]quinolin-1-yl-pentyl]carbamate (2.00 g, 5.40 mmol) dissolved in 40 mL of hot toluene was added and the reaction mixture was heated to 85° C. Diethyl sulfate (886 microliters, 6.77 mmol) was added and the mixture was stirred for 4 hours. The reaction mixture was cooled and quenched with 10 mL of saturated $NH_4OH$ solution. After stirring for 75 min, the reaction was combined with water and toluene and the layers were separated. The organic layer was washed successively with $H_2O$ (2×) and brine, dried over $Na_2SO_4$, filtered, and concentrated under reduced pressure to give colorless syrup. Purification by column chromatography ($SiO_2$, 20% ethyl acetate/hexanes to 50% ethyl acetate) provided 888 mg of tert-butyl N-[(4S)-5-ethoxy-4-imidazo[4,5-c]quinolin-1-yl-pentyl]carbamate as a golden syrup.

Part G

The procedures of Parts G and H of Example 1 were followed to provide 321 mg (0.832 mmol) of 1-[(1S)-4-amino-1-(ethoxymethyl)butyl]imidazo[4,5-c]quinolin-4-amine dihydrochloride. The compound was dissolved in 5 mL of anhydrous DMF and combined with triethylamine (347 microliters, 2.50 mmol) and myristoyl chloride (226 microliters, 0.832 mmol). After stirring overnight, 25 mL of water was added to the reaction mixture. The resulting solid was isolated by filtration, rinsed with water, dissolved in 10% methanol/chloroform, and then concentrated under reduced pressure to give a waxy solid. Purification by column chromatography ($SiO_2$, 2% methanol/chloroform to 15% methanol/chloroform) gave a light brown solid. Crystallization from acetonitrile provided 30 mg of N-[(4S)-4-(4-aminoimidazo[4,5-c]quinolin-1-yl)-5-ethoxy-pentyl]tetradecanamide as light brown solid. $^1$H NMR ($CD_3OD$, 500 MHz) δ 8.42 (s, 1H), 8.29 (d, J=8.1 Hz, 1H), 7.75 (d, J=8.3 Hz, 1H), 7.56 (t, J=7.7 Hz, 1H), 7.40 (t, J=7.6 Hz, 1H), 5.40 (m, 1H), 4.01 (dd, J=5.4, 10.0 Hz, 1H), 3.93 (dd, J=3.0, 10.2 Hz, 1H), 3.52 (q, J=6.9 Hz, 2H), 3.22 (m, 2H), 2.27-2.08 (m, 4H), 1.64-1.50 (m, 4H), 1.39-1.21 (m, 20H), 1.11 (t, J=7.0 Hz, 3H), 0.91 (t, J=6.8 Hz, 3H).

Example 3

N-[(4S)-4-(4-aminoimidazo[4,5-c]quinolin-1-yl)-5-ethoxy-pentyl]decanamide

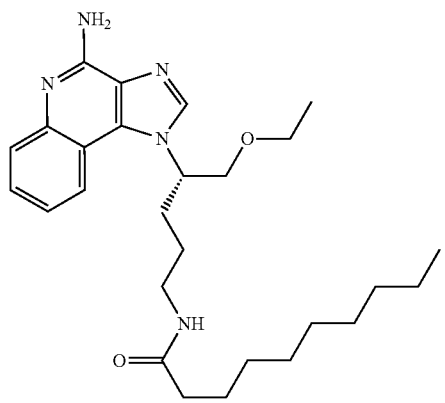 [SMILES: CCCCCCCCCC(=O)NCCC[C@@H](COCC)n1cnc2c(N)nc3ccccc3c21]

A solution of 1-[(1S)-4-amino-1-(ethoxymethyl)butyl]imidazo[4,5-c]quinolin-4-amine dihydrochloride (360 mg, 0.933 mmol) dissolved in 5 mL of anhydrous DMF was combined with triethylamine (390 microliters, 2.80 mmol) and decanoyl chloride (194 microliters, 0.933 mmol). After stirring overnight, 25 mL of water was added to the reaction mixture. The resulting solid was isolated by filtration, rinsed with water and the dissolved in 10% methanol/chloroform, and then concentrated under reduced pressure to give a waxy solid. Purification by column chromatography ($SiO_2$, 2% methanol/chloroform to 15% methanol/chloroform) gave a light brown solid. Crystallization from acetonitrile provided 90 mg of N-[(4S)-4-(4-aminoimidazo[4,5-c]quinolin-1-yl)-5-ethoxy-pentyl]decanamide as a white solid. $^1$H NMR ($CD_3OD$, 500 MHz) δ 8.54 (s, 1H), 8.44 (d, J=8.2 Hz, 1H), 7.80 (m, 1H), 7.72 (m, 1H), 7.58 (m, 1H), 5.44 (m, 1H), 3.99 (dd, J=6.3, 10.4 Hz, 1H), 3.95 (dd, J=3.7, 10.4 Hz, 1H), 3.51 (q, J=7.0 Hz, 2H), 3.21 (m, 2H), 2.21 (m, 2H), 2.13 (t, J=7.5 Hz, 2H), 1.63-1.51 (m, 4H), 1.33-1.22 (m, 12H), 1.09 (t, J=7.0 Hz, 3H), 0.91 (t, J=7.0 Hz, 3H).

Cytokine Induction in Human Cells

Whole blood was obtained from healthy human donors and collected by venipuncture into vacutainer tubes or syringes containing EDTA. Human peripheral blood mononuclear cells (PBMC) were purified from the whole blood by density gradient centrifugation. Histopaque 1077 (15 mL, Sigma, St. Louis, Mo.) was transferred to 6×50 mL sterile polypropylene conical tubes. The Histopaque was overlayed with 15-25 mL of blood diluted 1:2 in Hank's Balanced Salts Solution (HBSS) (Gibco, Life Technology, Grand Island N.Y.). The tubes were then centrifuged at 1370 rpm for 30 minutes at 20° C., with no brake (400×g, GH 3.8A Rotor).

The interface (buffy coat) containing the PBMC was collected and placed in a new sterile 50 mL conical polypropylene centrifuge tube. The PBMC were mixed with an equal volume of HBSS (about 20 mL from the interface and about 20 mL of HBSS), and then centrifuged at 1090 rpm, 10 min, 20° C., with brake (270×g, GH 3.8A Rotor). After completing centrifugation, the cells were resuspended in 2-3 mL ACK Red blood cell lysis buffer (ammonium chloride potassium solution, Gibco, Life Technology) and incubated for 2-5 minutes at 20° C. Next, HBSS (40 mL) was added to the cells, and the sample was centrifuged at 270×g for 10 min at 20° C. The supernatant was decanted, and the cell pellet was resuspended in 5 mL AIM V® Medium (Gibco, Life Technology). Cell aggregates and debris were removed by filtering the cell solution through a BD Falcon 70 micron nylon cell strainer (BD Biosciences, San Jose, Calif.).

The number of viable cells was determined by counting with a Miltenyi FACS instrument (Miltenyi Biotec Inc., San Diego, Calif.) or by using a hemacytometer. For determining cell viability with a hemacytometer, the cells were diluted 1/10 in 0.4% trypan blue and HBSS (specifically, 50 microliter of trypan blue+40 microliter of HBSS+10 microliter of cell solution were added to a microfuge tube and mixed). Ten microliters of the diluted cells were then applied to the hemacytometer, and the number of viable PBMC were determined by microscopy.

The PBMC sample was then resuspended in 96-well plates at a concentration of $8 \times 10^5$ cells/well in 0.1 mL of AIM-V medium. Each compound was solubilized in DMSO to create a 3 mM stock solution. The stock solution was then further diluted with AIM-V medium to prepare the serial dilutions. The diluted compound (100 microliters) was then transferred to the PBMCs to achieve final compound concentrations of 30, 10, 3.3, 1.1, 0.37, 0.12, 0.04, 0.01 micromolar. The plates also had both positive and negative controls. The negative control wells contained only AIM-V medium with no example compound. The positive control wells contained imiquimod serially diluted to concentrations of 30, 10, 3.3, 1.1, 0.37, 0.12, 0.04, 0.01 micromolar. The plates were then cultured at 37° C./5% $CO_2$ for 21-24 hrs. Cell-free supernatants were harvested by centrifuging the 96-well plates at 2100 rpm, 23° C. for 10 minutes. Approximately 160 microliters of the supernatant were then stored in a NUNC 96-well plate, covered with the compression cap and stored at −80° C. until the cytokine analysis was done.

IFN-alpha cytokine levels (pg/mL) were measured by ELISA (human IFN-α, pan specific, Mabtech, Cincinnati, Ohio). IFN-gamma and TNF-alpha levels (pg/mL) were measured by multiplex bead assay (magnetic beads, R & D Systems Minneapolis, Minn.) according to the manufacturer's instructions.

The data was analyzed to determine the minimum effective concentration (MEC) for each compound at which induction of a particular cytokine was observed in the assay. Specifically, the minimum effective concentration of each compound (micromolar) was determined as the lowest concentration of the compound that induced a measured cytokine response at a level (pictograms/mL) that was at least 2× greater than that observed with the negative control wells. The results are presented in Table 25. The "designation "≤0.01" indicates that cytokine induction was observed at the lowest concentration of compound evaluated in the assays.

TABLE 25

| Compound | MEC to Induce Cytokine (micromolar) | | |
|---|---|---|---|
| | IFN-alpha | IFN-gamma | TNF-alpha |
| Example 1 | ≤0.01 | 1.1 | ≤0.01 |
| Example 2 | ≤0.01 | 0.04 | ≤0.01 |
| Example 3 | ≤0.01 | 0.04 | ≤0.01 |

The complete disclosures of the patents, patent documents, and publications cited herein are incorporated by reference in their entirety as if each were individually incorporated. Various modifications and alterations to this invention will become apparent to those of ordinary skill in

What is claimed is:

1. A compound of the Formula (I):

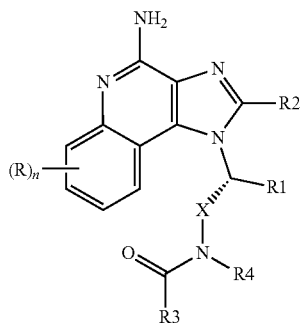

Formula I wherein:

n is an integer of 0 or 1;
R is selected from the group consisting of halogen, hydroxy, alkyl, alkoxy, and —C(O)—O-alkyl;
X is alkylene, wherein the alkylene group can be optionally interrupted by one or more —O— groups;
R1 is selected from the group consisting of $C_{1-5}$alkyl and —$C_{1-3}$alkylene-O—$C_{1-3}$alkyl;
R2 is selected from the group consisting of hydrogen, methyl, ethyl, n-propyl, n-butyl, —$CH_2OCH_3$, —$CH_2OCH_2CH_3$, and —$CH_2CH_2OCH_3$;
R3 is alkyl, wherein the alkyl group can be optionally interrupted by one or more —O— groups;
R4 is selected from the group consisting of hydrogen, methyl, ethyl, n-propyl, and isopropyl; or a pharmaceutically acceptable salt thereof.

2. The compound or salt of claim 1, wherein X is $C_{1-8}$alkylene.

3. The compound or salt of claim 1, wherein X is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, and —$CH_2CH_2CH_2CH_2CH_2CH_2CH_2CH_2$—.

4. The compound or salt of claim 1, wherein R1 is —$CH_2OCH_3$ or —$CH_2OCH_2CH_3$.

5. The compound or salt of claim 1, wherein R2 is selected from the group consisting of hydrogen, methyl, and ethyl.

6. The compound or salt of claim 1, wherein R2 is hydrogen.

7. The compound or salt of claim 1, wherein R3 is $C_{5-19}$alkyl.

8. The compound or salt of claim 1, wherein R3 is —$CH_2(CH_2)_{3-17}CH_3$.

9. The compound or salt of claim 1, wherein R is selected from the group consisting of hydroxy, F, and Cl.

10. The compound or salt of claim 1, wherein n is 0.

11. The compound or salt of claim 1, wherein R4 is hydrogen.

12. A vaccine adjuvant comprising the compound or salt of claim 1.

13. A method of inducing biosynthesis of IFN-alpha in a human or animal comprising administering an effective amount of a compound or salt of claim 1 to the human or animal.

14. A method of inducing biosynthesis of TNF-alpha in a human or animal comprising administering an effective amount of a compound or salt of claim 1 to the human or animal.

15. A pharmaceutical composition comprising a therapeutically effective amount of a compound or salt of claim 1 in combination with a pharmaceutically acceptable carrier.

* * * * *